United States Patent
Choi et al.

(10) Patent No.: US 10,522,764 B2
(45) Date of Patent: Dec. 31, 2019

(54) COMPOUND, LIGHT-EMITTING ELEMENT COMPRISING SAME AND ELECTRONIC DEVICE COMPRISING THE LIGHT-EMITTING ELEMENT

(71) Applicant: LMS Co., Ltd., Pyeongtaek-si (KR)

(72) Inventors: Jeong Og Choi, Seoul (KR); Oh Kwan Kwon, Anyang-si (KR); Joon Ho Jung, Hwaseong-si (KR)

(73) Assignee: LMS Co., Ltd., Pyeongtaek-si (KR)

( * ) Notice: Subject to any disclaimer, the term of this patent is extended or adjusted under 35 U.S.C. 154(b) by 504 days.

(21) Appl. No.: 14/420,582

(22) PCT Filed: Aug. 9, 2013

(86) PCT No.: PCT/KR2013/007205
§ 371 (c)(1),
(2) Date: Jul. 10, 2015

(87) PCT Pub. No.: WO2014/025231
PCT Pub. Date: Feb. 13, 2014

(65) Prior Publication Data
US 2015/0349271 A1    Dec. 3, 2015

(30) Foreign Application Priority Data

Aug. 10, 2012  (KR) .................. 10-2012-0087715
Aug. 9, 2013   (KR) .................. 10-2013-0094720

(51) Int. Cl.
*H01L 51/00*   (2006.01)
*C07D 495/14*  (2006.01)
(Continued)

(52) U.S. Cl.
CPC ........ *H01L 51/0071* (2013.01); *C07D 495/14* (2013.01); *C07D 519/00* (2013.01);
(Continued)

(58) Field of Classification Search
CPC combination set(s) only.
See application file for complete search history.

(56) References Cited

U.S. PATENT DOCUMENTS

2008/0145665 A1   6/2008  Ye et al.
2009/0134784 A1   5/2009  Lin et al.
(Continued)

FOREIGN PATENT DOCUMENTS

DE   102010030500 A1 * 12/2011  ............. B82Y 10/00
KR   1020090097872 A      9/2009
(Continued)

OTHER PUBLICATIONS

Machine translation of DE 102010030500 generated on Apr. 24, 2017.*

(Continued)

*Primary Examiner* — Jennifer A Chriss
*Assistant Examiner* — Sean M DeGuire
(74) *Attorney, Agent, or Firm* — Polsinelli PC

(57) ABSTRACT

The present invention relates to a compound, and a light-emitting element and an electronic device including the same, and, more particularly, to a compound for an organic light-emitting element, and a light-emitting element and an electronic device including the same. The compound according to the present invention can improve hole injection and/or transport abilities.

9 Claims, 2 Drawing Sheets

(51) Int. Cl.
  *C07D 519/00* (2006.01)
  *C07F 7/08* (2006.01)
  *H01L 51/50* (2006.01)

(52) U.S. Cl.
  CPC ........ *C07F 7/0812* (2013.01); *H01L 51/0052* (2013.01); *H01L 51/0058* (2013.01); *H01L 51/0072* (2013.01); *H01L 51/0074* (2013.01); *H01L 51/0094* (2013.01); *H01L 51/0073* (2013.01); *H01L 51/506* (2013.01); *H01L 51/5056* (2013.01); *H01L 51/5064* (2013.01)

(56) References Cited

U.S. PATENT DOCUMENTS

| | | | |
|---|---|---|---|
| 2011/0177007 A1* | 7/2011 | Rajagopalan | A61K 41/0057 424/9.61 |
| 2011/0260138 A1 | 10/2011 | Xia et al. | |

FOREIGN PATENT DOCUMENTS

| | | | |
|---|---|---|---|
| KR | 20100045311 A | * | 5/2010 |
| KR | 1020100099327 A | | 9/2010 |
| KR | 1020110131155 A | | 12/2011 |
| WO | 2011137072 A1 | | 11/2011 |

OTHER PUBLICATIONS

Machine translation of KR 2010004311 generated on Apr. 24, 2017.*

Meng, H. and Herron N., Organic Light-Emitting Materials and Devices, Second Edition, Chapter 3, Edited by Zhigang Rick Li, CRC Press 2015, pp. 309-488.*

Zhang et al.; "Highly Fluorescent Conjugated Copolymers Containing Dithieno[3,2-b:2',3'-d]pyrrole"; Macromolecular Rapid Communications; 2008; pp. 1603-1608; vol. 29.

* cited by examiner

[Fig.1]
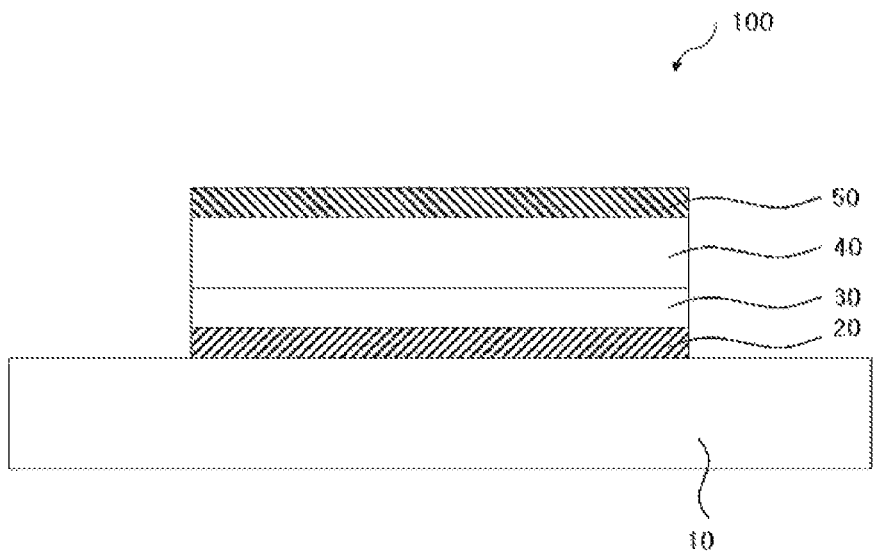
[Fig.2]
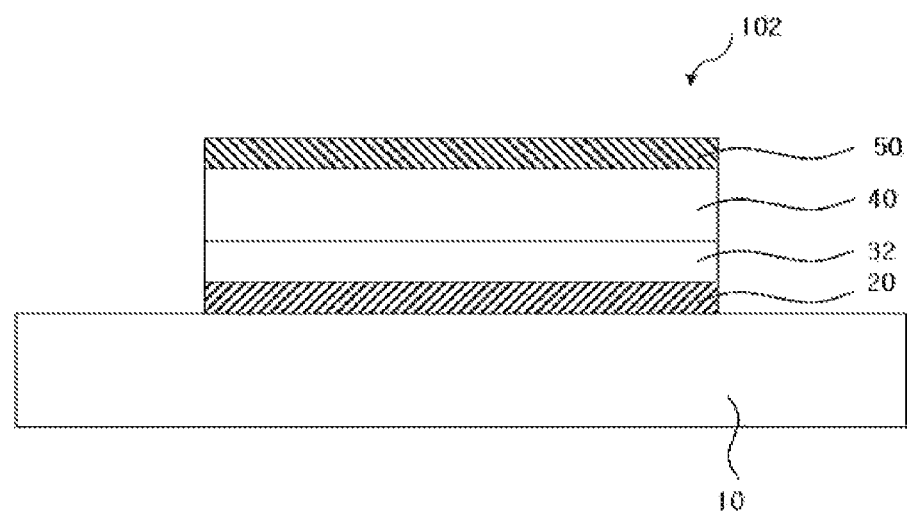

[Fig.3]
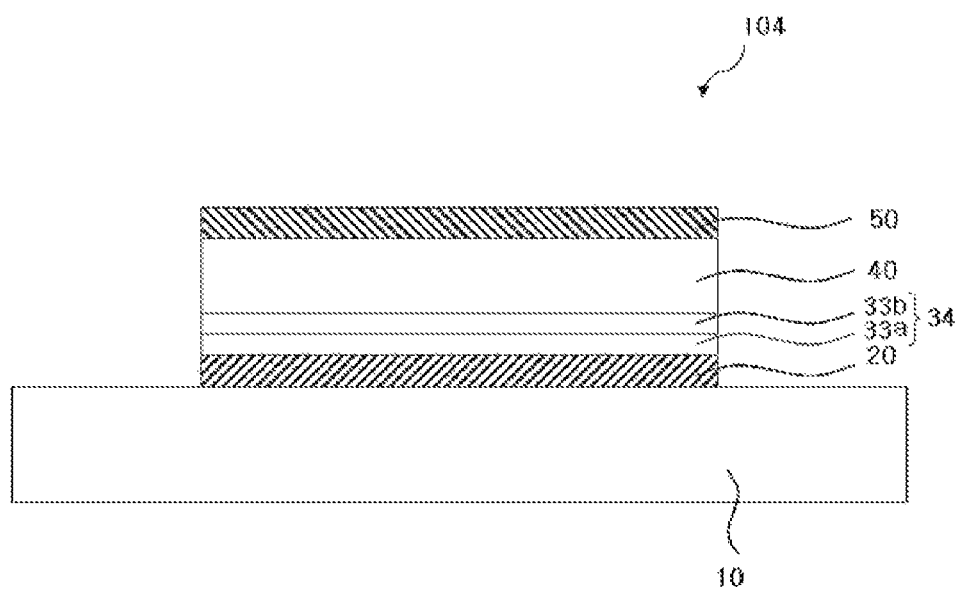

COMPOUND, LIGHT-EMITTING ELEMENT COMPRISING SAME AND ELECTRONIC DEVICE COMPRISING THE LIGHT-EMITTING ELEMENT

CROSS-REFERENCE TO RELATED APPLICATIONS

This application is the United States national phase of International Application No. PCT/KR2013/007205 filed Aug. 9, 2013, and claims priority to Korean Patent Application Nos. 10-2012-0087715 and 10-2013-0094720 filed Aug. 10, 2012 and Aug. 9, 2013 respectively, the disclosures of which are hereby incorporated in their entirety by reference.

BACKGROUND

Field of the Invention

The present invention relates to a novel compound, and a light-emitting element and an electronic device including the same, and more particularly, to a compound for an organic light-emitting element, and a light-emitting element and an electronic device including the same.

Background Art

Generally, a light-emitting element includes two electrodes facing each other, and a light emitting layer including a light emitting compound interposed between the electrodes. If a current flows between the electrodes, the light emitting compound generates light. In a display device using the light-emitting element, since a separate light source device is not required, a weight, a size, or a thickness of the display device may be reduced. Further, the display device using the light-emitting element has merits in that excellent viewing angle, contrast ratio, color reproducibility, or the like and low consumption power as compared to a display device using a backlight and a liquid crystal.

The light-emitting element may further include a hole transport layer disposed between an anode and the light emitting layer. The hole transport layer may stabilize an interface between the anode and the light emitting layer and minimize an energy barrier therebetween.

However, the light-emitting element has problems so far in that a light emitting life-span is short, power efficiency is low, and thermal stability (heat resistance) is low. In order to solve the aforementioned problems, various compounds have been developed as a material of the light-emitting element, but there is a limitation in manufacturing the light-emitting element satisfying all aspects in view of the light emitting life-span, power efficiency, and thermal stability.

SUMMARY OF THE INVENTION

Technical Problem

Therefore, the present invention has been made in an effort to provide a novel compound for improving hole injection and transport abilities in a light-emitting element.

Further, the present invention has been made in an effort to provide a light-emitting element including the compound.

Further, the present invention has been made in an effort to provide an electronic device including the light-emitting element.

Technical Solution

An exemplary embodiment of the present invention provides a compound represented by the following Chemical Formula 1.

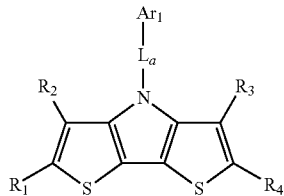

[Chemical Formula 1]

In Chemical Formula 1, $R_1$, $R_2$, $R_3$, and $R_4$ each independently represent *-$L_b$-Z, hydrogen, an aryl group having 6 to 60 carbon atoms, a heteroaryl group having 2 to 60 carbon atoms, an alkenyl group having 2 to 60 carbon atoms, or an alkynyl group having 2 to 60 carbon atoms, at least one of $R_1$, $R_2$, $R_3$, and $R_4$ represents *-$L_b$-Z, Z is represented by hydrogen, the following Chemical Formula 2, or the following Chemical Formula 3,

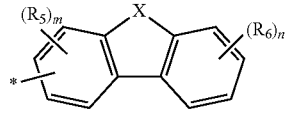

[Chemical Formula 2]

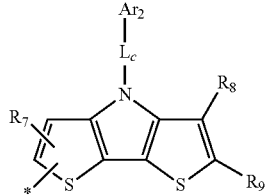

[Chemical Formula 3]

X represents O, S, N-$L_d$-$AR_3$, or Si($R_{10}$)($R_{11}$), $Ar_1$, $Ar_2$, and $Ar_3$ each independently represent *-$A_1$-$A_2$-$A_3$-$A_4$, $A_1$, $A_2$, and $A_3$ each independently represent a single bond, —O—, —S—, a linear or branched alkylene group (—($CH_2$)$_j$—, herein, j is an integer of 1 to 60) having 1 to 60 carbon atoms, an arylene group having 6 to 60 carbon atoms, a heteroarylene group having 2 to 60 carbon atoms, a cycloalkylene group having 3 to 60 carbon atoms, a heterocycloalkylene group having 2 to 60 carbon atoms, an adamantylene group, a bicycloalkylene group having 7 to 60 carbon atoms, an alkenylene group having 2 to 60 carbon atoms, or an alkynylene group having 2 to 60 carbon atoms, $A_4$ represents hydrogen, an alkyl group having 1 to 60 carbon atoms, an aryl group having 6 to 60 carbon atoms, a heteroaryl group having 2 to 60 carbon atoms, a cycloalkyl group having 3 to 60 carbon atoms, a heterocycloalkyl group having 2 to 60 carbon atoms, an adamantyl group, a bicycloalkyl group having 7 to 60 carbon atoms, an alkenyl group having 2 to 60 carbon atoms, or an alkynyl group having 2 to 60 carbon atoms, $R_5$, $R_6$, $R_7$, $R_8$, $R_9$, $R_{10}$, and $R_{11}$ each independently represent hydrogen, an alkyl group having 1 to 10 carbon atoms, an alkenyl group having 2 to 60 carbon atoms, an alkynyl group having 2 to 60 carbon atoms, a cycloalkyl group having 3 to 60 carbon atoms, an aryl group having 6 to 60 carbon atoms, or a heteroaryl group having 2 to 60 carbon atoms, m represents an integer of 0 to 3, and n represents an integer of 0 to 4, $L_a$, $L_b$, $L_c$, and $L_d$ each independently represent *-$(L_1)_p$-$(L_2)_q$-$(L_3)_r$-$(L_4)_s$-*, $L_1$, $L_2$, $L_3$, and $L_4$ each independently represent a single bond, —O—, —S—, an arylene group having 6 to 60 carbon atoms, a heteroarylene group having 2 to 60 carbon atoms, an alkenylene group having 2 to 60 carbon atoms, an alkynylene group having 2 to 60 carbon atoms, or a cycloalkylene group having 3 to 60 carbon atoms, p, q, r, and s each independently represent an integer of 0 to 2, and one or more hydrogens of $R_1$ to $R_4$, $L_a$, and $Ar_1$ of Chemical Formula 1 are each independently unsubstituted or substituted by an alkyl group having 1 to 6 carbon atoms, an alkenyl group having 2 to 6 carbon atoms, an alkoxy group having 1 to 6 carbon atoms, an aryl group having 6 to 60 carbon atoms, a heteroaryl group having 2 to 60 carbon atoms, an aryloxy group having 6 to 60 carbon atoms, an arylthio group having 6 to 60 carbon atoms, an alkoxycarbonyl group having 1 to 6 carbon atoms, a halogen group, a cyano group, a nitro group, a hydroxyl group, or a carboxyl group.

Another exemplary embodiment of the present invention provides a light-emitting element including a first electrode, a second electrode, a light emitting layer, and a hole transportable layer including the compound represented by Chemical Formula 1. The first electrode and the second electrode may face each other, the light emitting layer may be interposed between the first and second electrodes, and the hole transportable layer may be disposed between the first electrode and the light emitting layer.

In the exemplary embodiment, the hole transportable layer may include a first layer including the compound and a P-type dopant, and a second layer including the compound. For example, the first layer may be disposed between the first electrode and the light emitting layer, and the second layer may be disposed between the first layer and the light emitting layer. In this case, the second layer may further include a dopant of a kind that is substantially the same as or different from the P-type dopant of the first layer.

Yet another exemplary embodiment of the present invention provides an electronic device including a hole transportable layer including the compound represented by Chemical Formula 1.

Effect of the Invention

According to the aforementioned novel compound, and the light-emitting element and the electronic device including the same, the novel compound of the present invention can improve hole injection and/or transport abilities in the light-emitting element.

Further, it is possible to improve light emitting efficiency of the light-emitting element and increase a life-span by using the compound. Further, it is possible to improve thermal stability (heat resistance) of the light-emitting element.

BRIEF DESCRIPTION OF DRAWINGS

FIG. 1 is a cross-sectional view for illustrating a light-emitting element according to an exemplary embodiment of the present invention.

FIG. 2 is a cross-sectional view for illustrating a light-emitting element according to another exemplary embodiment of the present invention.

FIG. 3 is a cross-sectional view for illustrating a light-emitting element according to yet another exemplary embodiment of the present invention.

DETAILED DESCRIPTION OF THE INVENTION

Hereinafter, a novel compound according to the present invention will be first described, and a light-emitting element including the compound will be described in more detail with reference to the accompanying drawings.

The novel compound according to the present invention is represented by the following Chemical Formula 1.

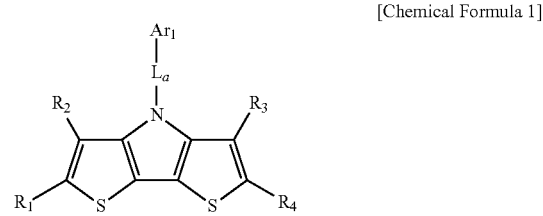

[Chemical Formula 1]

In Chemical Formula 1, $R_1$, $R_2$, $R_3$, and $R_4$ each independently represent *-$L_b$-Z, hydrogen, an aryl group having 6 to 60 carbon atoms, a heteroaryl group having 2 to 60 carbon atoms, an alkenyl group having 2 to 60 carbon atoms, or an alkynyl group having 2 to 60 carbon atoms, at least one of $R_1$, $R_2$, $R_3$, and $R_4$ represents *-$L_b$-Z, Z is represented by hydrogen, the following Chemical Formula 2, or the following Chemical Formula 3,

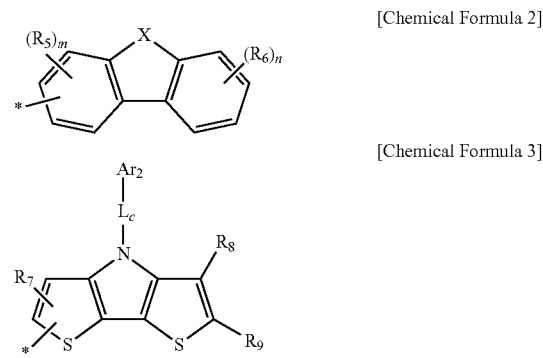

[Chemical Formula 2]

[Chemical Formula 3]

X represents O, S, N-$L_d$-$AR_3$, or Si$(R_{10})(R_{11})$, $Ar_1$, $Ar_2$, and $Ar_3$ each independently represent *-$A_1$-$A_2$-$A_3$-$A_4$, $A_1$, $A_2$, and $A_3$ each independently represent a single bond, —O—, —S—, a linear or branched alkylene group (—$(CH_2)_j$—, herein, j is an integer of 1 to 60) having 1 to 60 carbon atoms, an arylene group having 6 to 60 carbon atoms, a heteroarylene group having 2 to 60 carbon atoms, a cycloalkylene group having 3 to 60 carbon atoms, a heterocycloalkylene group having 2 to 60 carbon atoms, an adamantylene group, a bicycloalkylene group having 7 to 60 carbon atoms, an alkenylene group having 2 to 60 carbon atoms, or an alkynylene group having 2 to 60 carbon atoms, $A_4$ represents hydrogen, an alkyl group having 1 to 60 carbon atoms, an aryl group having 6 to 60 carbon atoms, a heteroaryl group having 2 to 60 carbon atoms, a cycloalkyl group having 3 to 60 carbon atoms, a heterocycloalkyl group having 2 to 60 carbon atoms, an adamantyl group, a bicycloalkyl group having 7 to 60 carbon atoms, an alkenyl group having 2 to 60 carbon atoms, or an alkynyl group having 2 to 60 carbon atoms, $R_5$, $R_6$, $R_7$, $R_8$, $R_9$, $R_{10}$, and $R_{11}$ each independently represent hydrogen, an alkyl group having 1 to 10 carbon atoms, an alkenyl group having 2 to 60 carbon atoms, an alkynyl group having 2 to 60 carbon atoms, a cycloalkyl group having 3 to 60 carbon atoms, an aryl group having 6 to 60 carbon atoms, or a heteroaryl group having 2 to 60 carbon atoms, m represents an integer of 0 to 3, and n represents an integer of 0 to 4, $L_a$, $L_b$, $L_c$, and $L_d$ each independently represent *-$(L_1)_p$-$(L_2)_q$-$(L_3)_r$-$(L_4)_s$-*, $L_1$, $L_2$, $L_3$, and $L_4$ each independently represent a single bond, —O—, —S—, an arylene group having 6 to 60 carbon atoms, a heteroarylene group having 2 to 60 carbon atoms, an alkenylene group having 2 to 60 carbon atoms, an alkynylene group having 2 to 60 carbon atoms, or a cycloalkylene group having 3 to 60 carbon atoms, and p, q, r, and s each independently represent an integer of 0 to 2.

For example, in the case where p, q, r, and s are all 0, it is defined that $L_1$, $L_2$, $L_3$, and $L_4$ represent a "single bond".

One or more of hydrogens of $R_1$ to $R_4$, $L_a$, and $Ar_1$ of Chemical Formula 1 are each independently unsubstituted or substituted by one or more substituent groups selected from the group consisting of an alkyl group having 1 to 6 carbon atoms, an alkenyl group having 2 to 6 carbon atoms, an alkoxy group having 1 to 6 carbon atoms, an aryl group having 6 to 60 carbon atoms, a heteroaryl group having 2 to 60 carbon atoms, an aryloxy group having 6 to 60 carbon atoms, an arylthio group having 6 to 60 carbon atoms, an alkoxycarbonyl group having 1 to 6 carbon atoms, a halogen group, a cyano group, a nitro group, a hydroxyl group, and a carboxyl group.

In the present invention, the "aryl group" is defined by a monovalent substituent group derived from aromatic hydrocarbon.

Specific examples of the aryl group may include a phenyl group, a naphthyl group, an anthracenyl group, a phenanathryl group, a naphthacenyl group, a pyrenyl group, a tolyl group, a biphenyl group, a terphenyl group, a chrycenyl group, a spirobifluorenyl group, a fluoranthenyl group, a fluorenyl group, a perylenyl group, an indenyl group, an azulenyl group, a heptalenyl group, a phenalenyl group, a phenanthrenyl group, and the like.

The "heteroaryl group" represents an "aromatic heterocycle" or "heterocyclic" derived from a monocycle or a condensed cycle. The heteroaryl group may include at least one of nitrogen (N), sulfur (S), oxygen (O), phosphorus (P), selenium (Se), and silicon (Si) as heteroatoms.

Specific examples of the heteroaryl group may include a nitrogen-containing heteroaryl group including a pyrrolyl group, a pyridyl group, a pyridazinyl group, a pyrimidinyl group, a pyrazinyl group, a triazolyl group, a tetrazolyl group, a benzotriazolyl group, a pyrazolyl group, an imidazolyl group, a benzimidazolyl group, an indolyl group, an isoindolyl group, an indolizinyl group, a purinyl group, an indazolyl group, a quinolyl group, an isoquinolinyl group, a quinolizinyl group, a phthalazinyl group, a naphthylidinyl group, a quinoxalinyl group, a quinazolinyl group, a cinnolinyl group, a pteridinyl group, an imidazotriazinyl group, a pyrazinopyridazinyl group, an acrydinyl group, a phenanthridinyl group, a carbazolyl group, a carbazolinyl group, a pyrimidinyl group, a phenanthrolinyl group, a phenazinyl group, an imidazopyridinyl group, an imidazopyrimidinyl group, a pyrazolopyridinyl group, a pyrazolopyridinyl group, and the like; a sulfur-containing heteroaryl group including a thienyl group, a benzothienyl group, a dibenzothienyl group, and the like; and an oxygen-containing heteroaryl group including a furyl group, a pyranyl group, a cyclopentapyranyl group, a benzofuranyl group, an isobenzofuranyl group, a dibenzofuranyl group, and the like. Further, specific examples of the heteroaryl group may include compounds including at least two heteroatoms, such as a thiazolyl group, an isothiazolyl group, a benzothiazolyl group, a benzthiadiazolyl group, a phenothiazinyl group, an isoxazolyl group, a furazanyl group, a phenoxazinyl group, an oxazolyl group, a benzoxazolyl group, an oxadiazolyl group, a pyrazolooxazolyl group, an imidazothiazolyl group, a thienofuranyl group, a furopyrrolyl group, a pyridoxazinyl group, and a dithienopyrrole group.

The "alkyl group" is defined by a functional group derived from linear or branched saturated hydrocarbons.

Specific examples of the alkyl group may include a methyl group, an ethyl group, a n-propyl group, an isopropyl group, a n-butyl group, a sec-butyl group, a t-butyl group, a n-pentyl group, a 1,1-dimethylpropyl group, a 1,2-dimethylpropyl group, a 2,2-dimethylpropyl group, a 1-ethylpropyl group, a 2-ethylpropyl group, a n-hexyl group, a 1-methyl-2-ethylpropyl group, a 1-ethyl-2-methylpropyl group, a 1,1,2-trimethylpropyl group, a 1-propylpropyl group, a 1-methylbutyl group, a 2-methylbutyl group, a 1,1-dimethylbutyl group, a 1,2-dimethylbutyl group, a 2,2-dimethylbutyl group, a 1,3-dimethylbutyl group, a 2,3-dimethylbutyl group, a 2-ethylbutyl group, a 2-methylpentyl group, a 3-methylpentyl group, and the like.

Further, the "arylene group" is defined by a divalent substituent group derived from the aforementioned aryl group.

Further, the "heteroarylene group" is defined by a divalent substituent group derived from the aforementioned heteroaryl group.

As one example, the compound represented by Chemical Formula 1 may include a compound represented by the following Chemical Formula 4.

[Chemical Formula 4]

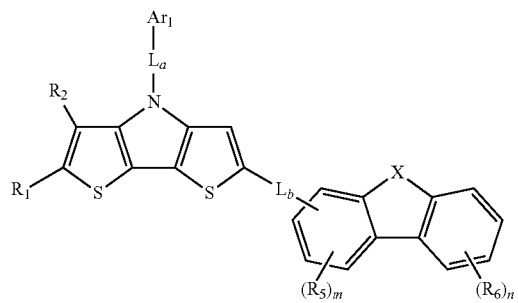

In Chemical Formula 4,

X represents O, S, N-$L_d$-$AR_3$, or Si($R_{10}$)($R_{11}$), $R_1$ and $R_2$ each independently represent hydrogen, an aryl group having 6 to 30 carbon atoms, a heteroaryl group having 2 to 30 carbon atoms, an alkenyl group having 2 to 30 carbon atoms, or an alkynyl group having 2 to 30 carbon atoms, $R_5$, $R_6$, $R_{10}$, and $R_{11}$ each independently represent hydrogen, an alkyl group having 1 to 10 carbon atoms, an alkenyl group having 2 to 30 carbon atoms, an alkynyl group having 2 to 30 carbon atoms, a cycloalkyl group having 3 to 30 carbon atoms, a heterocycloalkyl group having 2 to 30 carbon atoms, an aryl group having 6 to 30 carbon atoms, or a heteroaryl group having 2 to 30 carbon atoms, m represents an integer of 0 to 3, and n represents an integer of 0 to 4, $L_a$, $L_b$, and $L_d$ each independently represent a single bond, an arylene group having 6 to 30 carbon atoms, or a heteroarylene group having 2 to 30 carbon atoms, and $Ar_1$ and $Ar_3$ may each independently represent hydrogen, an alkyl group having 1 to 30 carbon atoms, an aryl group having 6 to 30 carbon atoms, a heteroaryl group having 2 to 30 carbon atoms, a cycloalkyl group having 3 to 30 carbon atoms, or a heterocycloalkyl group having 2 to 30 carbon atoms.

In this case, one or more of hydrogens of $R_1$, $R_2$, $R_5$, $R_6$, $L_a$, $L_b$, X, and $Ar_1$ of Chemical Formula 4 may be each independently unsubstituted or substituted by one or more substituent groups selected from the group consisting of an alkyl group having 1 to 6 carbon atoms, an alkenyl group having 2 to 6 carbon atoms, an alkoxy group having 1 to 6 carbon atoms, an aryl group having 6 to 30 carbon atoms, a heteroaryl group having 2 to 30 carbon atoms, an aryloxy group having 6 to 30 carbon atoms, an arylthio group having 6 to 30 carbon atoms, an alkoxycarbonyl group having 1 to 6 carbon atoms, a halogen group, a cyano group, a nitro group, a hydroxyl group, and a carboxyl group.

For example, in Chemical Formula 4, $R_1$, $R_2$, $Ar_1$, and $Ar_3$ may be each independently selected from structures of the following Table 1.

TABLE 1

| No. | Structure of substituent group |
|---|---|
| 1 | *—H |
| 2 | (phenyl) |
| 3 | (biphenyl) |
| 4 | (terphenyl) |
| 5 | (N-phenyl carbazole) |
| 6 | (9,9-dimethylfluorene) |

TABLE 1-continued

| No. | Structure of substituent group |
|---|---|
| 7 | (9,9-diphenylfluorene) |
| 8 | (dibenzofuran) |
| 9 | (dibenzothiophene) |

For example, substituent group 5 of Table 1 may be specifically represented by the following Chemical Formula 1-5a or the following Chemical Formula 1-5b.

[Chemical Formula 1-5a]

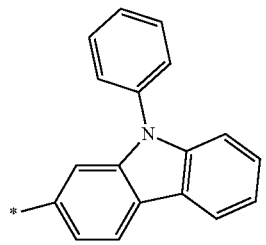

[Chemical Formula 1-5b]

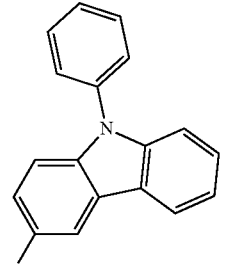

Further, substituent group 8 of Table 1 may be represented by the following Chemical Formula 1-8a or the following Chemical Formula 1-8b.

[Chemical Formula 1-8a]

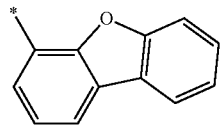

-continued

[Chemical Formula 1-8b]

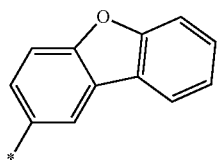

Further, substituent group 9 of Table 1 may be represented by the following Chemical Formula 1-9a or the following Chemical Formula 1-9b.

[Chemical Formula 1-9a]

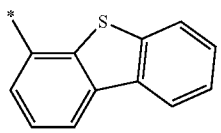

[Chemical Formula 1-9b]

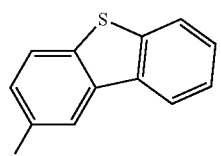

Hereinafter, since substituent groups 5, 8, and 9 of Table 1 are represented to be substantially the same as those described in the above, an overlapping specific description will be omitted.

Further, in Chemical Formula 4, $L_a$, $L_b$, and $L_d$ may be each independently selected from a single bond or structures of the following Table 2.

TABLE 2

| No. | Structure of substituent group |
|---|---|
| 1 | 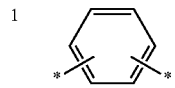 |
| 2 |  |
| 3 |  |
| 4 |  |
| 5 | 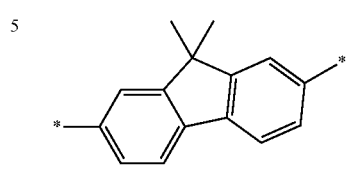 |

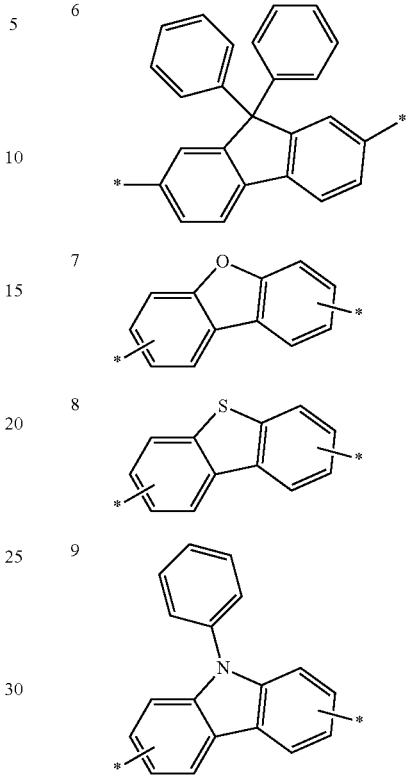

TABLE 2-continued

| No. | Structure of substituent group |
|---|---|
| 6 | |
| 7 | |
| 8 | |
| 9 | |

For example, in the case of each of substituent groups 2 to 4 of Table 2, all benzene rings that are adjacent to each other may be connected to para positions to have a straight line shape overall. Unlike this, a plurality of benzene rings may be connected to each other so as not to be limited to only the para position, and thus, overall, $L_a$, $L_b$, and $L_d$ of Chemical Formula 4 may each independently have a bent shape.

Substituent group 7 of Table 2 may be represented by the following Chemical Formula 2-7a or the following Chemical Formula 2-7b.

[Chemical Formula 2-7a]

[Chemical Formula 2-7b]

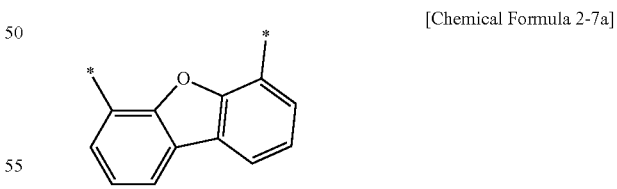

Further, substituent group 8 of Table 2 may be represented by the following Chemical Formula 2-8a or the following Chemical Formula 2-8b.

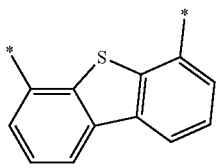
[Chemical Formula 2-8a]

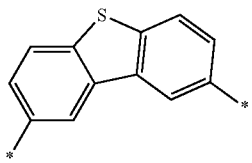
[Chemical Formula 2-8b]

Further, substituent group 9 of Table 2 may be represented by the following Chemical Formula 2-9a or the following Chemical Formula 2-9b.

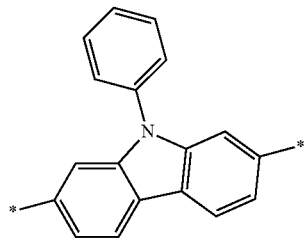
[Chemical Formula 2-9a]

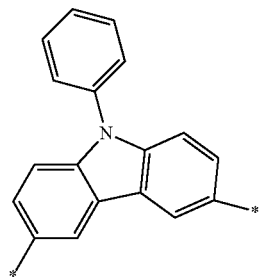
[Chemical Formula 2-9b]

Hereinafter, since substituent groups 7, 8, and 9 of Table 2 may be substantially the same as those described in the above, a specific description of an overlapping portion will be omitted.

As another example, the compound represented by Chemical Formula 1 may include a compound represented by the following Chemical Formula 5.

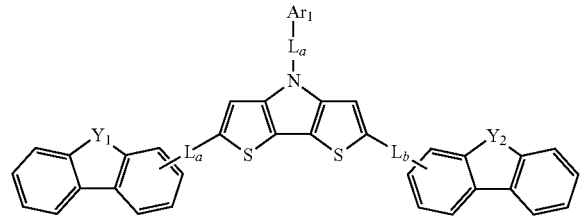
[Chemical Formula 5]

In Chemical Formula 5, $Y_1$ and $Y_2$ each independently represent O, S, N-$L_f$-$Ar_4$, or Si($R_{12}$)($R_{13}$), $L_a$, $L_b$, $L_e$, and $L_f$ each independently represent a single bond, an arylene group having 6 to 30 carbon atoms, or a heteroarylene group having 2 to 30 carbon atoms, $Ar_1$ and $Ar_4$ each independently represent hydrogen, an alkyl group having 1 to 30 carbon atoms, an aryl group having 6 to 30 carbon atoms, a heteroaryl group having 3 to 30 carbon atoms, a cycloalkyl group having 3 to 30 carbon atoms, or a heterocycloalkyl group having 2 to 30 carbon atoms, $R_{12}$ and $R_{13}$ each independently represent hydrogen, an alkyl group having 1 to 10 carbon atoms, an alkenyl group having 2 to 30 carbon atoms, an alkynyl group having 2 to 30 carbon atoms, a cycloalkyl group having 3 to 30 carbon atoms, a heterocycloalkyl group having 2 to 30 carbon atoms, an aryl group having 6 to 30 carbon atoms, or a heteroaryl group having 2 to 30 carbon atoms, and one or more of hydrogens of $Y_1$, $Y_2$, $L_a$, $L_b$, $L_e$, and $Ar_1$ of Chemical Formula 5 may be each independently unsubstituted or substituted by an alkyl group having 1 to 6 carbon atoms, an alkenyl group having 2 to 6 carbon atoms, an alkoxy group having 1 to 6 carbon atoms, an aryl group having 6 to 30 carbon atoms, a heteroaryl group having 2 to 30 carbon atoms, an aryloxy group having 6 to 30 carbon atoms, an arylthio group having 6 to 30 carbon atoms, an alkoxycarbonyl group having 1 to 6 carbon atoms, a halogen group, a cyano group, a nitro group, a hydroxyl group, or a carboxyl group.

As yet another example, the compound represented by Chemical Formula 1 may be represented by the following Chemical Formula 6.

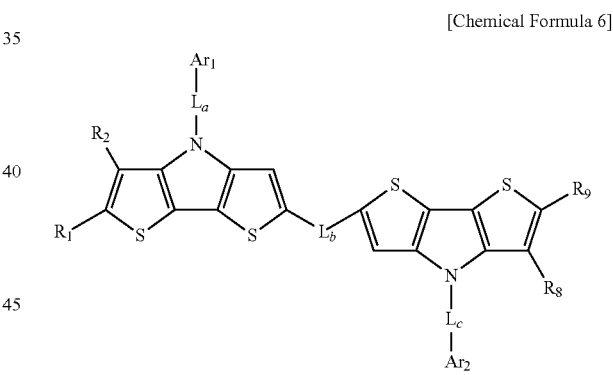
[Chemical Formula 6]

In Chemical Formula 6, $R_1$, $R_2$, $R_8$, and $R_9$ each independently represent hydrogen, an alkyl group having 1 to 10 carbon atoms, an alkenyl group having 2 to 30 carbon atoms, an alkynyl group having 2 to 30 carbon atoms, a cycloalkyl group having 3 to 30 carbon atoms, a heterocycloalkyl group having 2 to 30 carbon atoms, an aryl group having 6 to 30 carbon atoms, or a heteroaryl group having 2 to 30 carbon atoms, $L_a$ and $L_c$ each independently represent a single bond, an arylene group having 6 to 30 carbon atoms, or a heteroarylene group having 2 to 30 carbon atoms, $L_b$ represents *-$(L_1)_p$-$(L_2)_q$-$(L_3)_r$-$(L_4)_s$-*, $L_1$, $L_2$, $L_3$, and $L_4$ each independently represent a single bond, —O—, —S—, an arylene group having 6 to 30 carbon atoms, a heteroarylene group having 2 to 30 carbon atoms, an alkenylene group having 2 to 30 carbon atoms, an alkynylene group having 2 to 30 carbon atoms, or a cycloalkylene group having 3 to 30 carbon atoms, p, q, r, and s each independently represent an integer of 0 to 2, $Ar_1$ and $Ar^2$ each independently represent hydrogen, an alkyl group having 1 to 30 carbon atoms, an aryl group having 6 to 30 carbon atoms, a heteroaryl group having 2 to 30 carbon atoms, a cycloalkyl group having 3 to 30 carbon atoms, or a heterocycloalkyl group having 2 to 30 carbon atoms, and one or more of hydrogens of $R_1$, $R_2$, $R_8$, $R_9$, $L_a$, $L_b$, $L_c$, $Ar_1$, and $Ar_2$ of Chemical Formula 6 may be each independently unsubstituted or substituted by an alkyl group having 1 to 6 carbon atoms, an alkenyl group having 2 to 6 carbon atoms, an alkoxy group having 1 to 6 carbon atoms, an aryl group having 6 to 30 carbon atoms, a heteroaryl group having 2 to 30 carbon atoms, an aryloxy group having 6 to 30 carbon atoms, an arylthio group having 6 to 30 carbon atoms, an alkoxycarbonyl group having 1 to 6 carbon atoms, a halogen group, a cyano group, a nitro group, a hydroxyl group, or a carboxyl group.

For example, in Chemical Formula 6, $L_1$, $L_2$, $L_3$, and $L_4$ of $L_b$ may be each independently selected from a single bond or structures of the following Table 3.

TABLE 3

| No. | Structure of substituent group |
|-----|-------------------------------|
| 1 | (phenylene) |
| 2 | (biphenylene) |
| 3 | (terphenylene) |
| 4 | (quaterphenylene) |

TABLE 3-continued

| No. | Structure of substituent group |
|-----|-------------------------------|
| 5 | (9,9-dimethylfluorene) |
| 6 | (9,9-diphenylfluorene) |
| 7 | (dibenzofuran) |
| 8 | (dibenzothiophene) |
| 9 | (N-phenylcarbazole) |

In the exemplary embodiment, the compound represented by Chemical Formula 1 may be selected from structures of the following Table 4.

TABLE 4

| No. | Chemical Formula |
|-----|------------------|
| 1 | (structure) |

TABLE 4-continued
| No. | Chemical Formula |
|---|---|
| 2 | 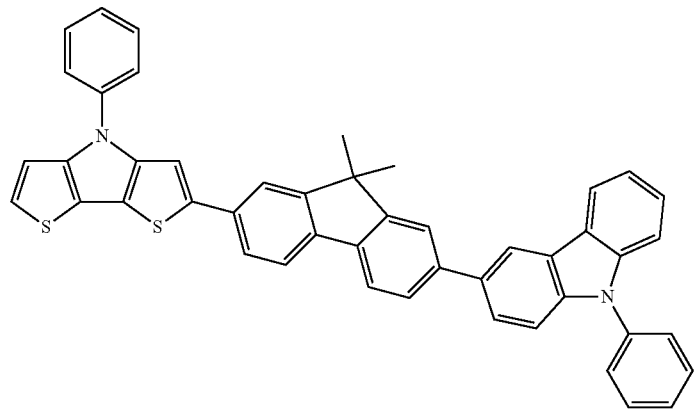 [SMILES: CC1(C)c2cc(-c3ccc4c(c3)c3ccccc3n4-c3ccccc3)ccc2-c2ccc(-c3cc4c(s3)c3sccc3n4-c3ccccc3)cc21] |
| 3 | 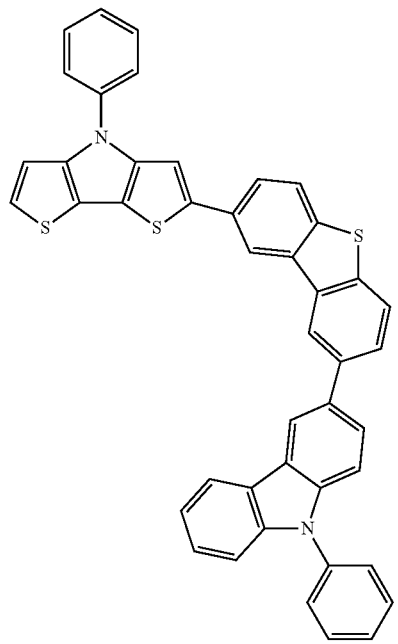 [SMILES: c1ccc(-n2c3ccccc3c3cc(-c4ccc5oc6ccc(-c7cc8c(s7)c7sccc7n8-c7ccccc7)cc6c5c4)ccc32)cc1] |

TABLE 4-continued
| No. | Chemical Formula |
|---|---|
| 4 | 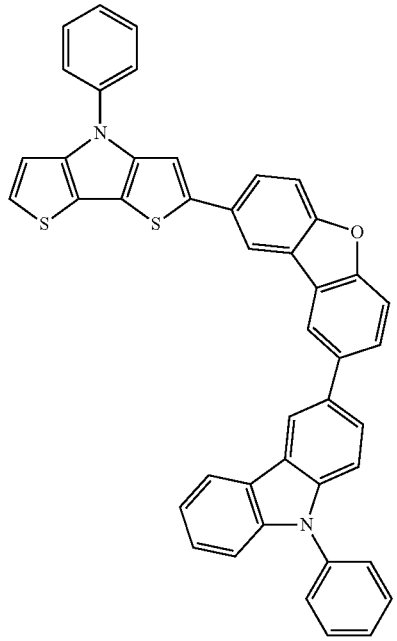 |
| 5 | 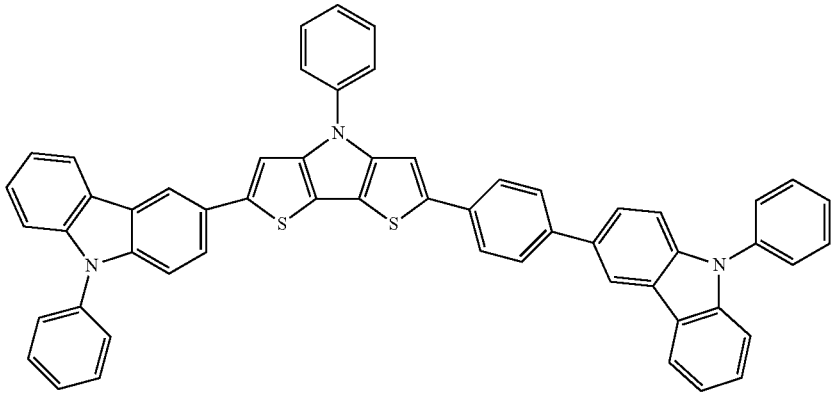 [SMILES: c1ccc(-n2c3ccccc3c3cc(-c4ccc(-c5cc6c(s5)c5sc(-c7ccc8c(c7)c7ccccc7n8-c7ccccc7)cc5n6-c5ccccc5)cc4)ccc32)cc1] |
| 6 | 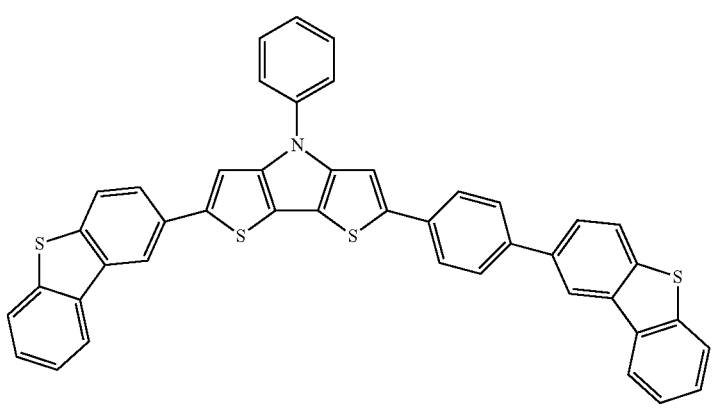 |

TABLE 4-continued
| No. | Chemical Formula |
|---|---|
| 7 | 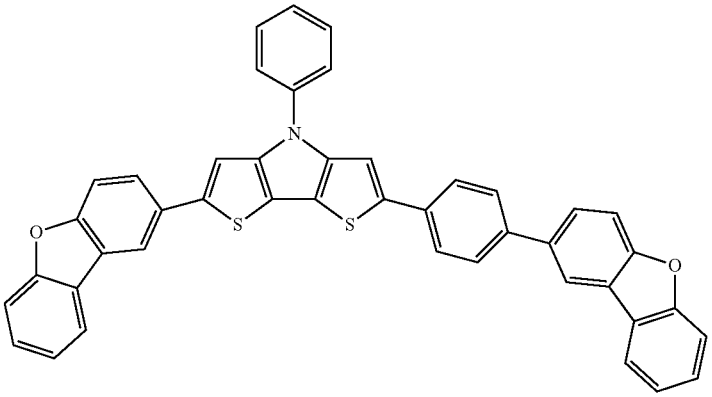 [SMILES: c1ccc(-n2c3cc(-c4ccc(-c5ccc6oc7ccccc7c6c5)cc4)sc3c3sc(-c4ccc5oc6ccccc6c5c4)cc32)cc1] |
| 8 | 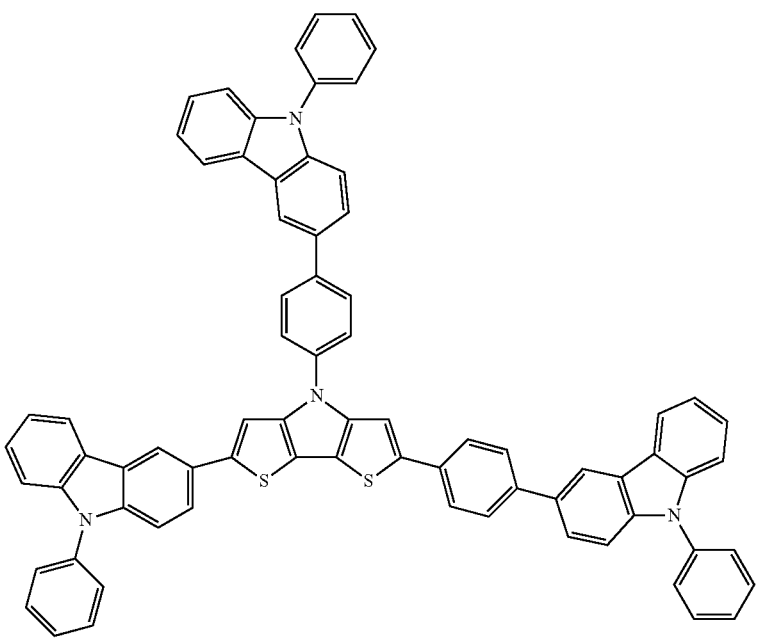 [SMILES: c1ccc(-n2c3ccccc3c3cc(-c4ccc(-c5cc6c(s5)c5sc(-c7ccc8c(c7)c7ccccc7n8-c7ccccc7)cc5n6-c5ccc(-c6ccc7c(c6)c6ccccc6n7-c6ccccc6)cc5)cc4)ccc32)cc1] |
| 9 | 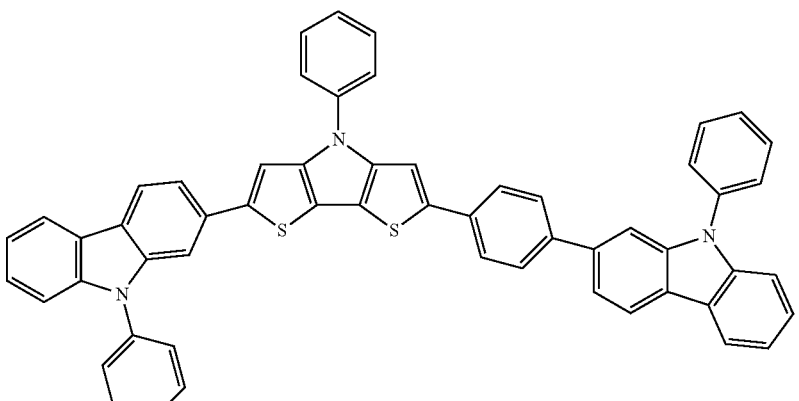 |

TABLE 4-continued
| No. | Chemical Formula |
| --- | --- |
| 10 | 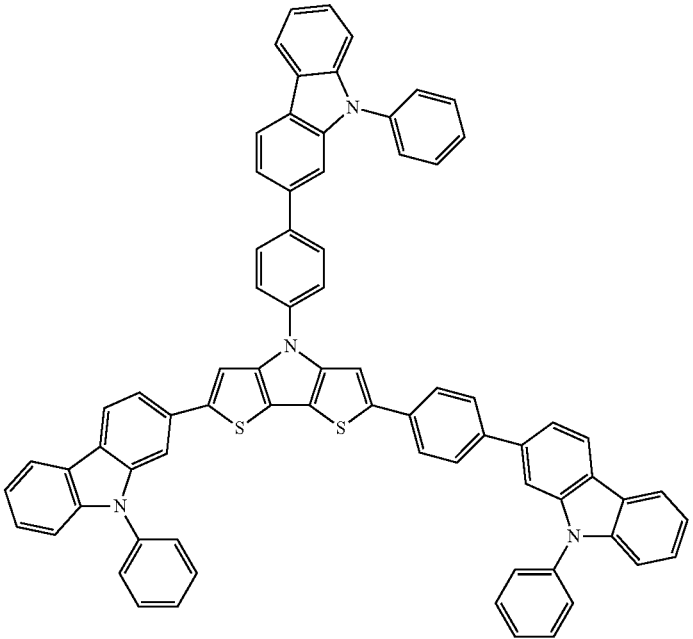 [SMILES: c1ccc(-n2c3ccccc3c3ccc(-c4ccc(-c5cc6c(s5)c5sc(-c7ccc8c9ccccc9n(-c9ccccc9)c8c7)cc5n6-c5ccc(-c6ccc7c8ccccc8n(-c8ccccc8)c7c6)cc5)cc4)cc32)cc1] |
| 11 | 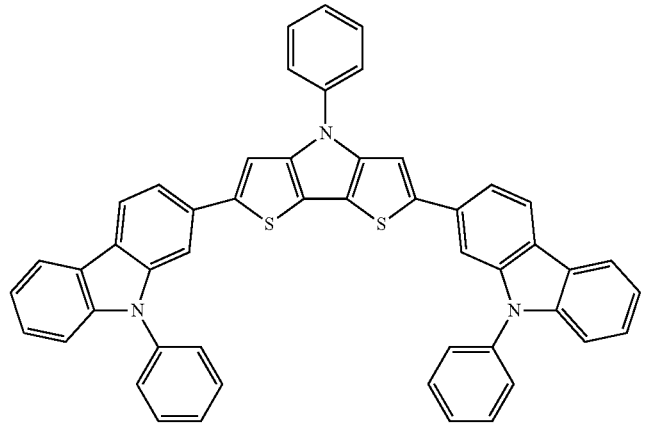 [SMILES: c1ccc(-n2c3ccccc3c3ccc(-c4cc5c(s4)c4sc(-c6ccc7c8ccccc8n(-c8ccccc8)c7c6)cc4n5-c4ccccc4)cc32)cc1] |
| 12 | 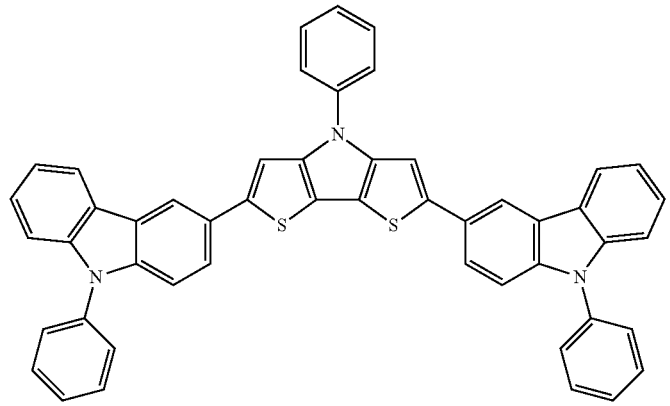 [SMILES: c1ccc(-n2c3ccccc3c3cc(-c4cc5c(s4)c4sc(-c6ccc7c(c6)c6ccccc6n7-c6ccccc6)cc4n5-c4ccccc4)ccc32)cc1] |

TABLE 4-continued
| No. | Chemical Formula |
|---|---|
| 13 | 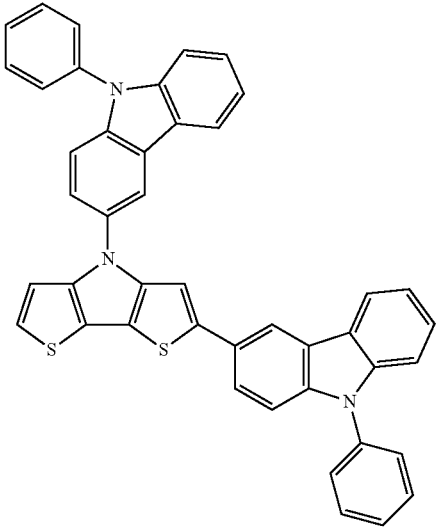 [SMILES: c1ccc(-n2c3ccccc3c3cc(-c4cc5c(s4)c4sccc4n5-c4ccc5c(c4)c4ccccc4n5-c4ccccc4)ccc32)cc1] |
| 14 | 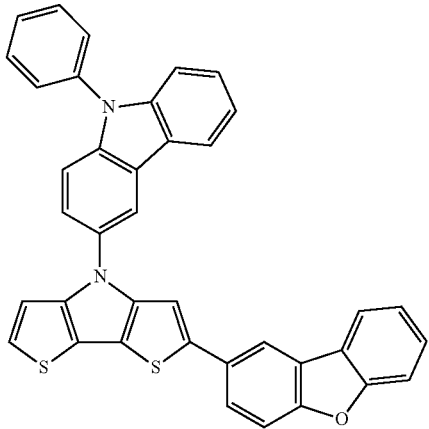 [SMILES: c1ccc(-n2c3ccccc3c3cc(-n4c5ccsc5c5sc(-c6ccc7oc8ccccc8c7c6)cc54)ccc32)cc1] |
| 15 | 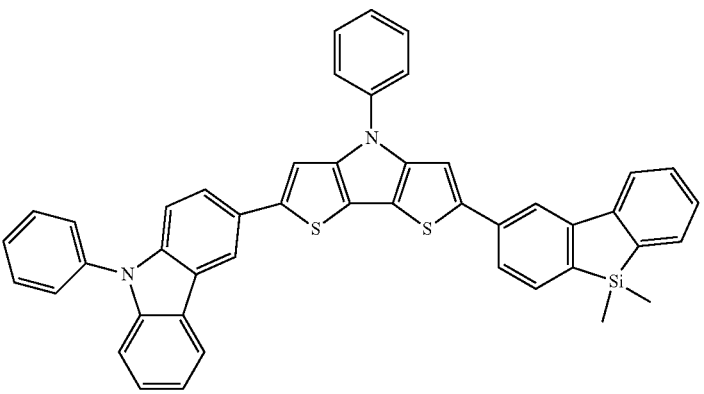 [SMILES: C[Si]1(C)c2ccccc2-c2cc(-c3cc4c(s3)c3sc(-c5ccc6c(c5)c5ccccc5n6-c5ccccc5)cc3n4-c3ccccc3)ccc21] |

TABLE 4-continued

| No. | Chemical Formula |
| --- | --- |
| 16 | |
| 17 | |
| 18 | |

TABLE 4-continued
| No. | Chemical Formula |
| --- | --- |
| 19 | 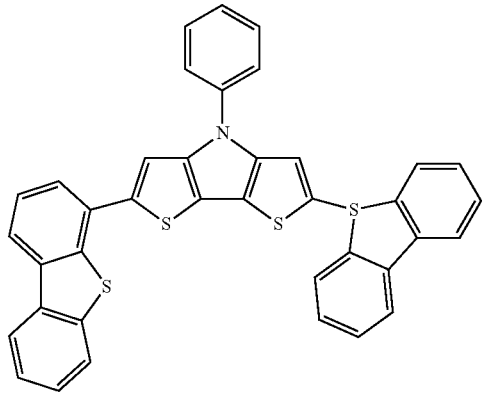 |
| 20 | 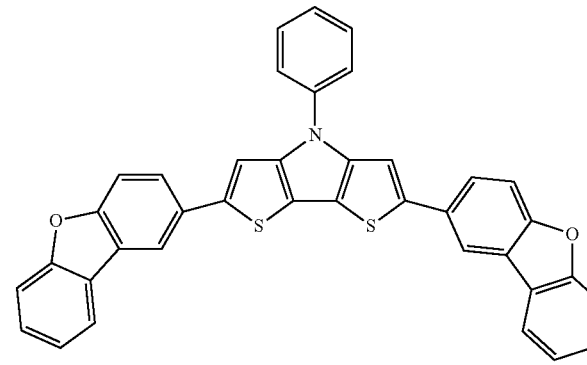 |
| 21 | 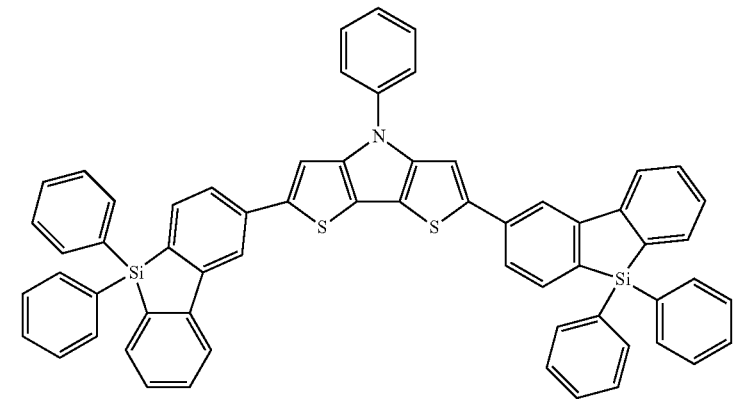 [SMILES: c1ccc(-n2c3cc(-c4ccc5c(c4)-c4ccccc4[Si]5(c4ccccc4)c4ccccc4)sc3c3sc(-c4ccc5c(c4)-c4ccccc4[Si]5(c4ccccc4)c4ccccc4)cc32)cc1] |

TABLE 4-continued

| No. | Chemical Formula |
|---|---|
| 22 | |
| 23 | |
| 24 | |

TABLE 4-continued
| No. | Chemical Formula |
|---|---|
| 25 | 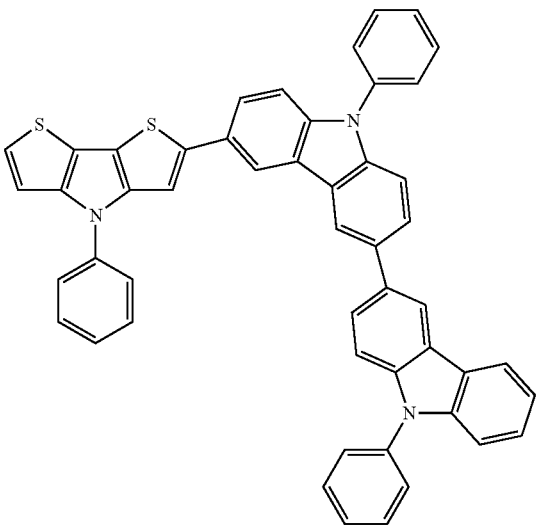 [SMILES: c1ccc(-n2c3ccccc3c3cc(-c4ccc5c(c4)c4cc(-c6cc7c(s6)c6sccc6n7-c6ccccc6)ccc4n5-c4ccccc4)ccc32)cc1] |
| 26 | 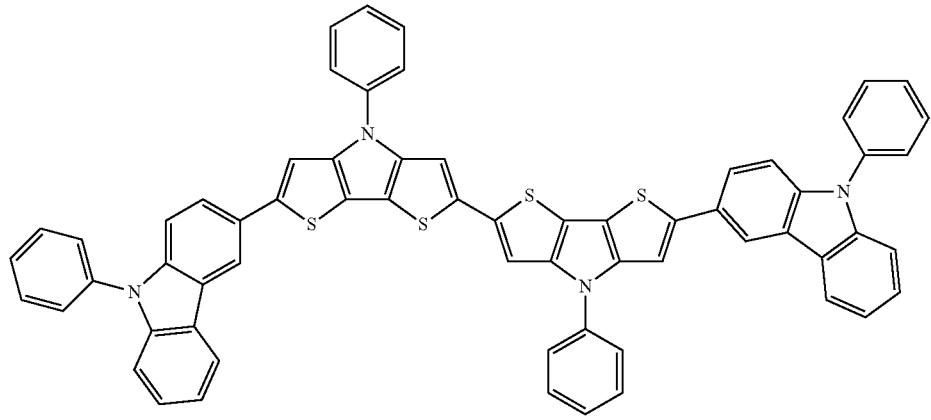 [SMILES: c1ccc(-n2c3ccccc3c3cc(-c4cc5c(s4)c4sc(-c6cc7c(s6)c6sc(-c8ccc9c(c8)c8ccccc8n9-c8ccccc8)cc6n7-c6ccccc6)cc4n5-c4ccccc4)ccc32)cc1] |
| 27 | 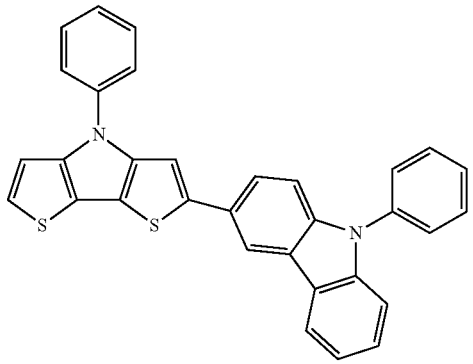 [SMILES: c1ccc(-n2c3ccccc3c3cc(-c4cc5c(s4)c4sccc4n5-c4ccccc4)ccc32)cc1] |

TABLE 4-continued
| No. | Chemical Formula |
|---|---|
| 28 | 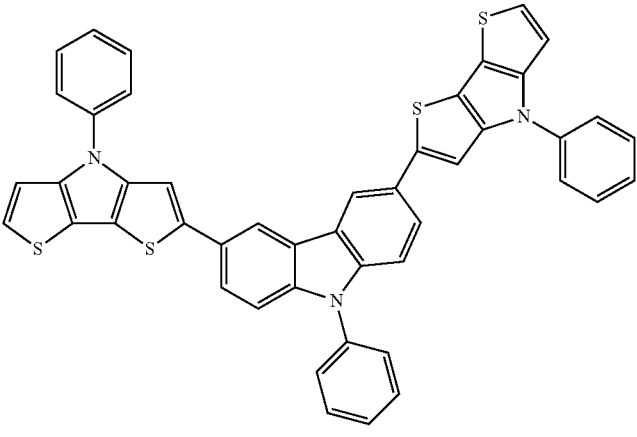 [SMILES: c1ccc(-n2c3ccc(-c4cc5c(s4)c4sccc4n5-c4ccccc4)cc3c3cc(-c4cc5c(s4)c4sccc4n5-c4ccccc4)ccc32)cc1] |
| 29 | 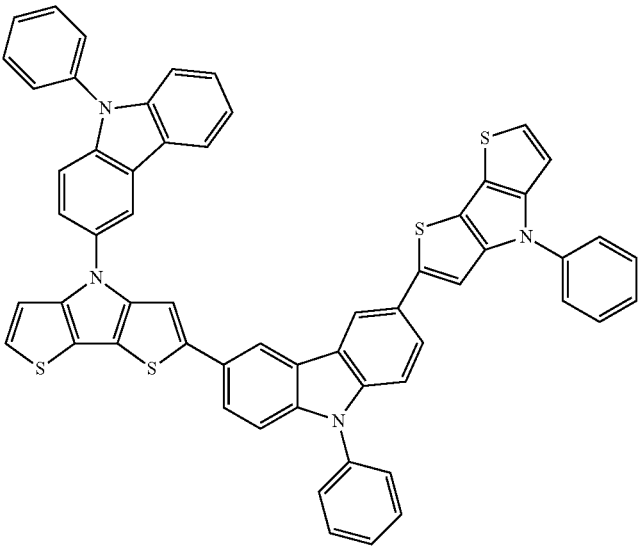 [SMILES: c1ccc(-n2c3ccc(-c4cc5c(s4)c4sccc4n5-c4ccccc4)cc3c3cc(-c4cc5c(s4)c4sccc4n5-c4ccc5c(c4)c4ccccc4n5-c4ccccc4)ccc32)cc1] |

TABLE 4-continued
| No. | Chemical Formula |
|---|---|
| 30 | 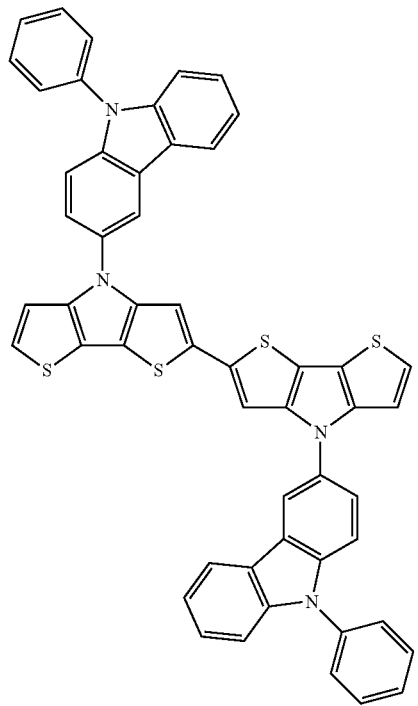 [SMILES: c1ccc(-n2c3ccccc3c3cc(-n4c5ccsc5c5sc(-c6cc7c(s6)c6sccc6n7-c6ccc7c(c6)c6ccccc6n7-c6ccccc6)cc54)ccc32)cc1] |
| 31 | 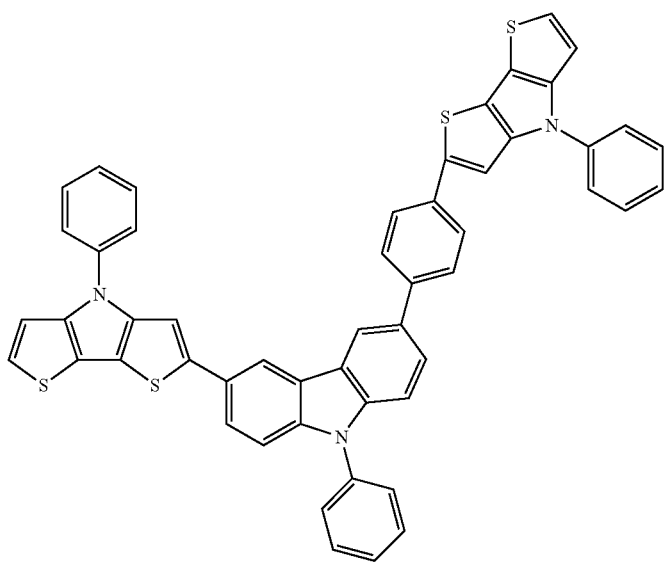 [SMILES: c1ccc(-n2c3ccc(-c4ccc(-c5cc6c(s5)c5sccc5n6-c5ccccc5)cc4)cc3c3cc(-c4cc5c(s4)c4sccc4n5-c4ccccc4)ccc32)cc1] |

TABLE 4-continued
| No. | Chemical Formula |
|---|---|
| 32 | 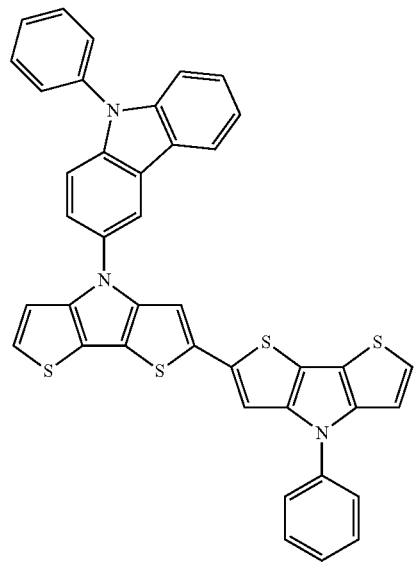 [SMILES: c1ccc(-n2c3ccccc3c3cc(-n4c5ccsc5c5sc(-c6cc7c(s6)c6sccc6n7-c6ccccc6)cc54)ccc32)cc1] |
| 33 | 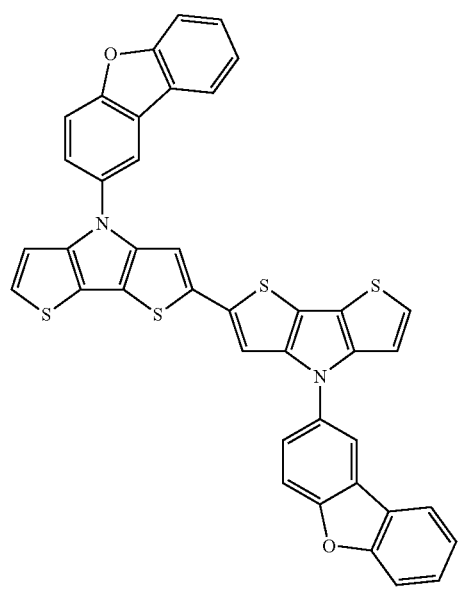 [SMILES: c1ccc2c(c1)oc1ccc(-n3c4ccsc4c4sc(-c5cc6c(s5)c5sccc5n6-c5ccc6oc7ccccc7c6c5)cc43)cc12] |

TABLE 4-continued

| No. | Chemical Formula |
| --- | --- |
| 34 | |
| 35 | |
| 36 | |

TABLE 4-continued

| No. | Chemical Formula |
|---|---|
| 37 | |
| 38 | |
| 39 | |

TABLE 4-continued

| No. | Chemical Formula |
|---|---|
| 40 | |
| 41 | |
| 42 | |

TABLE 4-continued
| No. | Chemical Formula |
|---|---|
| 43 | 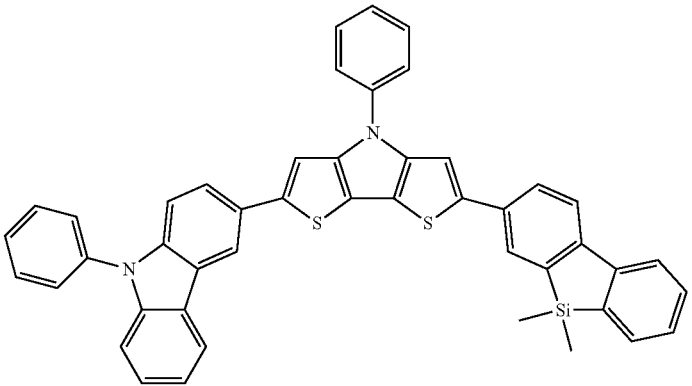 [SMILES: C[Si]1(C)c2ccccc2-c2ccc(-c3cc4c(s3)c3sc(-c5ccc6c(c5)c5ccccc5n6-c5ccccc5)cc3n4-c3ccccc3)cc21] |
| 44 | 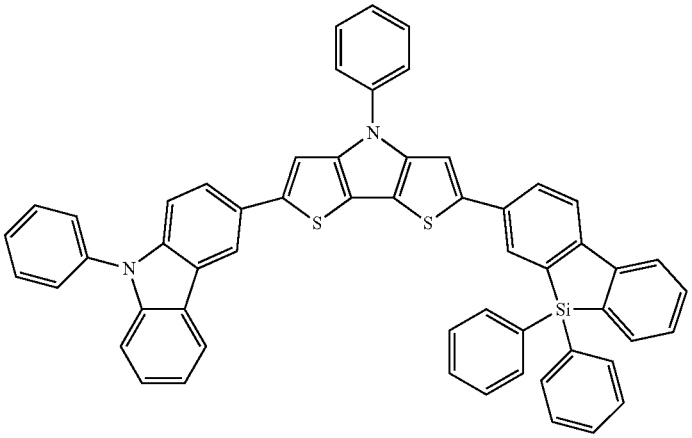 [SMILES: c1ccc(-n2c3ccccc3c3cc(-c4cc5c(s4)c4sc(-c6ccc7c(c6)[Si](c6ccccc6)(c6ccccc6)c6ccccc6-7)cc4n5-c4ccccc4)ccc32)cc1] |
| 45 | 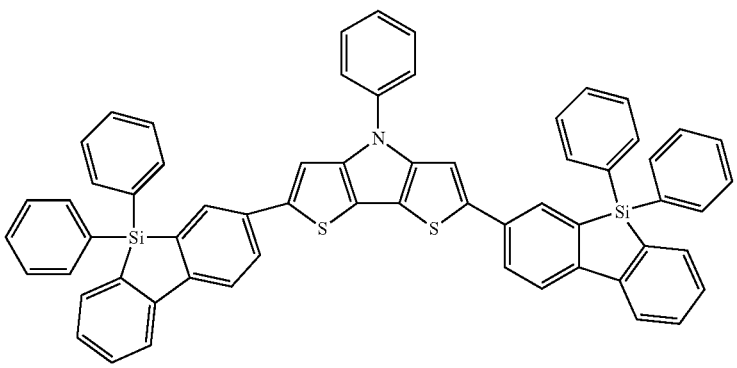 [SMILES: c1ccc(-n2c3cc(-c4ccc5c(c4)[Si](c4ccccc4)(c4ccccc4)c4ccccc4-5)sc3c3sc(-c4ccc5c(c4)[Si](c4ccccc4)(c4ccccc4)c4ccccc4-5)cc32)cc1] |

TABLE 4-continued

| No. | Chemical Formula |
| --- | --- |
| 46 | |
| 47 | |
| 48 | |

TABLE 4-continued
| No. | Chemical Formula |
| --- | --- |
| 49 | 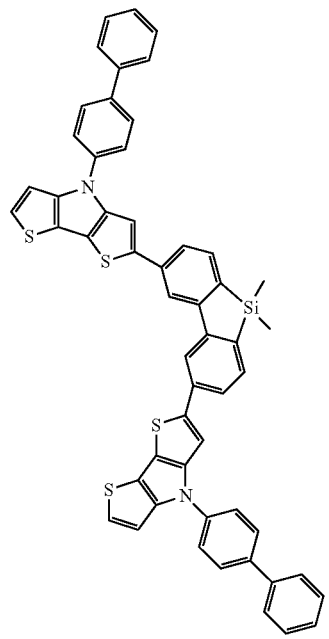 [SMILES: C[Si]1(C)c2ccc(-c3cc4c(s3)c3sccc3n4-c3ccc(-c4ccccc4)cc3)cc2-c2cc(-c3cc4c(s3)c3sccc3n4-c3ccc(-c4ccccc4)cc3)ccc21] |
| 50 | 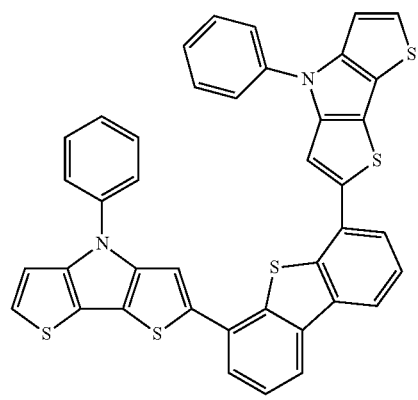 [SMILES: c1ccc(-n2c3ccsc3c3sc(-c4cccc5c4sc4c(-c6cc7c(s6)c6sccc6n7-c6ccccc6)cccc45)cc32)cc1] |

TABLE 4-continued
| No. | Chemical Formula |
|---|---|
| 51 | 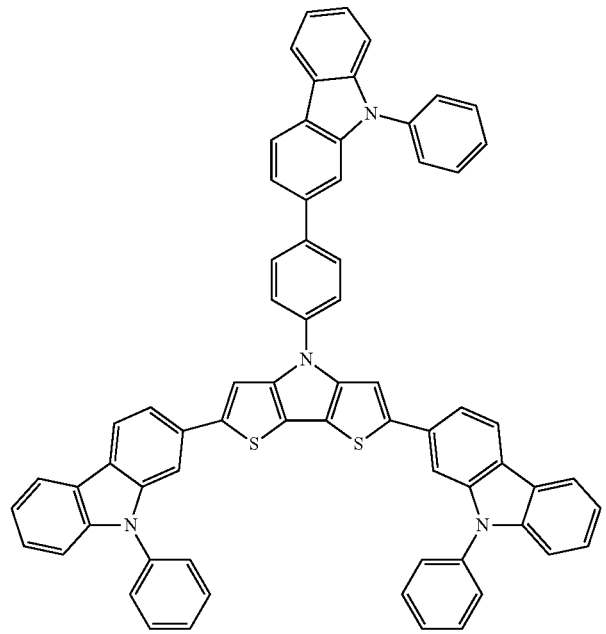 [SMILES: c1ccc(-n2c3ccccc3c3ccc(-c4ccc(-n5c6cc(-c7ccc8c9ccccc9n(-c9ccccc9)c8c7)sc6c6sc(-c7ccc8c9ccccc9n(-c9ccccc9)c8c7)cc65)cc4)cc32)cc1] |
| 52 | 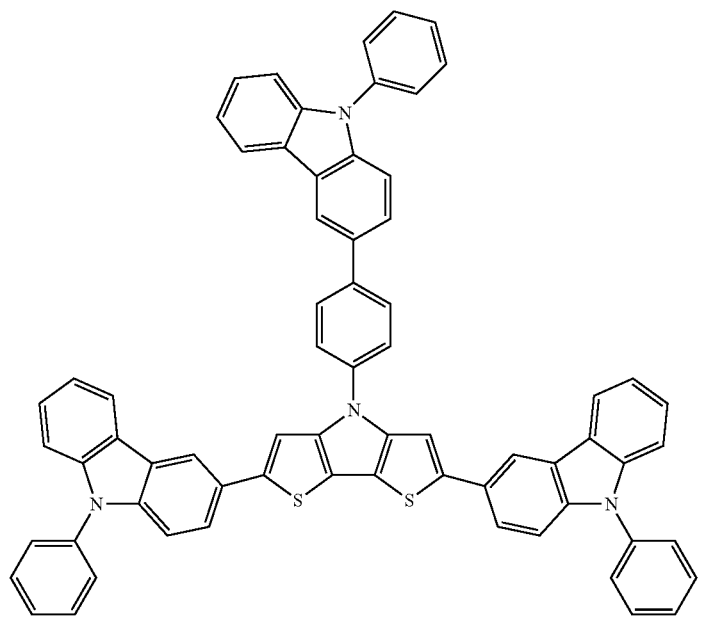 [SMILES: c1ccc(-n2c3ccccc3c3cc(-c4ccc(-n5c6cc(-c7ccc8c(c7)c7ccccc7n8-c7ccccc7)sc6c6sc(-c7ccc8c(c7)c7ccccc7n8-c7ccccc7)cc65)cc4)ccc32)cc1] |

TABLE 4-continued
| No. | Chemical Formula |
|---|---|
| 53 | 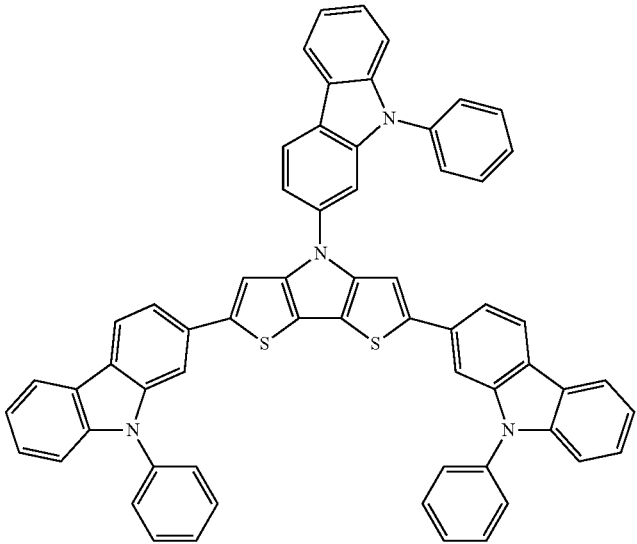 [SMILES: c1ccc(-n2c3ccccc3c3ccc(-c4cc5c(s4)c4sc(-c6ccc7c8ccccc8n(-c8ccccc8)c7c6)cc4n5-c4ccc5c6ccccc6n(-c6ccccc6)c5c4)cc32)cc1] |
| 54 | 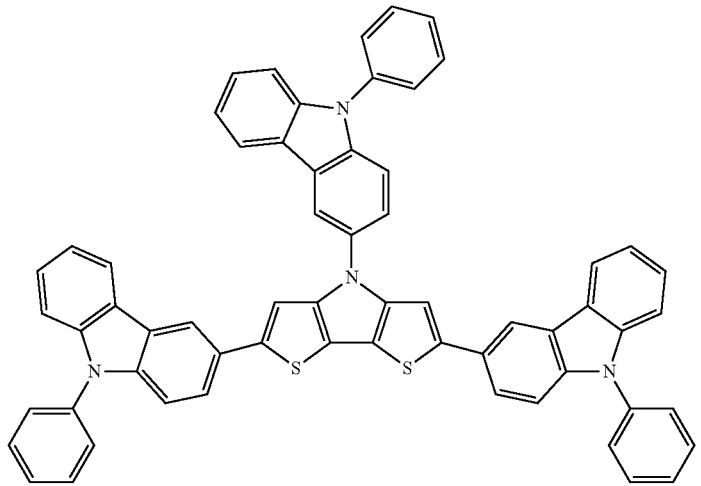 [SMILES: c1ccc(-n2c3ccccc3c3cc(-c4cc5c(s4)c4sc(-c6ccc7c(c6)c6ccccc6n7-c6ccccc6)cc4n5-c4ccc5c(c4)c4ccccc4n5-c4ccccc4)ccc32)cc1] |
| 55 | 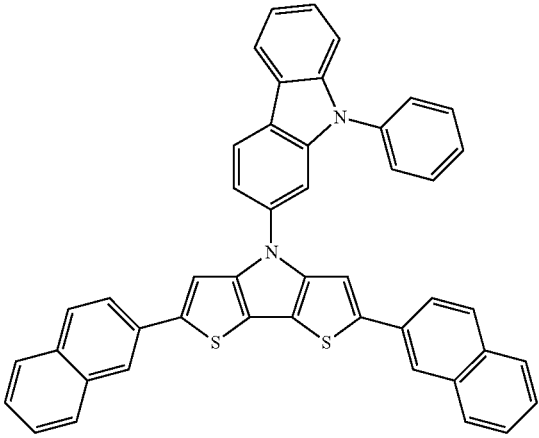 [SMILES: c1ccc(-n2c3ccccc3c3ccc(-n4c5cc(-c6ccc7ccccc7c6)sc5c5sc(-c6ccc7ccccc7c6)cc54)cc32)cc1] |

TABLE 4-continued
| No. | Chemical Formula |
| --- | --- |
| 56 | 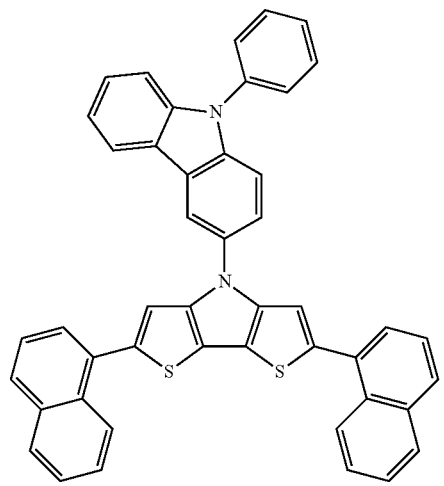 [SMILES: c1ccc(-n2c3ccccc3c3cc(-n4c5cc(-c6cccc7ccccc67)sc5c5sc(-c6cccc7ccccc67)cc54)ccc32)cc1] |
| 57 | 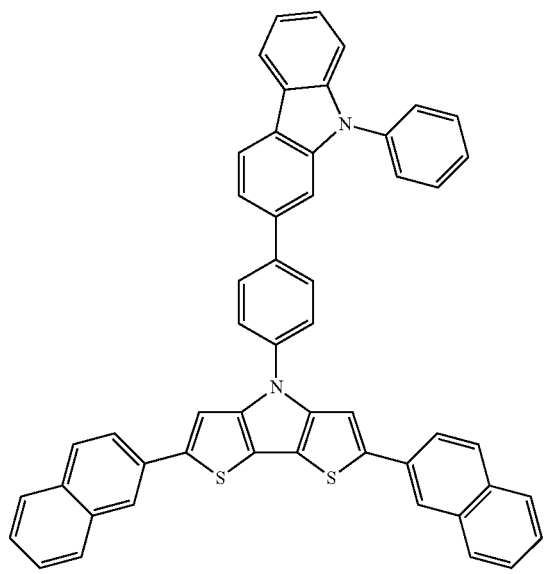 [SMILES: c1ccc(-n2c3ccccc3c3ccc(-c4ccc(-n5c6cc(-c7ccc8ccccc8c7)sc6c6sc(-c7ccc8ccccc8c7)cc65)cc4)cc32)cc1] |

TABLE 4-continued
| No. | Chemical Formula |
| --- | --- |
| 58 | 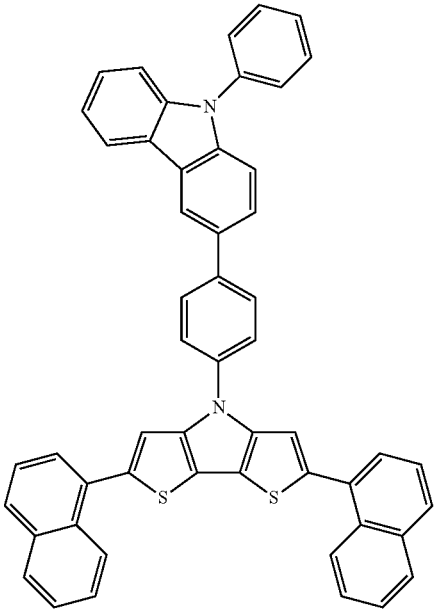 [SMILES: c1ccc(-n2c3ccccc3c3cc(-c4ccc(-n5c6cc(-c7cccc8ccccc78)sc6c6sc(-c7cccc8ccccc78)cc65)cc4)ccc32)cc1] |
| 59 | 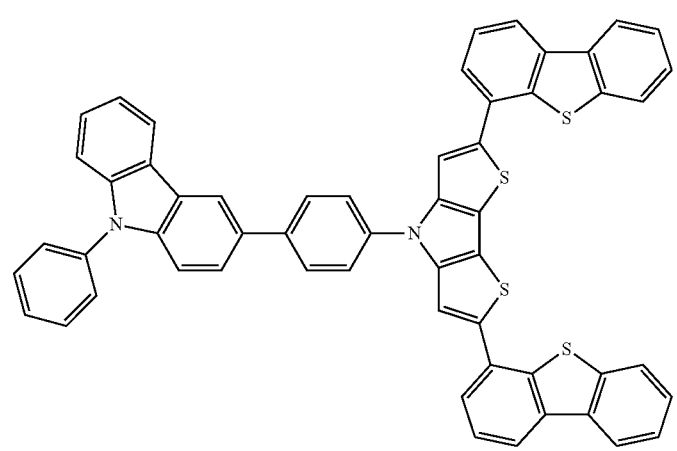 [SMILES: c1ccc(-n2c3ccccc3c3cc(-c4ccc(-n5c6cc(-c7cccc8c7sc7ccccc78)sc6c6sc(-c7cccc8c7sc7ccccc78)cc65)cc4)ccc32)cc1] |
| 60 | 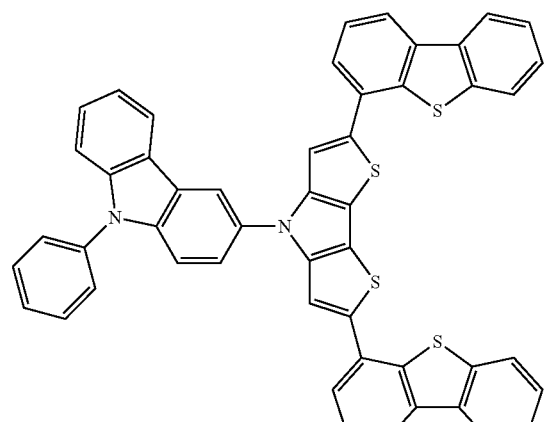 |

TABLE 4-continued

| No. | Chemical Formula |
| --- | --- |
| 61 | |
| 62 | |
| 63 | |

TABLE 4-continued
| No. | Chemical Formula |
| --- | --- |
| 64 | 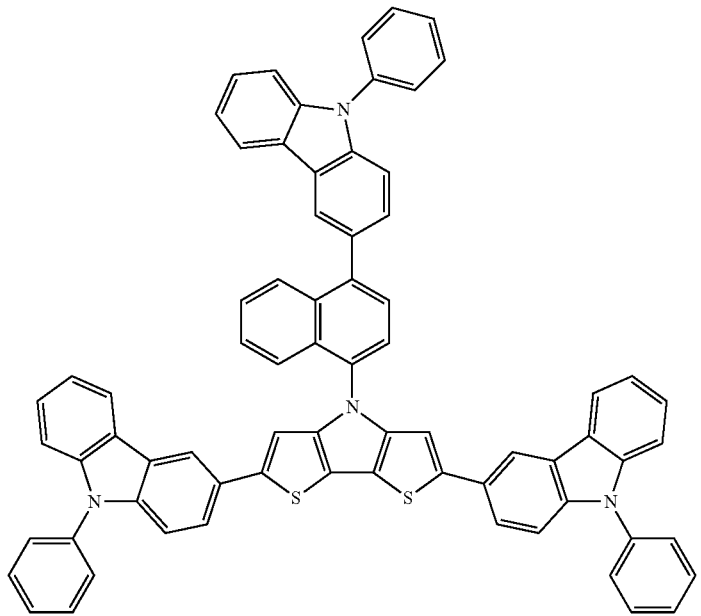 [SMILES: c1ccc(-n2c3ccccc3c3cc(-c4cc5c(s4)c4sc(-c6ccc7c(c6)c6ccccc6n7-c6ccccc6)cc4n5-c4ccc(-c5ccc6c(c5)c5ccccc5n6-c5ccccc5)c5ccccc45)ccc32)cc1] |
| 65 | 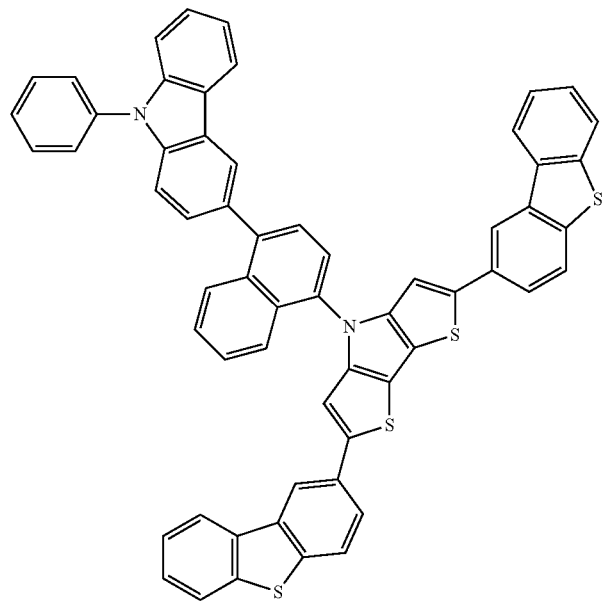 [SMILES: c1ccc(-n2c3ccccc3c3cc(-c4ccc(-n5c6cc(-c7ccc8sc9ccccc9c8c7)sc6c6sc(-c7ccc8sc9ccccc9c8c7)cc65)c5ccccc45)ccc32)cc1] |

TABLE 4-continued

| No. | Chemical Formula |
|---|---|
| 66 | 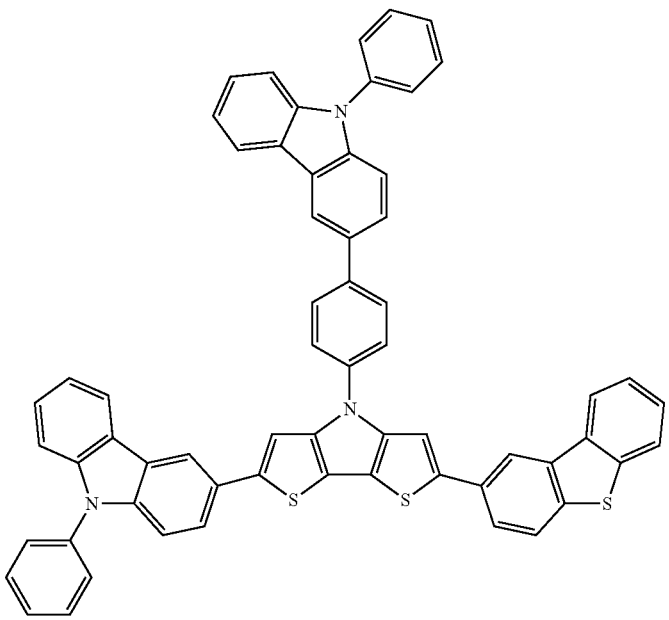 [SMILES: c1ccc(-n2c3ccccc3c3cc(-c4ccc(-n5c6cc(-c7ccc8sc9ccccc9c8c7)sc6c6sc(-c7ccc8c(c7)c7ccccc7n8-c7ccccc7)cc65)cc4)ccc32)cc1] |

Hereinafter, a light-emitting element including the novel compound according to the present invention will be described with reference to the accompanying drawings. The structure of the light-emitting element including the compound is not limited by the accompanying drawings and the following description.

FIG. 1 is a cross-sectional view for illustrating the light-emitting element according to the exemplary embodiment of the present invention.

Referring to FIG. 1, a light-emitting element 100 includes a first electrode 20, a hole transportable layer 30, a light emitting layer 40, and a second electrode 50 formed on a base substrate 10. The light-emitting element 100 may be an organic light emitting diode (OLED).

The first electrode 20 may be formed of a conductive material on the base substrate 10. For example, the first electrode 20 may be a transparent electrode. In this case, the first electrode 20 may be formed of indium-tin oxide (ITO). Unlike this, the first electrode 20 may be an opaque (reflective) electrode. In this case, the first electrode 20 may have an ITO/silver (Ag)/ITO structure. The first electrode 20 may become an anode of the light-emitting element 100.

The hole transportable layer 30 is formed on the first electrode 20 to be interposed between the first electrode 20 and the light emitting layer 40. The hole transportable layer 30 includes a compound represented by the following Chemical Formula 1 as a hole transportable compound.

[Chemical Formula 1]

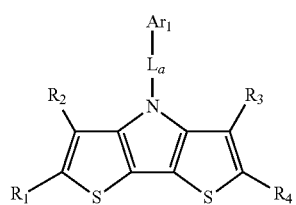

The compound represented by Chemical Formula 1 is the novel compound according to the present invention, and is substantially the same as that described in the above. Accordingly, a specific description of each of $R_1$ to $R_4$, $L_a$, and $Ar_1$ will be omitted.

A wavelength of light emitted from the light emitting layer 40 may be changed according to a kind of the compound forming the light emitting layer 40.

The second electrode 50 may be formed of a conductive material on the light emitting layer 40. In the case where the first electrode 20 is a transparent electrode, the second electrode 50 may be an opaque (reflective) electrode. In this case, the second electrode 50 may be an aluminum electrode. Unlike this, in the case where the first electrode 20 is an opaque electrode, the second electrode 50 may be a transparent or translucent electrode. In this case, the second electrode 50 may have a thickness of 100 Å to 150 Å, and may be made of an alloy including magnesium and silver. The second electrode 50 may become a cathode of the light-emitting element 100.

Between the light emitting layer 40 and the second electrode 50, as an electron transportable layer, an electron transport layer and/or an electron injection layer may be formed.

In the case where a current flows between the first and second electrodes 20 and 50 of the light-emitting element 100, holes injected from the first electrode 20 to the light emitting layer 40 and electrons injected from the second electrode 50 to the light emitting layer 40 are combined to form excitons. In a process of transferring the exciton to a bottom state, light having a wavelength of a specific region band is generated. In this case, the exciton may be a singlet exciton or a triplet exciton. Accordingly, the light-emitting element 100 may provide light to the outside.

Although not illustrated in the drawings, the light-emitting element 100 may further include an electron transport layer (ETL) and an electron injection layer (EIL) disposed between the light emitting layer 40 and the second electrode 50. The electron transport layer and the electron injection layer may be sequentially laminated to be formed on the light emitting layer 40.

Further, the light-emitting element 100 may further include a first blocking layer (not illustrated) disposed between the first electrode 20 and the light emitting layer 40, and/or a second blocking layer (not illustrated) disposed between the light emitting layer 40 and the second electrode 50.

For example, the first blocking layer may be an electron blocking layer (EBL) disposed between the hole transportable layer 30 and the light emitting layer 40 to prevent the electrons injected from the second electrode 50 from flowing through the light emitting layer 40 into the hole transportable layer 30. Further, the first blocking layer may be an exciton blocking layer preventing the exciton formed in the light emitting layer 40 from being diffused in a direction of the first electrode 20 to become extinct without light emission.

In this case, the first blocking layer may include the aforementioned compound according to the present invention.

The second blocking layer may be a hole blocking layer (HBL) disposed between the light emitting layer 40 and the second electrode 50 and specifically between the light emitting layer 40 and the electron transport layer to prevent the holes from flowing from the first electrode 20 through the light emitting layer 40 into the electron transport layer. Further, the second blocking layer may be an exciton blocking layer preventing the exciton formed in the light emitting layer 40 from being diffused in a direction of the second electrode 50 to become extinct without light emission.

If a thickness of each of the first and second blocking layers is adjusted to match a resonance length of the light-emitting element 100, light emitting efficiency may be increased, and the thickness may be adjusted so that the exciton is formed at the center of the light emitting layer 40.

Referring to FIG. 2, a light-emitting element 102 includes a first electrode 20, a hole transportable layer 32, a light emitting layer 40, and a second electrode 50 formed on a base substrate 10. Since the light-emitting element is substantially the same as that illustrated in FIG. 1 with the exception of the hole transportable layer 32, an overlapping description will be omitted.

The hole transportable layer 32 includes the compound represented by Chemical Formula 1, and a P-type dopant. Since the compound included in the hole transportable layer 32 is substantially the same as that described in the above, an overlapping specific description will be omitted.

The P-type dopant may include a P-type organic dopant, and/or a P-type inorganic dopant.

Specific examples of the P-type organic dopant may include compounds represented by the following Chemical Formulas 7 to 11, hexadecafluorophthalocyanine (F16CuPc), 11,11,12,12-tetracyanonaphtho-2,6-quinodimethane (TNAP), 3,6-difluoro-2,5,7,7,8,8-hexacyano-quinodimethane (F2-HCNQ), tetracyanoquinodimethane (TCNQ), or the like. The examples may be used alone or in combination of two or more thereof.

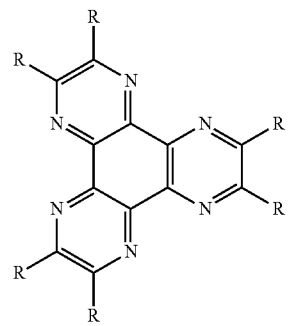

[Chemical Formula 7]

In Chemical Formula 7, R may represent a cyano group, a sulfone group, a sulfoxide group, a sulfonamide group, a sulfonate group, a nitro group, or a trifluoromethyl group.

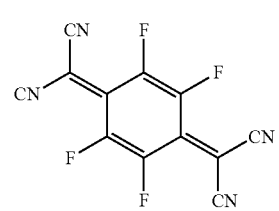

[Chemical Formula 8]

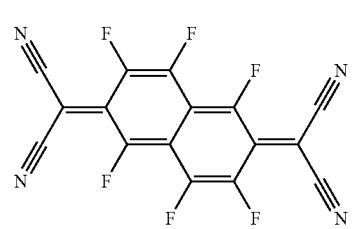

[Chemical Formula 9]

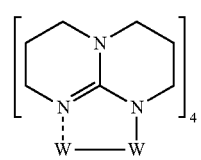

[Chemical Formula 10]

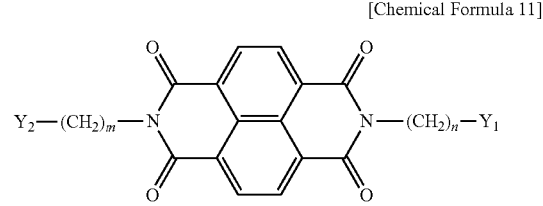

[Chemical Formula 11]

In Chemical Formula 11, m and n may each independently represent an integer of 1 to 5, and $Y_1$ and $Y_2$ may each independently represent an aryl group having 6 to 20 carbon atoms or a heteroaryl group having 2 to 20 carbon atoms. In this case, hydrogen of the aryl group or the heteroaryl group represented by $Y_1$ and $Y_2$ may be unsubstituted or substituted by an alkyl group having 1 to 5 carbon atoms, an alkoxy group having 1 to 5 carbon atoms, or a hydroxyl group, and hydrogens of substituted or unsubstituted $Y_1$ and $Y_2$ may be each independently unsubstituted or substituted by a halogen group.

For example, the compound represented by Chemical Formula 11 may include a compound represented by the following Chemical Formula 11a or the following Chemical Formula 11b.

[Chemical Formula 11a]

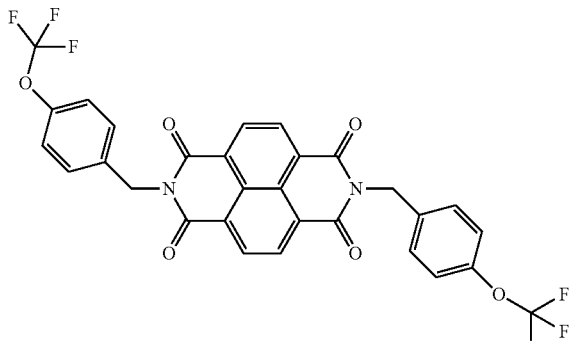

[Chemical Formula 11b]

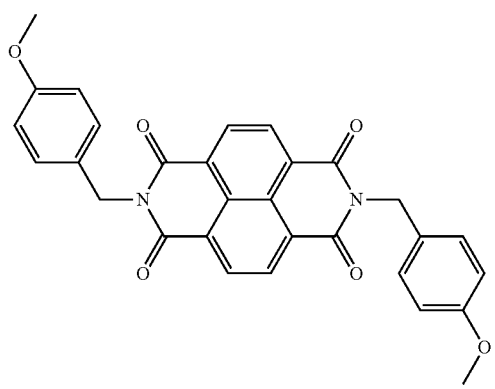

Examples of the P-type inorganic dopant may include metal oxides, metal halides, or the like. Specific examples of the P-type inorganic dopant may include $MoO_3$, $V_2O_5$, $WO_3$, $SnO_2$, $ZnO$, $MnO_2$, $CoO_2$, $ReO_3$, $TiO_2$, $FeCl_3$, $SbCl_5$, $MgF_2$, or the like. The examples may be used alone or in combination of two or more thereof.

A content of the P-type dopant may be about 0.5 parts by weight to about 20 parts by weight based on 100 parts by weight of the novel compound according to the present invention, which is a hole transportable compound. For example, the content of the P-type dopant may be about 0.5 parts by weight to about 15 parts by weight or about 0.5 parts by weight to about 5 parts by weight based on 100 parts by weight of the hole transportable compound. Unlike this, the content of the P-type dopant may be about 1 part by weight to 10 parts by weight, 1 part by weight to 5 parts by weight, 1.5 parts by weight to 6 parts by weight, or 2 parts by weight to 5 parts by weight based on 100 parts by weight of the hole transportable compound.

In the case where the content of the P-type dopant is about 0.5 parts by weight to about 20 parts by weight based on 100 parts by weight of the hole transportable compound, the P-type dopant may not degrade physical properties of the hole transportable compound and may prevent generation of an excessive leakage current. Further, energy barriers at interfaces with upper and lower layers coming into contact with the hole transportable layer 32 may be reduced by the P-type dopant.

Although not illustrated in the drawings, the light-emitting element 102 may further include the electron transport layer, the electron injection layer, the first blocking layer, and/or the second blocking layer. Since the layers is substantially the same as those described in the light-emitting element 100 of FIG. 1, a specific description will be omitted. In the case where the light-emitting element 102 includes the first blocking layer, the first blocking layer may include the aforementioned compound according to the present invention.

Meanwhile, the light-emitting element 100 illustrated in FIG. 1 may further include an interlayer (not illustrated). The interlayer may be disposed between the first electrode 20 and the hole transportable layer 30 of FIG. 1, and may be formed of the compound used as the P-type dopant described in FIG. 2.

Referring to FIG. 3, a light-emitting element 104 includes a first electrode 20, a hole transportable layer 34, a light emitting layer 40, and a second electrode 50 formed on a base substrate 10. Since the light-emitting element is substantially the same as that illustrated in FIG. 1 with the exception of the hole transportable layer 34, an overlapping description will be omitted.

The hole transportable layer 34 includes a first layer 33a coming into contact with the first electrode 20, and a second layer 33b disposed between the first layer 33a and the light emitting layer 40. That is, the hole transportable layer 34 may have a two-layered structure. Further, the hole transportable layer 34 may have a multilayered structure of two layers or more including the first and second layers 33a and 33b.

The first and second layers 33a and 33b may include the same kind of hole transportable compound. By having components of the hole transportable compounds included in the first layer 33a and the second layer 33b to be the same as each other, physical and chemical defects that may occur at an interface between heteromaterials may be reduced, and thus holes may be easily injected into the light emitting layer. In another aspect, if the same host material is used in the first layer 33a and the second layer 33b, since the first layer 33a and the second layer 33b may be continuously formed in one chamber, a manufacturing process is simplified and a manufacturing time may be shortened. Moreover, since physical properties such as a glass transition temperature between the adjacent layers become similar to each other, durability of the element may be increased.

The first layer 33a includes the novel compound according to the present invention represented by Chemical Formula 1 as the hole transportable compound, and the P-type dopant. The first layer 33a is substantially the same as the hole transportable layer 32 described in FIG. 2 with the exception of the thickness. Accordingly, an overlapping description will be omitted.

The second layer 33b includes the novel compound according to the present invention represented by Chemical Formula 1 as the hole transportable compound, and the hole transportable compound constituting the second layer 33b may be the same as the hole transportable compound constituting the first layer 33a. Since the second layer 33b is substantially the same as the hole transportable layer 30 described in FIG. 1 with the exception of the thickness, an overlapping detailed description will be omitted.

Unlike this, the first and second layers 33a and 33b may include different kinds of hole transportable compounds. The hole transportable compounds constituting the first and second layers 33a and 33b are the novel compounds according to the present invention represented by Chemical Formula 1, and $R_1$ to $R_4$, La, and $Ar_1$ may be each independently different from each other. In this case, the compound constituting each of the first and second layers 33a and 33b may be selected to have a HOMO value for effectively transferring holes to the light emitting layer 40.

Additionally, the second layer 33b may further include the P-type dopant together with the hole transportable compound. In this case, the kinds of the P-type dopants doped on the first layer 33a and the second layer 33b may be different from each other, and even though the same kind is used, doping amounts may be different from each other. For example, the content P1 of the P-type dopant doped on the first layer 33a and the content P2 of the P-type dopant doped on the second layer 33b may satisfy a relationship of the following Equation 1.

$$P1/P2 \geq 1 \quad \text{[Equation 1]}$$

In Equation 1,

"P1" is the content of the doped P-type dopant based on 100 parts by weight of the hole transportable compound in the first layer 33a, and "P2" is the content of the doped P-type dopant based on 100 parts by weight of the hole transportable compound in the second layer 33b.

For example, the content of the P-type dopant doped on the first layer 33a may be in the range of 0.3 to 20 parts by weight, 1 to 15 parts by weight, 2 to 10 parts by weight, or 4 to 6 parts by weight based on 100 parts by weight of the hole transportable compound. Further, the content of the P-type dopant doped on the second layer 33b may be in the range of 0.3 to 20 parts by weight, 0.5 to 10 parts by weight, 1 to 8 parts by weight, or 2 to 4 parts by weight based on 100 parts by weight of the hole transportable compound.

Further, although not illustrated in the drawings, the light-emitting element 104 may further include the electron transport layer, the electron injection layer, the first blocking layer, and/or the second blocking layer. Since the layers is substantially the same as those described in the light-emitting element 100 of FIG. 1, a specific description will be omitted.

Each of the aforementioned light-emitting elements 100, 102, and 104 may include the novel compound according to the present invention represented by Chemical Formula 1, and thus the light-emitting elements 100, 102, and 104 may have excellent thermal stability, and simultaneously light emitting efficiency may be improved and a life-span may be lengthened.

FIGS. 1 to 3 illustrate that the light-emitting elements 100, 102, and 104 are directly formed on the base substrate 10, but a thin film transistor as a switching element driving a pixel may be disposed between the first electrode 20 and the base substrate 10 of each of the light-emitting elements 100, 102, and 104. In this case, the first electrode 20 may become a pixel electrode connected to the thin film transistor. In the case where the first electrode 20 is the pixel electrode, the first electrodes 20 may be disposed to be separated from each other in a plurality of pixels and a partition wall pattern formed along an edge of the first electrode 20 may be formed on the base substrate 10 to isolate layers laminated on the first electrodes 20 disposed in the pixels that are adjacent to each other from each other. That is, although not illustrated in the drawings, the light-emitting elements 100, 102, and 104 may be used in a display device displaying an image without a backlight.

Further, the light-emitting elements 100, 102, and 104 may be used as a lighting device.

As described above, the light-emitting elements 100, 102, and 104 exemplified in the present invention may be used in various electronic devices such as the display device or the lighting device.

EXAMPLES

Hereinafter, the novel compounds according to the present invention will be described in more detail through specific Examples according to the present invention. The Examples exemplified below are set forth only for the detailed description of the invention, but are not to be construed to limit the scope of the right.

Example 1

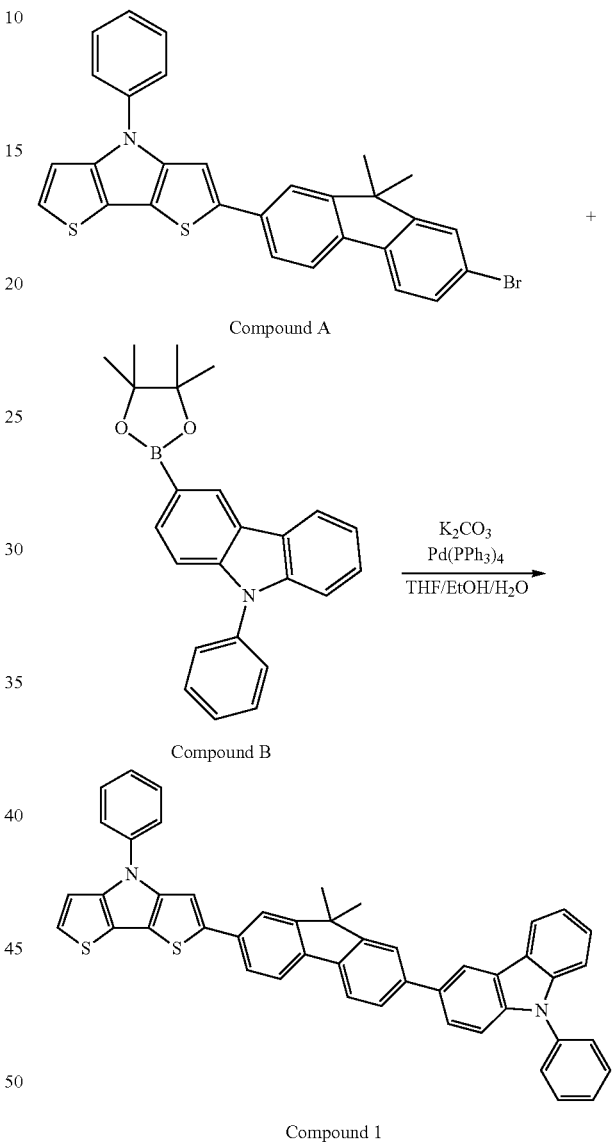

After nitrogen was charged in the 1 L three-neck round bottom flask, compound A (37.9 mmol, 20 g), compound B (41.7 mmol, 15.4 g), 200 mL of tetrahydrofuran (THF), and 100 mL of ethanol (EtOH) were added and agitated for 30 minutes. Further, potassium carbonate ($K_2CO_3$) (151.9 mmol, 21.0 g) was dissolved in 100 mL of water ($H_2O$), and then the solution is added to the 1 L three-neck round bottom flask. Subsequently, after tetrakis(triphenylphosphine)palladium ($Pd(PPh_3)_4$, 1.5 mmol, 1.76 g) was added to the 1 L three-neck round bottom flask, light was blocked and reflux was performed for 6 hours.

The reaction mixture was cooled, extracted and concentrated by using ethyl acetate (EA) and distilled water, dissolved in 100 mL of tetrahydrofuran (THF), and added to 1 L of methanol, followed by agitation for 20 minutes and filtration to obtain 21.1 g of compound 1 that was the light grey solid (yield 80%).

MALDI-TOF: m/z=688.1923 ($C_{47}H_{32}N_2S_2$=688.2)

Example 2

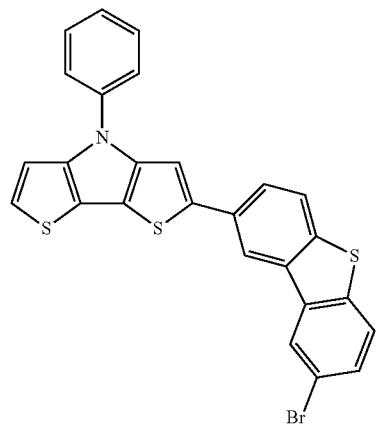

Compound C

+

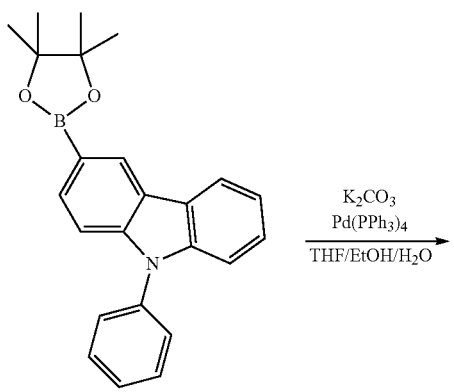

Compound B $\xrightarrow{\begin{array}{c}K_2CO_3\\Pd(PPh_3)_4\\\hline THF/EtOH/H_2O\end{array}}$ -continued

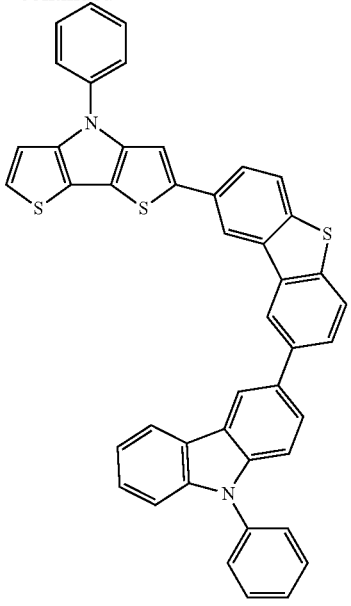

Compound 2

After nitrogen was charged in the 1 L three-neck round bottom flask, compound C (38.7 mmol, 20 g), compound B (42.5 mmol, 15.7 g), 200 mL of tetrahydrofuran (THF), and 100 mL of ethanol (EtOH) were added and agitated for 30 minutes. Further, potassium carbonate ($K_2CO_3$) (154.8 mmol, 21.4 g) was dissolved in 100 mL of water ($H_2O$), and then the solution is added to the 1 L three-neck round bottom flask. Subsequently, after tetrakis(triphenylphosphine)palladium (Pd(PPh$_3$)$_4$, 1.5 mmol, 1.79 g) was added to the 1 L three-neck round bottom flask, light was blocked and reflux was performed for 5 hours.

The reaction mixture was cooled, extracted and concentrated by using ethyl acetate (EA) and distilled water, dissolved in 100 mL of tetrahydrofuran (THF), and added to 1 L of methanol, followed by agitation for 20 minutes and filtration to obtain 23.5 g of compound 2 that was the light grey solid (yield 90%).

MALDI-TOF: m/z=678.2320 ($C_{44}H_{36}N_2S_3$=678.1)

Example 3

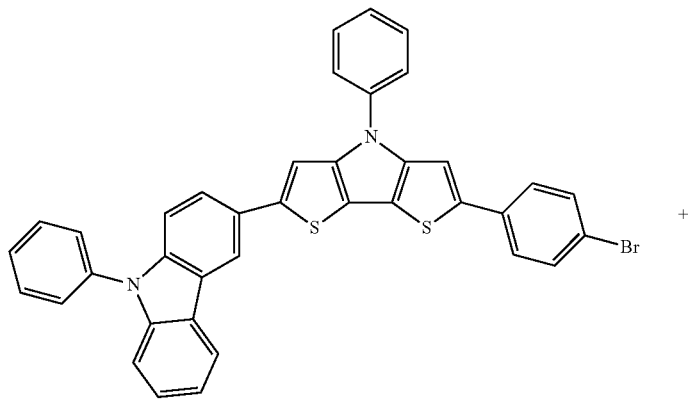

Compound D

-continued

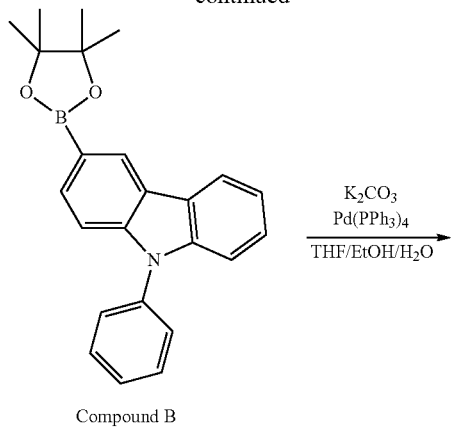

Compound B

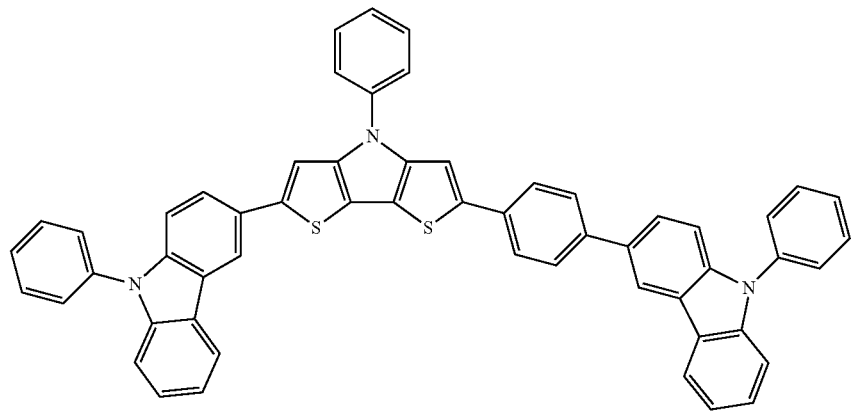

Compound 3

After nitrogen was charged in the 1 L three-neck round bottom flask, compound D (30.6 mmol, 20 g), compound B (33.7 mmol, 12.4 g), 200 mL of tetrahydrofuran (THF), and 100 mL of ethanol (EtOH) were added and agitated for 30 minutes. Further, potassium carbonate (K₂CO₃) (122.7 mmol, 16.9 g) was dissolved in 100 mL of water (H₂O), and then the solution is added to the 1 L three-neck round bottom flask. Subsequently, after tetrakis(triphenylphosphine)palladium (Pd(PPh₃)₄, 1.2 mmol, 1.42 g) was added to the 1 L three-neck round bottom flask, light was blocked and reflux was performed for 6 hours.

The reaction mixture was cooled, extracted and concentrated by using ethyl acetate (EA) and distilled water, dissolved in 100 mL of tetrahydrofuran (THF), and added to 1 L of methanol, followed by agitation for 20 minutes and filtration to obtain 19.8 g of compound 3 that was the light grey solid (yield 80%).

MALDI-TOF: m/z=813.1983 ($C_{56}H_{35}N_3S_2$=813.2)

Example 4

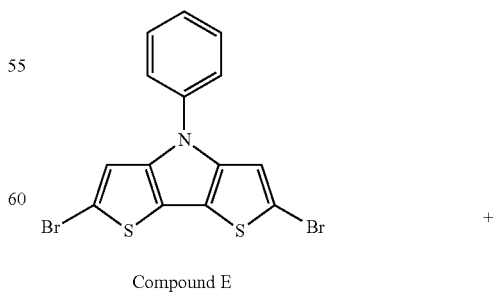

Compound E

+

-continued

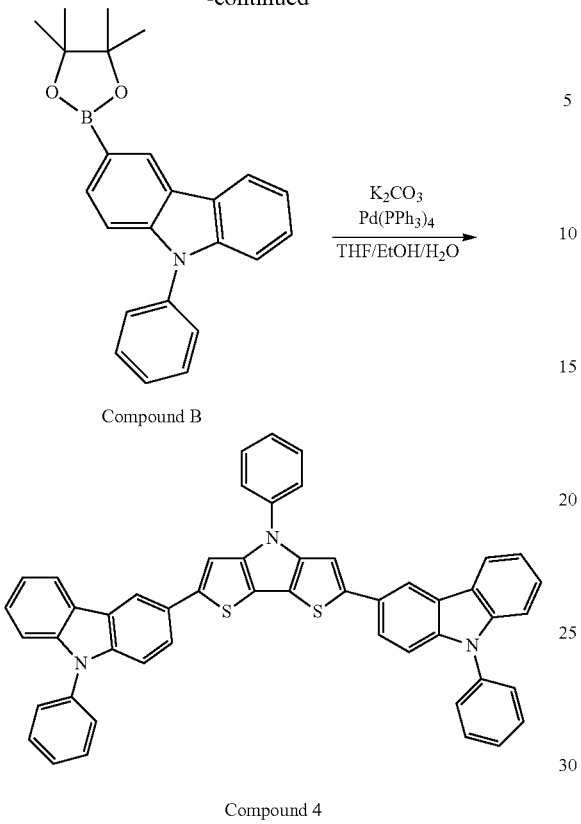

Compound B

Compound 4

After nitrogen was charged in the 1 L three-neck round bottom flask, compound E (48.4 mmol, 20 g), compound B (106.4 mmol, 39.3 g), 200 mL of tetrahydrofuran (THF), and 100 mL of ethanol (EtOH) were added and agitated for 30 minutes. Further, potassium carbonate ($K_2CO_3$) (387.2 mmol, 53.52 g) was dissolved in 150 mL of water ($H_2O$), and then the solution is added to the 1 L three-neck round bottom flask. Subsequently, after tetrakis(triphenylphosphine)palladium (Pd(PPh$_3$)$_4$, 3.87 mmol, 4.47 g) was added to the 1 L three-neck round bottom flask, light was blocked and reflux was performed for 12 hours.

The reaction mixture was cooled, extracted and concentrated by using ethyl acetate (EA) and distilled water, dissolved in 100 mL of tetrahydrofuran (THF), and added to 1 L of methanol, followed by agitation for 20 minutes and filtration to obtain 25.1 g of compound 4 that was the light grey solid (yield 71%).

MALDI-TOF: m/z=737.2032 ($C_{50}H_{31}N_3S_2$=737.2)

Example 5

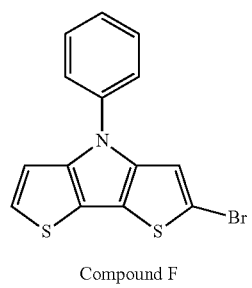

Compound F

+

-continued

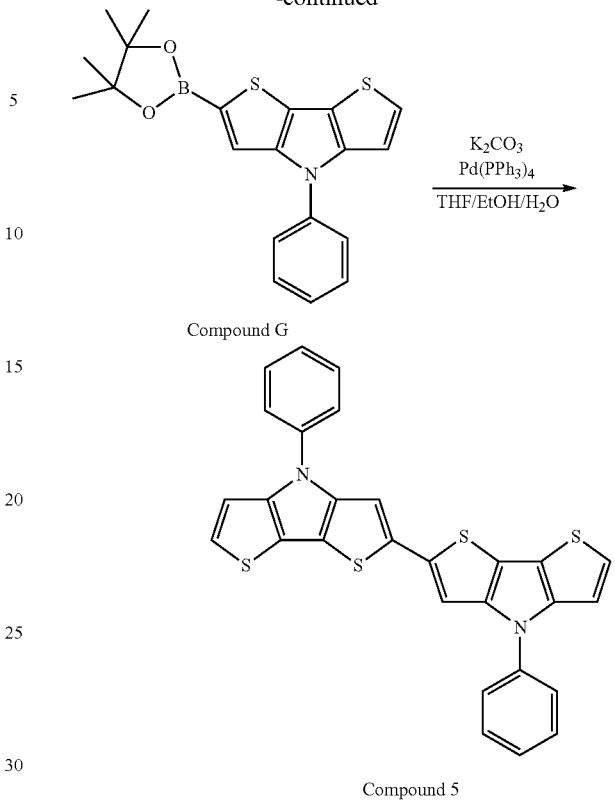

Compound G

Compound 5

After nitrogen was charged in the 1 L three-neck round bottom flask, compound F (59.8 mmol, 20 g), compound G (65.8 mmol, 25.0 g), 200 mL of tetrahydrofuran (THF), and 100 mL of ethanol (EtOH) were added and agitated for 30 minutes. Further, potassium carbonate ($K_2CO_3$) (239.3 mmol, 33.07 g) was dissolved in 100 mL of water ($H_2O$), and then the solution is added to the 1 L three-neck round bottom flask. Subsequently, after tetrakis(triphenylphosphine)palladium (Pd(PPh$_3$)$_4$, 2.3 mmol, 2.77 g) was added to the 1 L three-neck round bottom flask, light was blocked and reflux was performed for 12 hours.

The reaction mixture was cooled, extracted and concentrated by using ethyl acetate (EA) and distilled water, dissolved in 100 mL of tetrahydrofuran (THF), and added to 1 L of methanol, followed by agitation for 20 minutes and filtration to obtain 26.5 g of compound 5 that was the light grey solid (yield 87%).

MALDI-TOF: m/z=508.1235 ($C_{28}H_{16}N_2S_4$=508.0)

Example 6

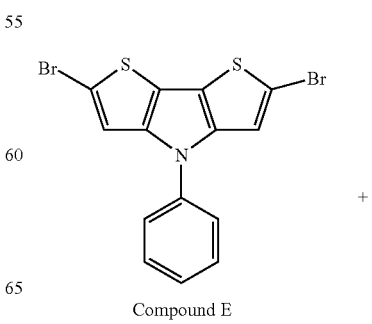

Compound E

+

77
-continued

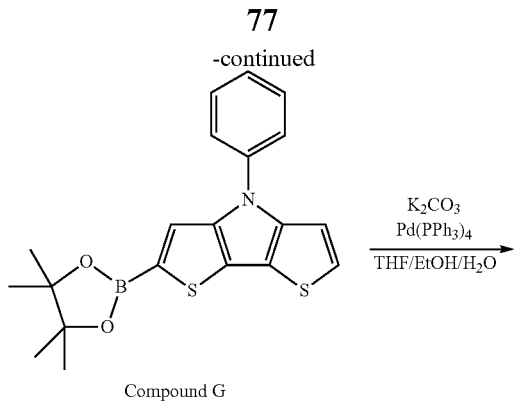

Compound G

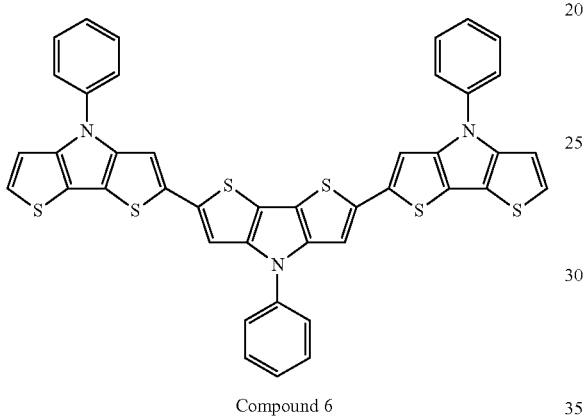

Compound 6

After nitrogen was charged in the 1 L three-neck round bottom flask, compound E (48.4 mmol, 20 g), compound G (106.4 mmol, 40.6 g), 200 mL of tetrahydrofuran (THF), and 100 mL of ethanol (EtOH) were added and agitated for 30 minutes. Further, potassium carbonate ($K_2CO_3$) (387.2 mmol, 53.52 g) was dissolved in 150 mL of water ($H_2O$), and then the solution is added to the 1 L three-neck round bottom flask. Subsequently, after tetrakis(triphenylphosphine)palladium ($Pd(PPh_3)_4$, 3.87 mmol, 4.47 g) was added to the 1 L three-neck round bottom flask, light was blocked and reflux was performed for 12 hours.

The reaction mixture was cooled, extracted and concentrated by using ethyl acetate (EA) and distilled water, dissolved in 100 mL of tetrahydrofuran (THF), and added to 1 L of methanol, followed by agitation for 20 minutes and filtration to obtain 20.5 g of compound 6 that was the light grey solid (yield 55%).

MALDI-TOF: m/z=760.9824 ($C_{42}H_{23}N_3S_6$=761.0)

78
Example 7

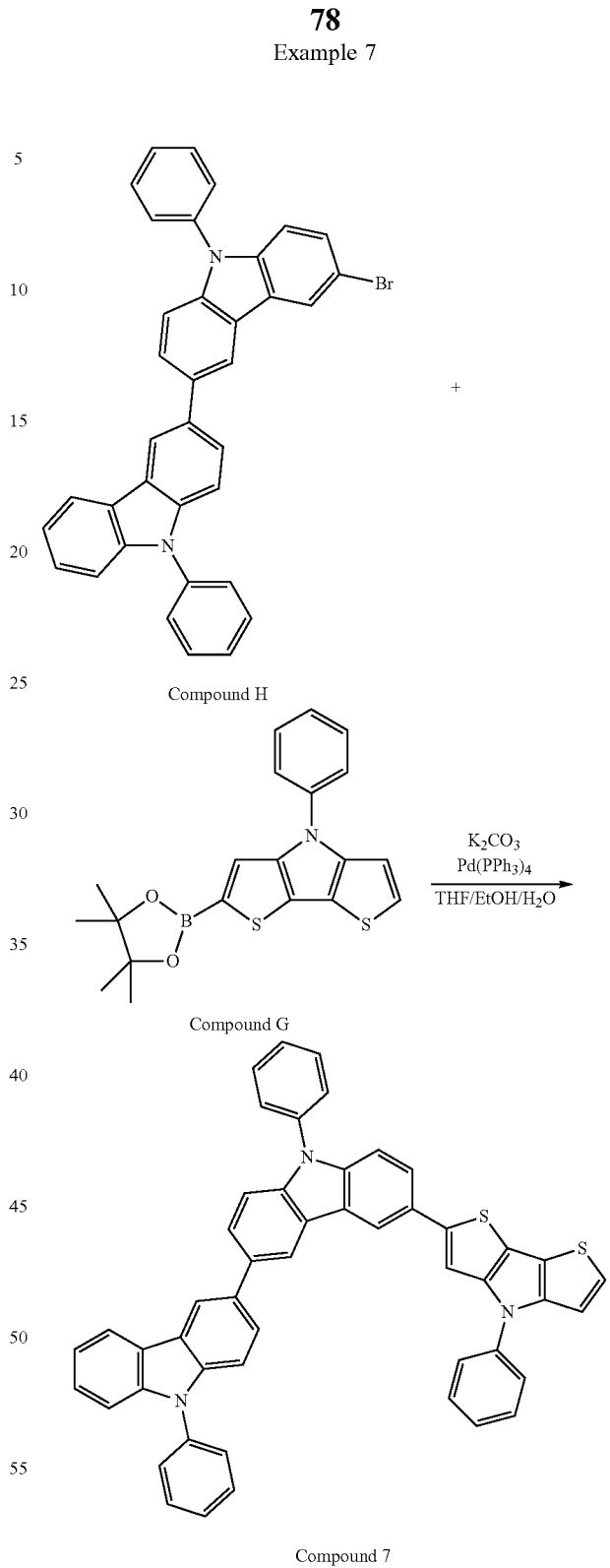

After nitrogen was charged in the 1 L three-neck round bottom flask, compound H (35.4 mmol, 20 g), compound G (39.04 mmol, 14.89 g), 200 mL of tetrahydrofuran (THF), and 100 mL of ethanol (EtOH) were added and agitated for 30 minutes. Further, potassium carbonate ($K_2CO_3$) (141.9 mmol, 19.62 g) was dissolved in 100 mL of water ($H_2O$), and then the solution is added to the 1 L three-neck round bottom flask. Subsequently, after tetrakis(triphenylphosphine)palladium (Pd(PPh$_3$)$_4$, 1.42 mmol, 1.64 g) was added to the 1 L three-neck round bottom flask, light was blocked and reflux was performed for 12 hours.

The reaction mixture was cooled, extracted and concentrated by using ethyl acetate (EA) and distilled water, dissolved in 100 mL of tetrahydrofuran (THF), and added to 1 L of methanol, followed by agitation for 20 minutes and filtration to obtain 18.3 g of compound 7 that was the light grey solid (yield 70%).

MALDI-TOF: m/z=737.2100 (C$_{50}$H$_{31}$N$_3$S$_2$=737.2)

Example 8

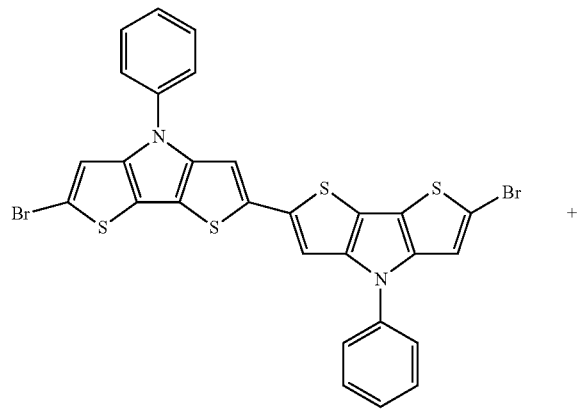

Compound I

Example 9

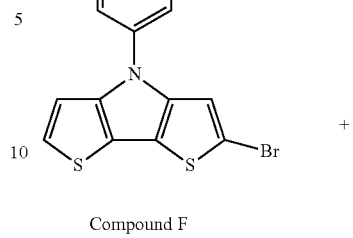

Compound F

+

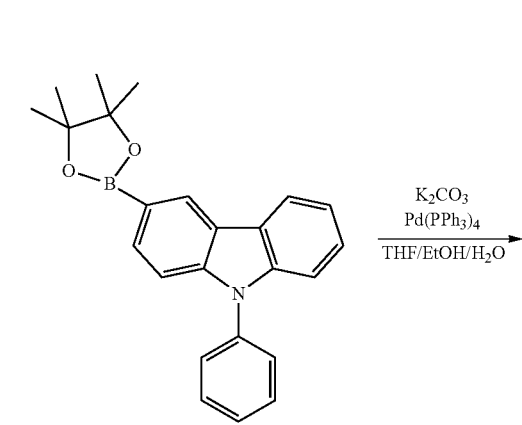

Compound B $\xrightarrow[\text{THF/EtOH/H}_2\text{O}]{\text{K}_2\text{CO}_3 \quad \text{Pd(PPh}_3)_4}$

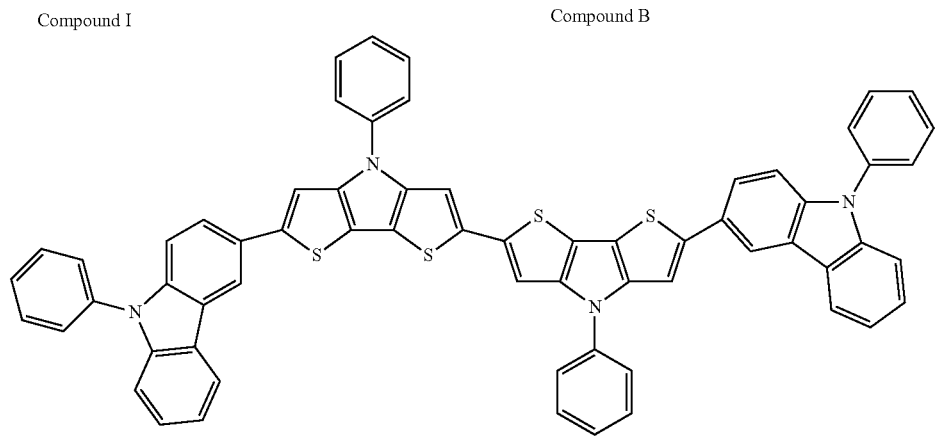

Compound 8

After nitrogen was charged in the 1 L three-neck round bottom flask, compound I (30.0 mmol, 20 g), compound B (66.0 mmol, 24.38 g), 200 mL of tetrahydrofuran (THF), and 100 mL of ethanol (EtOH) were added and agitated for 30 minutes. Further, potassium carbonate (K$_2$CO$_3$) (240.0 mmol, 33.18 g) was dissolved in 150 mL of water (H$_2$O), and then the solution is added to the 1 L three-neck round bottom flask. Subsequently, after tetrakis(triphenylphosphine)palladium (Pd(PPh$_3$)$_4$, 2.4 mmol, 2.77 g) was added to the 1 L three-neck round bottom flask, light was blocked and reflux was performed for 12 hours.

The reaction mixture was cooled, extracted and concentrated by using ethyl acetate (EA) and distilled water, dissolved in 100 mL of tetrahydrofuran (THF), and added to 1 L of methanol, followed by agitation for 20 minutes and filtration to obtain 23.6 g of compound 8 that was the light grey solid (yield 79%).

MALDI-TOF: m/z=990.2561 (C$_{64}$H$_{38}$N$_4$S$_4$=990.2)

-continued

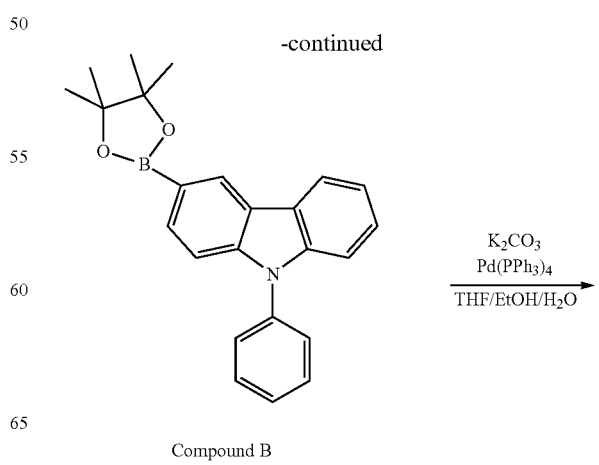

Compound B $\xrightarrow[\text{THF/EtOH/H}_2\text{O}]{\text{K}_2\text{CO}_3 \quad \text{Pd(PPh}_3)_4}$ -continued

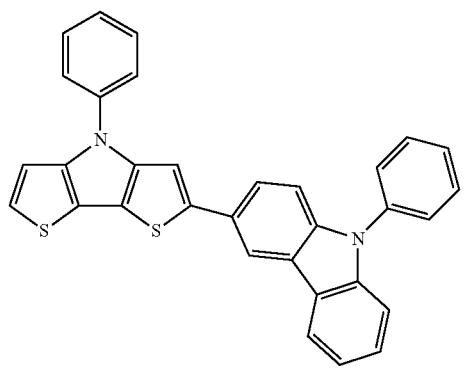

Compound 9

-continued

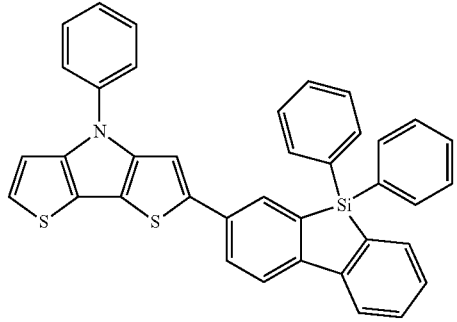

Compound 10

After nitrogen was charged in the 1 L three-neck round bottom flask, compound F (59.8 mmol, 20 g), compound B (65.8 mmol, 24.3 g), 200 mL of tetrahydrofuran (THF), and 100 mL of ethanol (EtOH) were added and agitated for 30 minutes. Further, potassium carbonate (K$_2$CO$_3$) (239.3 mmol, 33.07 g) was dissolved in 100 mL of water (H$_2$O), and then the solution is added to the 1 L three-neck round bottom flask. Subsequently, after tetrakis(triphenylphosphine)palladium (Pd(PPh$_3$)$_4$, 2.3 mmol, 2.77 g) was added to the 1 L three-neck round bottom flask, light was blocked and reflux was performed for 12 hours.

The reaction mixture was cooled, extracted and concentrated by using ethyl acetate (EA) and distilled water, dissolved in 100 mL of tetrahydrofuran (THF), and added to 1 L of methanol, followed by agitation for 20 minutes and filtration to obtain 23.5 g of compound 9 that was the light grey solid (yield 79%).

MALDI-TOF: m/z=496.9564 (C$_{32}$H$_{20}$N$_2$S$_2$=496.1)

After nitrogen was charged in the 1 L three-neck round bottom flask, compound F (59.8 mmol, 20 g), compound J (65.8 mmol, 30.3 g), 200 mL of tetrahydrofuran (THF), and 100 mL of ethanol (EtOH) were added and agitated for 30 minutes. Further, potassium carbonate (K$_2$CO$_3$) (239.3 mmol, 33.07 g) was dissolved in 100 mL of water (H$_2$O), and then the solution is added to the 1 L three-neck round bottom flask. Subsequently, after tetrakis(triphenylphosphine)palladium (Pd(PPh$_3$)$_4$, 2.3 mmol, 2.77 g) was added to the 1 L three-neck round bottom flask, light was blocked and reflux was performed for 12 hours.

The reaction mixture was cooled, extracted and concentrated by using ethyl acetate (EA) and distilled water, dissolved in 100 mL of tetrahydrofuran (THF), and added to 1 L of methanol, followed by agitation for 20 minutes and filtration to obtain 29.8 g of compound 10 that was the light grey solid (yield 85%).

MALDI-TOF: m/z=587.1147 (C$_{38}$H$_{25}$NS$_2$Si=587.1)

Example 10

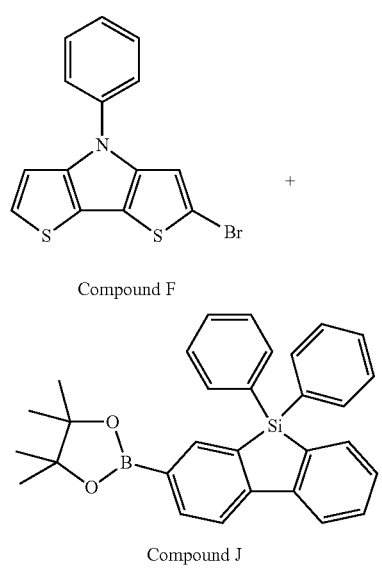

Example 11

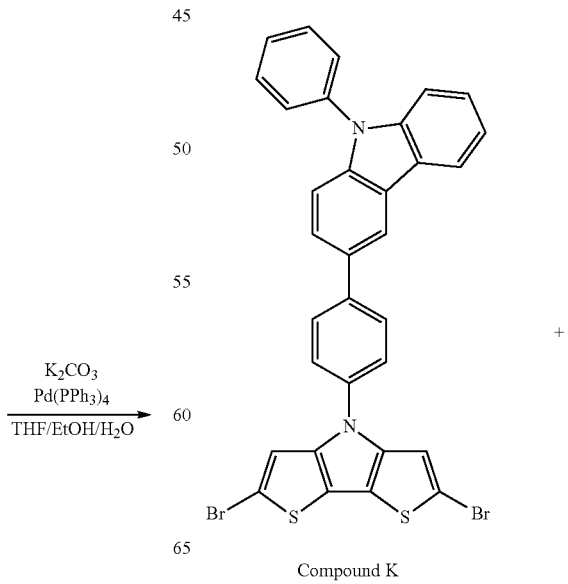

-continued

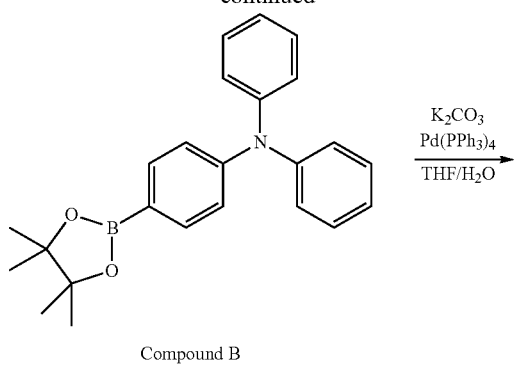

Compound B

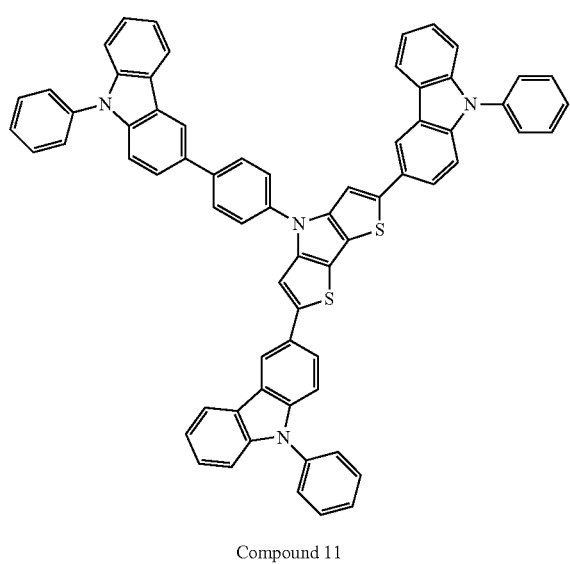

Compound 11

Example 12

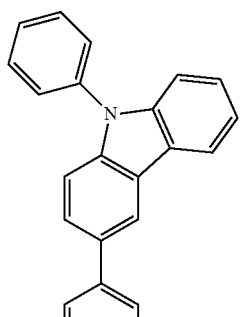

Compound K

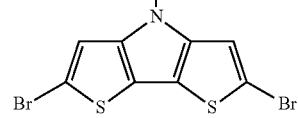

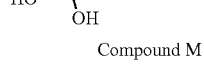

Compound M

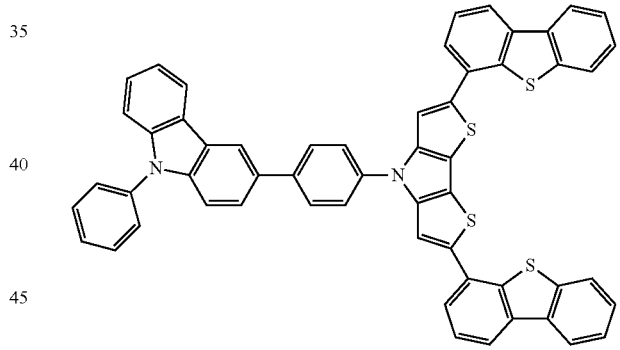

Compound 12

After nitrogen was charged in the 1 L three-neck round bottom flask, compound K (33.7 mmol, 20 g), compound B (67.4 mmol, 24.9 g), 200 mL of tetrahydrofuran (THF), and 100 mL of ethanol (EtOH) were added and agitated for 30 minutes. Further, potassium carbonate ($K_2CO_3$) (74.1 mmol, 10.25 g) was dissolved in 100 mL of water ($H_2O$), and then added to the 1 L three-neck round bottom flask. Subsequently, after tetrakis(triphenylphosphine)palladium (Pd($PPh_3)_4$, 2.1 mmol, 2.53 g) was added to the 1 L three-neck round bottom flask, reflux was performed for 12 hours.

The reaction mixture was cooled, extracted and concentrated by using ethyl acetate (EA) and distilled water, and added to 1 L of methanol, followed by agitation for 20 minutes and filtration to obtain 30.5 g of compound 11 that was the light grey solid (yield 91%).

MALDI-TOF: m/z=978.2851 ($C_{68}H_{42}N_4S_2$=978.3)

After nitrogen was charged in the 1 L three-neck round bottom flask, compound K (56.8 mmol, 37 g), compound M (113.5 mmol, 25.9 g), 200 mL of tetrahydrofuran (THF), and 100 mL of ethanol (EtOH) were added and agitated for 30 minutes. Further, potassium carbonate ($K_2CO_3$) (112.5 mmol, 17.27 g) was dissolved in 100 mL of water ($H_2O$), and then the solution is added to the 1 L three-neck round bottom flask. Subsequently, after tetrakis(triphenylphosphine)palladium (Pd($PPh_3)_4$, 2.3 mmol, 2.54 g) was added to the 1 L three-neck round bottom flask, reflux was performed for 12 hours.

The reaction mixture was cooled, extracted and concentrated by using ethyl acetate (EA) and distilled water, and added to 2 L of methanol, followed by agitation for 20 minutes and filtration to obtain 41.2 g of compound 12 that was the light grey solid (yield 84%).

MALDI-TOF: m/z=860.1448 ($C_{56}H_{32}N_2S_4$=860.1)

Comparative Examples 1 to 4

The compounds having the structures of the following Chemical Formulas a, b, c, and d were commercially obtained or manufactured to be used as Comparative Examples 1 to 4.

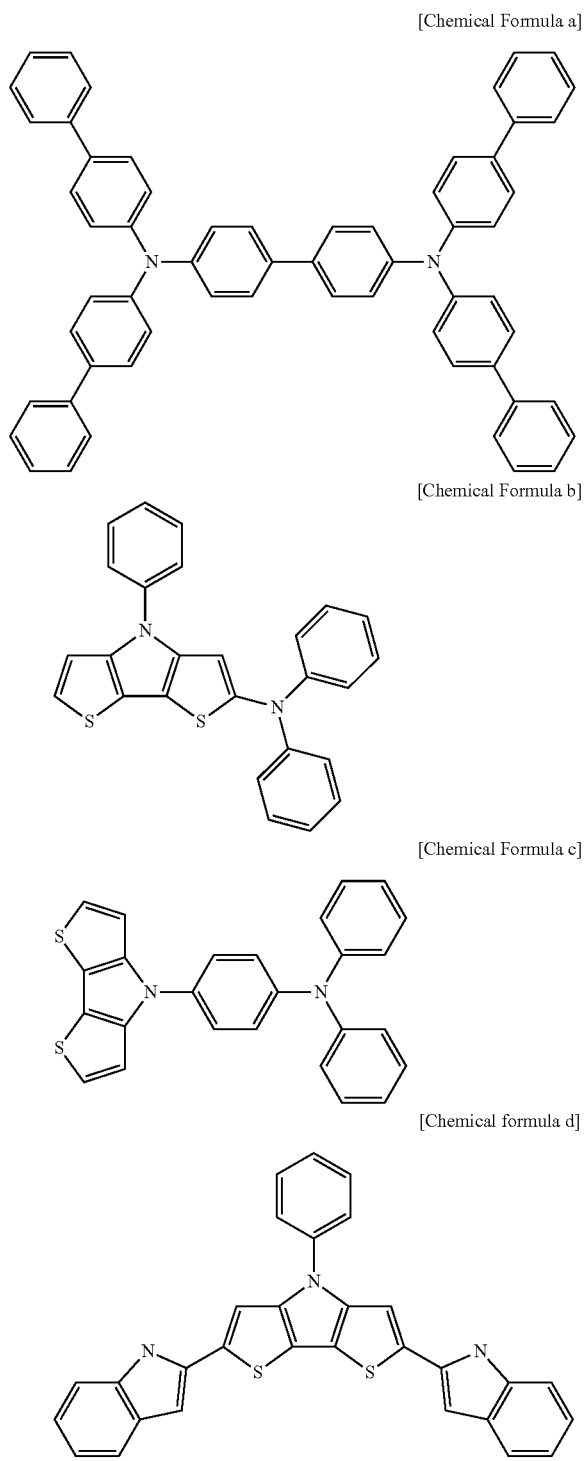

[Chemical Formula a]

[Chemical Formula b]

[Chemical Formula c]

[Chemical formula d]

Manufacturing of Light-Emitting Elements A-1 to A-10

On the first electrode formed of indium-tin oxide (ITO), the compound according to Example 1 as the host material was evaporated at the rate of 1 Å/sec, and simultaneously, the P-type dopant (HAT-CN) represented by the following Chemical Formula 12 was co-evaporated at the ratio of about 5 parts by weight based on 100 parts by weight of the host material to form the first layer having the thickness of 100 Å. On the first layer, the compound according to Example 1 was evaporated in the thickness of 300 Å to form the second layer.

On the second layer, mCBP represented by the following Chemical Formula 13 and Ir(ppy)$_3$ represented by Chemical Formula 14 were co-evaporated at the weight ratio of 100:9 to form the light emitting layer having the thickness of about 300 Å, and on the light emitting layer, mCBP was evaporated again in the thickness of about 50 Å to form the blocking layer.

On the blocking layer, BPhen represented by the following Chemical Formula 15 and Alga represented by the following Chemical Formula 16 were co-evaporated at the weight ratio of 50:50 to form the electron transport layer having the thickness of about 400 Å. Subsequently, on the electron transport layer, the electron injection layer having the thickness of about 10 Å was formed by using Liq represented by the following Chemical Formula 17.

On the electron injection layer, the second electrode using the aluminum thin film having the thickness of 1,000 Å was formed.

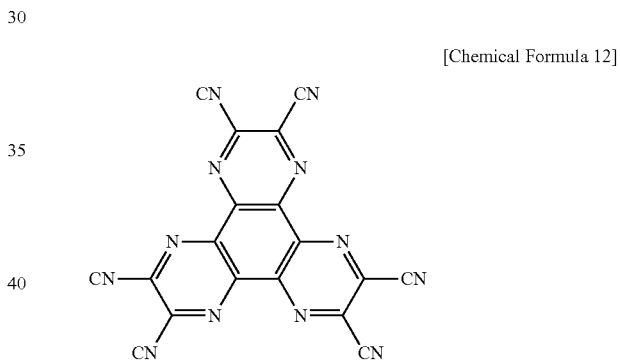

[Chemical Formula 12]

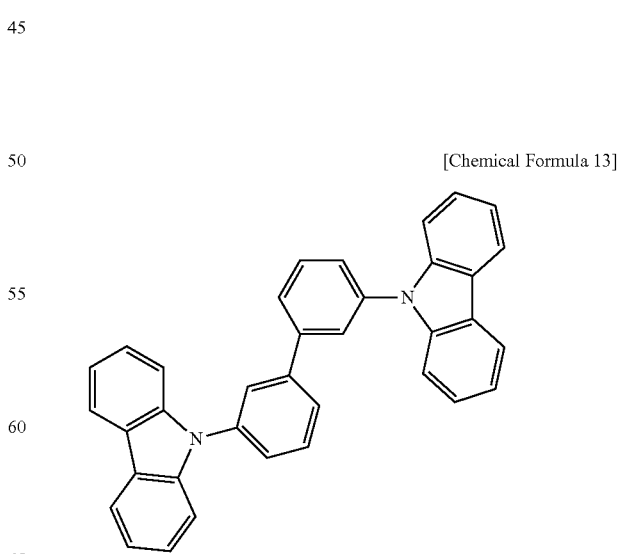

[Chemical Formula 13]

[Chemical Formula 14]

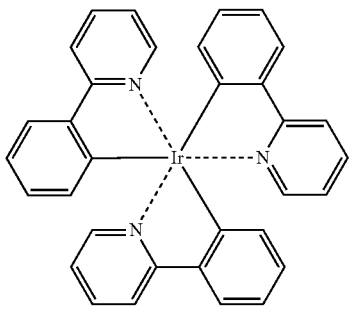

[Chemical Formula 15]

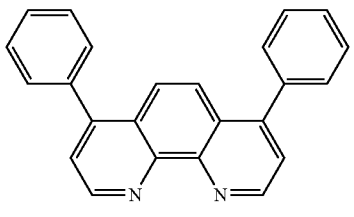

[Chemical Formula 16]

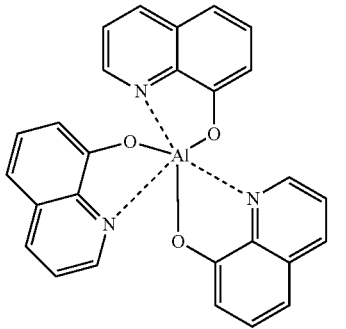

[Chemical Formula 17]

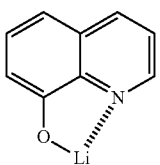

Light-emitting element A-1 including the compound according to Example 1 of the present invention was manufactured by the aforementioned method.

Further, light-emitting elements A-2 to A-10 were manufactured through the process that was substantially the same as the process of manufacturing the light-emitting element A-1, except that the hole transportable layer was formed by using each of the compounds according to Examples 2 to 10 as the host material.

Manufacturing of Comparative Elements 1 to 4

Comparative elements 1 to 4 were manufactured through the process that was substantially the same as the process of manufacturing the light-emitting element A-1, except that the first layer and the second layer were formed by using the compounds according to Comparative Examples 1 to 4 as the host material.

Evaluation of Power Efficiency and Life-Span of Light-Emitting Element-1

With respect to each of the light-emitting elements A-1 to A-10 and the comparative elements 1 to 4, after the silant for UV curing was dispensed at the edge of the cover glass to which the getter was attached in the globe box under the nitrogen atmosphere, each of the light-emitting elements and the comparative elements was adhered to the cover glass, and UV light was radiated to perform curing. With respect to each of light-emitting elements A-1 to A-10 and comparative elements 1 to 4 as prepared in the above, power efficiency was measured based on the value when luminance was 500 cd/m$^2$. The result is described in Table 5.

Further, the life-span of each of light-emitting elements A-1 to A-10 and comparative elements 1 to 4 was measured by using the life-span measurement apparatus installed in the oven for measurement constantly maintaining the temperature of about 85° C. The result is described in Table 5.

In Table 5, a unit of the measurement result of power efficiency is lm/W. Further, in Table 5, in the case where initial luminance of the light-emitting element is 1,000 cd/m$^2$, $T_{75}$ means a time required until luminance of the light-emitting element becomes 75% of the initial luminance.

TABLE 5

| Element No. | Power efficiency [lm/W] | Life-span ($T_{75}$@85° C. [hr]) |
| --- | --- | --- |
| Light-emitting element A-1 | 29.0 | 673 |
| Light-emitting element A-2 | 20.5 | 479 |
| Light-emitting element A-3 | 28.0 | 647 |
| Light-emitting element A-4 | 26.2 | 606 |
| Light-emitting element A-5 | 20.4 | 467 |
| Light-emitting element A-6 | 16.3 | 379 |
| Light-emitting element A-7 | 22.8 | 533 |
| Light-emitting element A-8 | 24.2 | 558 |
| Light-emitting element A-9 | 20.8 | 476 |
| Light-emitting element A-10 | 18.6 | 424 |
| Comparative element 1 | 9.2 | 227 |
| Comparative element 2 | 10.5 | 268 |
| Comparative element 3 | 11.0 | 279 |
| Comparative element 4 | 10.3 | 235 |

Referring to Table 5, it can be seen that power efficiency of each of the light-emitting elements manufactured by using the compounds according to Examples 1 to 10 of the present invention is at least 16.3 lm/W and is better than power efficiency of comparative elements 1 to 4 which is 9.2 lm/W to 11.0 lm/W.

Further, it can be seen that the life-spans of the light-emitting elements manufactured by using the compounds according to Examples 1 to 10 of the present invention are at least about 379 hours and mostly about 300 hours or more. On the other hand, it can be seen that as compared to the life-span of comparative elements 1 to 4 of about 279 hours or less, the life-spans of the light-emitting elements including the compounds according to Examples 1 to 10 of the present invention are better than those of comparative elements 1 to 4.

Further, in consideration of evaluation of the life-span property of the light-emitting element performed under the acceleration condition (severe condition) of 85° C., from the fact that that the life-span property of the light-emitting elements including the compounds according to Examples 1 to 10 of the present invention is better than that of comparative elements 1 to 4, it can be seen that heat resistance of the light-emitting elements manufactured by using the compound according to the present invention is better than that of comparative elements 1 to 4.

Manufacturing of Light-Emitting Elements B-1 to B-4

On the first electrode formed of indium-tin oxide (ITO), HAT-CN represented by Chemical Formula 12 was evaporated in the thickness of about 100 Å to form the first layer, and on the first layer, NPB (N,N'-diphenyl-N,N'-bis(1-naphthyl)-1,1'-biphenyl-4,4'-diamine) was evaporated in the thickness of about 300 Å to form the second layer.

On the second layer, the first blocking layer having the thickness of about 100 Å was formed of the compound according to Example 1, on the first blocking layer, mCBP represented by Chemical Formula 13 and Ir(ppy)$_3$ represented by Chemical Formula 14 were co-evaporated at the weight ratio of 100:9 to form the light emitting layer having the thickness of about 300 Å, and on the light emitting layer, mCBP was evaporated again in the thickness of about 50 Å to form the second blocking layer.

Then, on the second blocking layer, BPhen represented by Chemical Formula 15 and Alga represented by Chemical Formula 16 were co-evaporated at the weight ratio of 50:50 to form the electron transport layer having the thickness of about 400 Å. Subsequently, on the electron transport layer, the electron injection layer having the thickness of about 10 Å was formed by using Liq represented by Chemical Formula 17.

On the electron injection layer, the second electrode using the aluminum thin film having the thickness of 1,000 Å was formed to manufacture light-emitting element B-1 including the compound according to Example 1 of the present invention.

Light-emitting elements B-2, B-3, and B-4 were manufactured through the process that was substantially the same as the process of manufacturing the light-emitting element B-1, except that the first blocking layer was manufactured by using each of the compounds according to Examples 3, 5, and 8 of the present invention.

Manufacturing of Comparative Elements 5 and 6

Comparative element 5 was manufactured through the process that was substantially the same as the process of manufacturing the light-emitting element B-1, except that the first blocking layer was manufactured by using the compound according to Comparative Example 1 represented by Chemical Formula a.

Further, comparative element 6 was manufactured through the process that was substantially the same as the process of manufacturing the light-emitting element B-1, except that the first blocking layer was manufactured by using the compound according to Comparative Example 4 represented by Chemical Formula d.

Evaluation of Power Efficiency and Life-Span of Light-Emitting Element-2

With respect to each of light-emitting elements B-1 to B-4 and comparative elements 5 and 6 as prepared in the above, power efficiency was measured based on the value when luminance was 500 cd/m$^2$ by the method that was substantially the same as the power efficiency measurement experiment of the light-emitting elements A-1 to A-10.

Further, the life-span of each of light-emitting elements B-1 to B-4 and comparative elements 5 and 6 was measured by the method that was substantially the same as in the aforementioned life-span evaluation experiment of light-emitting elements A-1 to A-10.

The results of power efficiency and the life-span of each of the light-emitting elements B-1 to B-4 and comparative elements 5 and 6 are described in Table 6. In Table 6, a unit of the measurement result of power efficiency is lm/W. Further, in Table 6, in the case where initial luminance of the light-emitting element is 1,000 cd/m$^2$, $T_{75}$ means a time required until luminance of the light-emitting element becomes 75% of the initial luminance.

TABLE 6

| Element No. | Power efficiency [lm/W] | Life-span ($T_{75}$@85° C. [hr]) |
|---|---|---|
| Light-emitting element B-1 | 23.8 | 554 |
| Light-emitting element B-2 | 22.9 | 537 |
| Light-emitting element B-3 | 16.8 | 387 |
| Light-emitting element B-4 | 19.9 | 459 |
| Comparative element 5 | 7.9 | 185 |
| Comparative element 6 | 8.4 | 196 |

Referring to Table 6, it can be seen that power efficiency of each of light-emitting elements B-1 to B-4 manufactured by using the compounds according to the present invention is at least 16.8 lm/W but power efficiency of comparative element 5 is just about 7.9 lm/W and power efficiency of comparative element 6 is just about 8.4 lm/W.

Further, it can be seen that the life-span of each of light-emitting elements B-1 to B-4 is at least about 387 hours, and as compared to the life-spans of comparative elements 5 and 6 which are about 185 hours and about 196 hours, respectively, the life-spans of light-emitting elements B-1 to B-4 are relatively longer than that of comparative elements 5 and 6.

Further, in consideration of evaluation of the life-span property of the light-emitting element performed under the acceleration condition (severe condition) of 85° C., from the fact that that the life-span property of the light-emitting element including the compound according to the present invention is better than that of comparative elements 5 and 6, it can be seen that heat resistance of the light-emitting element manufactured by using the compound according to the present invention is good.

Manufacturing of Light-Emitting Elements C-1 to C-4

On the first electrode formed of indium-tin oxide (ITO), NPB as the host material was evaporated at the rate of 1 Å/sec, and simultaneously, the P-type dopant (HAT-CN) represented by the following Chemical Formula 12 was co-evaporated at the ratio of about 5 parts by weight based on 100 parts by weight of the host material to form the first layer having the thickness of 100 Å. On the first layer, NPB was evaporated in the thickness of 300 Å to form the second layer. On the second layer, the first blocking layer having the thickness of about 100 Å was formed of the compound according to Example 3, on the first blocking layer, mCBP represented by Chemical Formula 13 and Ir(ppy)$_3$ represented by Chemical Formula 14 were co-evaporated at the weight ratio of 100:9 to form the light emitting layer having the thickness of about 300 Å, and on the light emitting layer, mCBP was evaporated again in the thickness of about 50 Å to form the second blocking layer.

Then, on the second blocking layer, BPhen represented by Chemical Formula 15 and Alga represented by Chemical Formula 16 were co-evaporated at the weight ratio of 50:50 to form the electron transport layer having the thickness of about 400 Å. Subsequently, on the electron transport layer, the electron injection layer having the thickness of about 10 Å was formed by using Liq represented by Chemical Formula 17.

On the electron injection layer, the second electrode using the aluminum thin film having the thickness of 1,000 Å was formed to manufacture light-emitting element C-1 including the compound according to Example 3 of the present invention.

Light-emitting elements C-2, C-3, and C-4 were manufactured through the process that was substantially the same as the process of manufacturing the light-emitting element C-1, except that the first blocking layer was manufactured by using each of the compounds according to Examples 5, 8, and 10 of the present invention.

Manufacturing of Comparative Elements 7 and 8

Comparative element 7 was manufactured through the process that was substantially the same as the process of manufacturing the light-emitting element C-1, except that the first blocking layer was manufactured by using the compound according to Comparative Example 1 represented by Chemical Formula a.

Comparative element 8 was manufactured through the process that was substantially the same as the process of manufacturing the light-emitting element C-1, except that the first blocking layer was manufactured by using the compound according to Comparative Example 4 represented by Chemical Formula d.

Evaluation of Power Efficiency and Life-Span of Light-Emitting Element-3

With respect to each of light-emitting elements C-1 to C-4 and comparative elements 7 and 8 as prepared in the above, power efficiency was measured based on the value when luminance is 500 cd/m$^2$ by the method that was substantially the same as in the power efficiency measurement experiment of the light-emitting elements A-1 to A-10.

Further, the life-span of each of light-emitting elements C-1 to C-4 and comparative elements 7 and 8 was measured by the method that was substantially the same as the aforementioned life-span evaluation experiment of light-emitting elements A-1 to A-10.

The results of power efficiency and the life-span of each of the light-emitting elements C-1 to C-4 and comparative elements 7 and 8 are described in Table 7. In Table 7, a unit of the measurement result of power efficiency is lm/W. Further, in Table 7, in the case where initial luminance of the light-emitting element is 1,000 cd/m$^2$, $T_{75}$ means a time required until luminance of the light-emitting element becomes 75% of the initial luminance.

TABLE 7

| Element No. | Power efficiency [lm/W] | Life-span ($T_{75}$@85° C. [hr]) |
|---|---|---|
| Light-emitting element C-1 | 21.0 | 483 |
| Light-emitting element C-2 | 15.3 | 354 |
| Light-emitting element C-3 | 18.2 | 419 |
| Light-emitting element C-4 | 14.0 | 318 |
| Comparative element 7 | 8.2 | 201 |
| Comparative element 8 | 7.7 | 179 |

Referring to Table 7, it can be seen that power efficiency of each of light-emitting elements C-1 to C-4 is at least 14.0 lm/W and thus power efficiency of about 10 lm/W or more is exhibited, but power efficiency of comparative element 7 is just about 8.2 lm/W and power efficiency of comparative element 8 is about 7.7 lm/W.

Further, it can be seen that the life-span of each of light-emitting elements C-1 to C-4 is at least about 318 hours, and as compared to the life-spans of comparative element 7 and comparative element 8 which are about 201 hours and about 179 hours, the life-span of light-emitting elements according to the present invention is long.

Further, in consideration of evaluation of the life-span property of the light-emitting element performed under the acceleration condition (severe condition) of 85° C., from the fact that the life-span property of the light-emitting element including the compound according to the present invention is better than that of comparative elements 7 and 8, it can be seen that heat resistance of the light-emitting element manufactured by using the compound according to the present invention is good.

Manufacturing of Light-Emitting Elements D-1 to D-4

On the first electrode formed of indium-tin oxide (ITO), the compound according to Example 2 as the host material was evaporated at the rate of 1 Å/sec, and simultaneously, the P-type dopant (HAT-CN) represented by the following Chemical Formula 12 was co-evaporated at the ratio of about 5 parts by weight based on 100 parts by weight of the host material to form the first layer having the thickness of 100 Å. On the first layer, NPB was evaporated in the thickness of 300 Å to form the second layer. On the second layer, mCBP represented by Chemical Formula 13 and Ir(ppy)$_3$ represented by Chemical Formula 14 were co-evaporated at the weight ratio of 100:9 to form the light emitting layer having the thickness of about 300 Å, and on the light emitting layer, mCBP was evaporated again in the thickness of about 50 Å to form the blocking layer.

Then, on the blocking layer, BPhen represented by Chemical Formula 15 and Alga represented by Chemical Formula 16 were co-evaporated at the weight ratio of 50:50 to form the electron transport layer having the thickness of about 400 Å. Subsequently, on the electron transport layer, the electron injection layer having the thickness of about 10 Å was formed by using Liq represented by Chemical Formula 17.

On the electron injection layer, the second electrode using the aluminum thin film having the thickness of 1,000 Å was formed to manufacture light-emitting element D-1 including the compound according to Example 2 of the present invention.

Light-emitting elements D-2, D-3, and D-4 were manufactured through the process that was substantially the same as the process of manufacturing the light-emitting element D-1, except that the first layer was manufactured by using each of the compounds according to Examples 4, 7, and 9 of the present invention.

Manufacturing of Comparative Elements 9 and 10

Comparative element 9 was manufactured through the process that was substantially the same as the process of manufacturing the light-emitting element D-1, except that the host material of the first layer was manufactured by using the compound according to Comparative Example 1 represented by Chemical Formula a.

Comparative element 10 was manufactured through the process that was substantially the same as the process of manufacturing the light-emitting element D-1, except that the host material of the first layer was manufactured by using the compound according to Comparative Example 4 represented by Chemical Formula d.

Evaluation of Power Efficiency and Life-Span of Light-Emitting Element-4

With respect to each of light-emitting elements D-1 to D-4 and comparative elements 9 and 10 as prepared in the above, power efficiency was measured based on the value when luminance is 500 cd/m$^2$ by the method that was substantially the same as the power efficiency measurement experiment of the light-emitting elements A-1 to A-10.

Further, the life-span of each of light-emitting elements D-1 to D-4 and comparative elements 9 and 10 was measured by the method that was substantially the same as the aforementioned life-span evaluation experiment of light-emitting elements A-1 to A-10.

The results of power efficiency and the life-span of each of the light-emitting elements D-1 to D-4 and comparative elements 9 and 10 are described in Table 8. In Table 8, a unit of the measurement result of power efficiency is lm/W. Further, in Table 8, in the case where initial luminance of the light-emitting element is 1,000 cd/m$^2$, $T_{75}$ means a time required until luminance of the light-emitting element becomes 75% of the initial luminance.

TABLE 8

| Element No. | Power efficiency [lm/W] | Life-span ($T_{75}$@85° C. [hr]) |
|---|---|---|
| Light-emitting element D-1 | 18.1 | 437 |
| Light-emitting element D-2 | 23.1 | 532 |
| Light-emitting element D-3 | 20.0 | 471 |
| Light-emitting element D-4 | 18.3 | 416 |
| Comparative element 9 | 9.5 | 258 |
| Comparative element 10 | 9.1 | 210 |

Referring to Table 8, it can be seen that power efficiency of each of light-emitting elements D-1 to D-4 is at least 18.1 lm/W but power efficiency of comparative element 9 is just about 9.5 lm/W and power efficiency of comparative element 10 is just about 9.1 lm/W.

Further, it can be seen that the life-span of each of light-emitting elements D-1 to D-4 is at least about 416 hours or more, but as compared to the life-spans of comparative elements 9 and 10 are about 258 hours and just about 210 hours, respectively, the life-span of light-emitting elements D-1 to D-4 is relatively longer than that of comparative elements 9 and 10.

Further, in consideration of evaluation of the life-span property of the light-emitting element performed under the acceleration condition (severe condition) of 85° C., from the fact that that the life-span property of the light-emitting element including the compound according to the present invention is better than that of comparative elements 9 and 10, it can be seen that heat resistance of the light-emitting element manufactured by using the compound according to the present invention is good.

Manufacturing of Light-Emitting Elements E-1 to E-4

On the first electrode formed of indium-tin oxide (ITO), NPB as the host material was evaporated at the rate of 1 Å/sec, and simultaneously, the P-type dopant (HAT-CN) represented by the following Chemical Formula 12 was co-evaporated at the ratio of about 5 parts by weight based on 100 parts by weight of the host material to form the first layer having the thickness of 100 Å. On the first layer, the compound according to Example 1 was evaporated in the thickness of 300 Å to form the second layer. On the second layer, mCBP represented by Chemical Formula 13 and Ir(ppy)$_3$ represented by Chemical Formula 14 were co-evaporated at the weight ratio of 100:9 to form the light emitting layer having the thickness of about 300 Å, and on the light emitting layer, mCBP was evaporated again in the thickness of about 50 Å to form the blocking layer.

Then, on the blocking layer, BPhen represented by Chemical Formula 15 and Alga represented by Chemical Formula 16 were co-evaporated at the weight ratio of 50:50 to form the electron transport layer having the thickness of about 400 Å. Subsequently, on the electron transport layer, the electron injection layer having the thickness of about 10 Å was formed by using Liq represented by Chemical Formula 17.

On the electron injection layer, the second electrode using the aluminum thin film having the thickness of 1,000 Å was formed to manufacture light-emitting element E-1 including the compound according to Example 1 of the present invention.

Light-emitting elements E-2, E-3, and E-4 were manufactured through the process that was substantially the same as the process of manufacturing the light-emitting element E-1, except that the second layer was manufactured by using each of the compounds according to Examples 5, 8, and 9 of the present invention.

Manufacturing of Comparative Elements 11 and 12

Comparative element 11 was manufactured through the process that was substantially the same as the process of manufacturing the light-emitting element E-1, except that the second layer was manufactured by using the compound according to Comparative Example 1 represented by Chemical Formula a.

Comparative element 12 was manufactured through the process that was substantially the same as the process of manufacturing the light-emitting element E-1, except that the second layer was manufactured by using the compound according to Comparative Example 4 represented by Chemical Formula d.

Evaluation of Power Efficiency and Life-Span of Light-Emitting Element-5

With respect to each of light-emitting elements E-1 to E-4 and comparative elements 11 and 12 as prepared in the above, power efficiency was measured based on the value when luminance is 500 cd/m$^2$ by the method that was substantially the same as the power efficiency measurement experiment of the light-emitting elements A-1 to A-10.

Further, the life-span of each of light-emitting elements E-1 to E-4 and comparative elements 11 and 12 was measured by the method that was substantially the same as the aforementioned life-span evaluation experiment of light-emitting elements A-1 to A-10.

The results of power efficiency and the life-span of each of the light-emitting elements E-1 to E-4 and comparative elements 11 and 12 are shown in Table 9. In Table 9, a unit of the measurement result of power efficiency is lm/W. Further, in Table 9, in the case where initial luminance of the light-emitting element is 1,000 cd/m$^2$, $T_{75}$ means a time required until luminance of the light-emitting element becomes 75% of the initial luminance.

TABLE 9

| Element No. | Power efficiency [lm/W] | Life-span ($T_{75}$@85° C. [hr]) |
|---|---|---|
| Light-emitting element E-1 | 26.9 | 624 |
| Light-emitting element E-2 | 18.9 | 435 |
| Light-emitting element E-3 | 22.5 | 517 |
| Light-emitting element E-4 | 17.3 | 397 |
| Comparative element 11 | 9.1 | 220 |
| Comparative element 12 | 9.5 | 223 |

Referring to Table 9, it can be seen that power efficiency of each of light-emitting elements E-1 to E-4 is at least 17.3 lm/W and power efficiency of about 10 lm/W or more is exhibited, but power efficiency of comparative element 11 is about 9.1 lm/W and power efficiency of comparative element 12 is just about 9.5 lm/W.

Further, it can be seen that the life-span of each of light-emitting elements E-1 to E-4 is at least about 397 hours, but as compared to the life-spans of comparative elements 11 and 12 are about 220 hours and just about 223 hours, respectively, the life-span property of light-emitting elements E-1 to E-4 is relatively better than that of comparative elements 11 and 12.

Further, in consideration of evaluation of the life-span property of the light-emitting element performed under the acceleration condition (severe condition) of 85° C., from the fact that that the life-span property of the light-emitting element including the compound according to the present invention is better than that of comparative elements 11 and 12, it can be seen that heat resistance of the light-emitting element manufactured by using the compound according to the present invention is good.

According to the aforementioned description, a light-emitting element having improved power efficiency, life-span, and thermal stability may be manufactured by using the novel compound according to the present invention.

EXPLANATION OF CODES

| | |
|---|---|
| 100, 102, 104: Light-emitting element | 10: Base substrate |
| 20: First electrode | 30, 32, 34: Hole transportable layer |
| 33a: First layer | 33b: Second layer |
| 40: Light emitting layer | 50: Second electrode |

What is claimed is:

1. A light-emitting element comprising:
a first electrode;
a second electrode;
a light emitting layer disposed between the first electrode and the second electrode; and
a hole transportable layer disposed between the first electrode and the light emitting layer and including a compound represented by the following Chemical Formula 1:

[Chemical Formula 1]

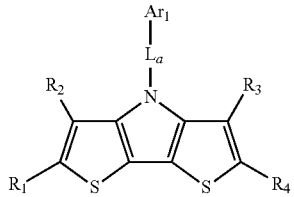

in Chemical Formula 1,
$R_1$, $R_2$, $R_3$, and $R_4$ each independently represent *-$L_b$-Z or hydrogen, wherein one or two of $R_1$, $R_2$, $R_3$, and $R_4$ represents *-$L_b$-Z,
Z is represented by the following Chemical Formula 2 or the following Chemical Formula 3,

[Chemical Formula 2]

[Chemical Formula 3]

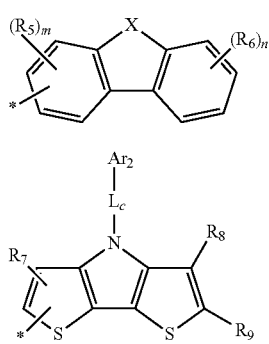

X represents N-$L_d$-$Ar_3$, or Si($R_{10}$)($R_{11}$),
$Ar_1$, $Ar_2$, and $Ar_3$ each independently represent *-$A_1$-$A_2$-$A_3$-$A_4$, $A_1$, $A_2$ and $A_3$ each independently represent a single bond, an arylene group having 6 to 60 carbon atoms or a heteroarylene group having 2 to 60 carbon atoms, $A_4$ represents aryl group having 6 to 60 carbon atoms, or a heteroaryl group having 2 to 60 carbon atoms, $R_5$, $R_6$, $R_7$, $R_8$, $R_9$, $R_{10}$, and $R_{11}$ each independently represent hydrogen, an alkyl group having 1 to 10 carbon atoms, an alkenyl group having 2 to 60 carbon atoms, an alkynyl group having 2 to 60 carbon atoms, a cycloalkyl group having 3 to 60 carbon atoms, an aryl group having 6 to 60 carbon atoms, or a heteroaryl group having 2 to 60 carbon atoms, m represents an integer of 0 to 3, and n represents an integer of 0 to 4, $L_a$, $L_c$, and $L_d$ each independently represent a single bond, $L_b$ represents a single bond, an arylene group having 6 to 60 carbon atoms, or a heteroarylene group having 2 to 60 carbon atoms, and one or more of hydrogens of the *$L_b$-Z, and the $Ar_1$ of Chemical Formula 1 are each independently unsubstituted or substituted by one or more substituent groups selected from the group consisting of an alkyl group having 1 to 6 carbon atoms, an alkenyl group having 2 to 6 carbon atoms, an alkoxy group having 1 to 6 carbon atoms, an aryl group having 6 to 60 carbon atoms, a heteroaryl group having 2 to 60 carbon atoms, an aryloxy group having 6 to 60 carbon atoms, an arylthio group having 6 to 60 carbon atoms, an alkoxycarbonyl group having 1 to 6 carbon atoms, a halogen group, a cyano group, a nitro group, a hydroxyl group, and a carboxyl group.

2. The light-emitting element of claim 1, wherein the hole transportable layer further includes a P-type dopant.

3. The light-emitting element of claim 1, wherein the hole transportable layer includes a first layer including the compound and a P-type dopant; and a second layer including the compound.

4. An electronic device comprising:
the light-emitting element according to claim 1.

5. The electronic device of claim 4, wherein the electronic device is a display device or a lighting device.

6. The light-emitting element of claim 1, wherein the compound represented by Chemical Formula 1 is represented by the following Chemical Formula 4:

[Chemical Formula 4]

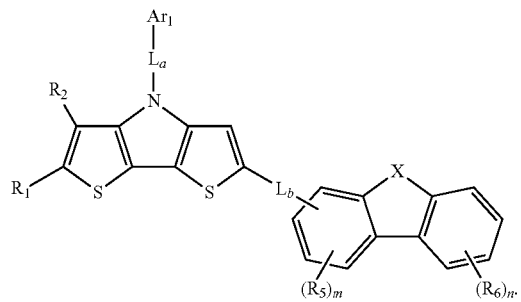

7. The light-emitting element of claim 1, wherein the compound represented by Chemical Formula 1 is represented by the following Chemical Formula 5:

[Chemical Formula 5]

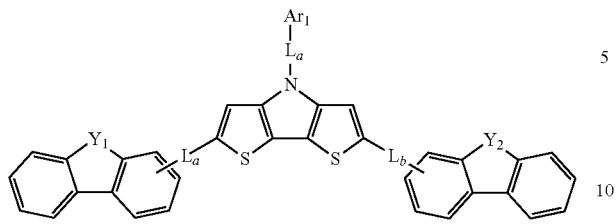

in the Chemical Formula 5, $Y_1$ and $Y_2$ each independently represent N-$L_f$-$Ar_4$ or $Si(R_{12})(R_{13})$, $L_e$, and $L_f$ each independently represent a single bond, an arylene group having 6 to 30 carbon atoms, or a heteroarylene group having 2 to 30 carbon atoms, $Ar_4$ represents hydrogen, an aryl group having 6 to 30 carbon atoms, or a heteroaryl group having 3 to 30 carbon atoms, and $R_{12}$ and $R_{13}$ each independently represent hydrogen, an alkyl group having 1 to 10 carbon atoms, an alkenyl group having 2 to 30 carbon atoms, an alkynyl group having 2 to 30 carbon atoms, a cycloalkyl group having 3 to 30 carbon atoms, a heterocycloalkyl group having 2 to 30 carbon atoms, an aryl group having 6 to 30 carbon atoms, or a heteroaryl group having 2 to 30 carbon atoms.

8. The light-emitting element of claim 1, wherein the compound represented by Chemical Formula 1 is represented by the following Chemical Formula 6:

[Chemical Formula 6]

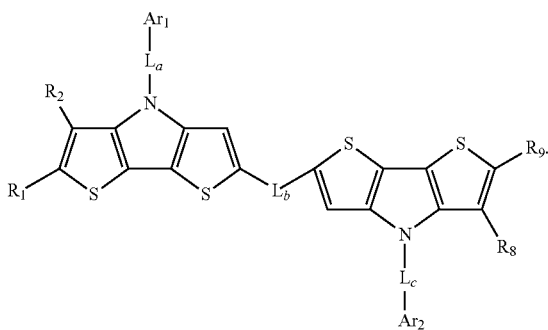

9. The light-emitting element of claim 1, wherein the compound represented by Chemical Formula 1 is selected from the following structures:

<Structure 1>

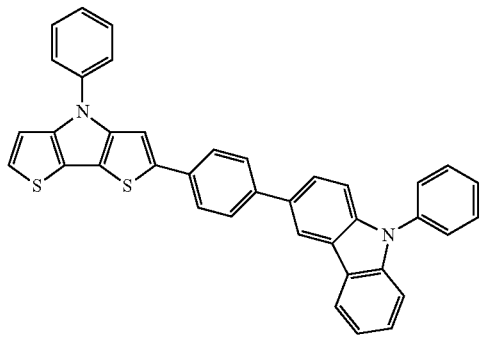

<Structure 2>

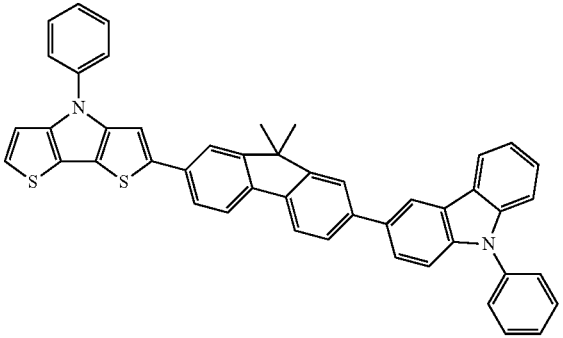

<Stucture 3>

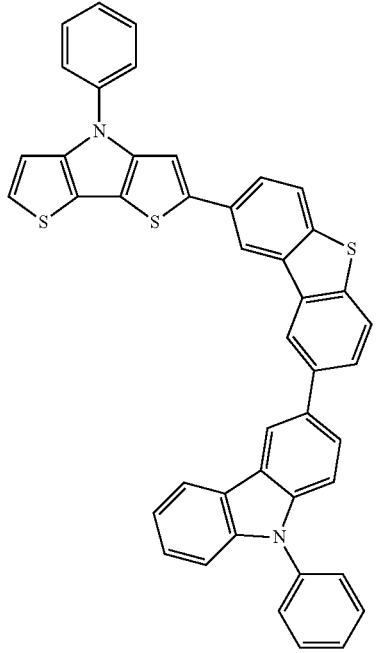

<Structure 4>

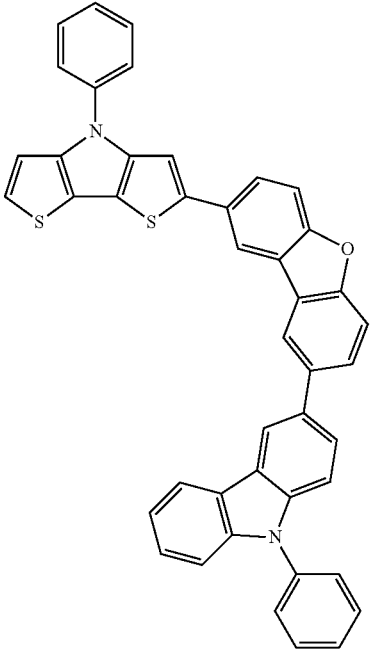

-continued
<Structure 5>
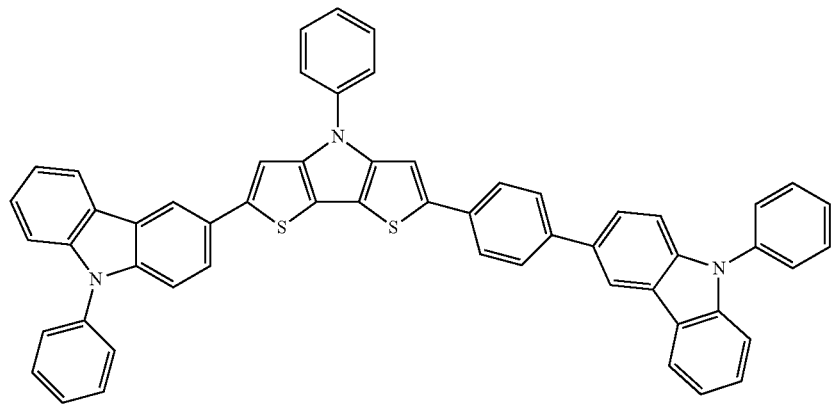
<Structure 8>
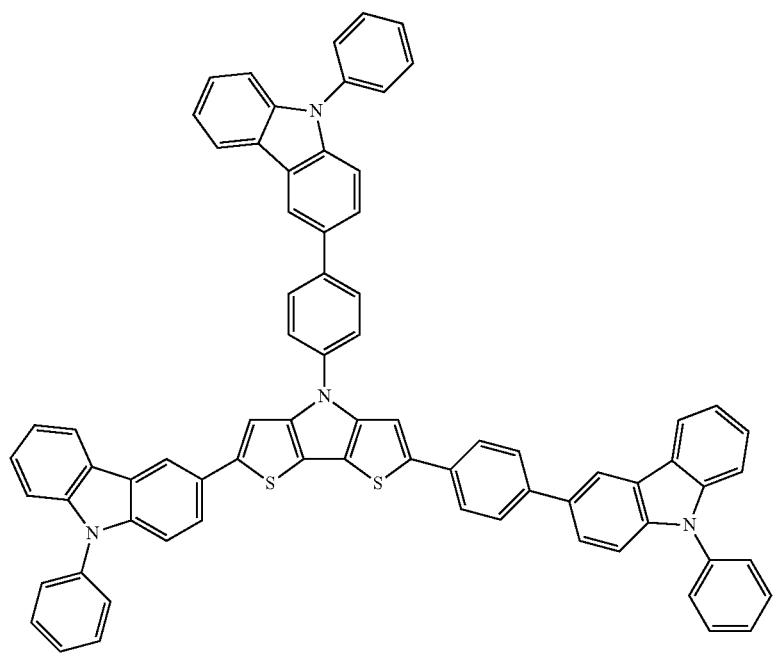
<Structure 9>
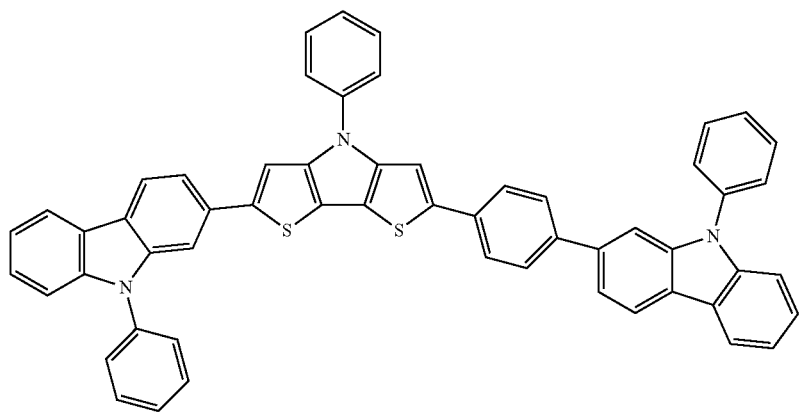

\<Structure 10\>
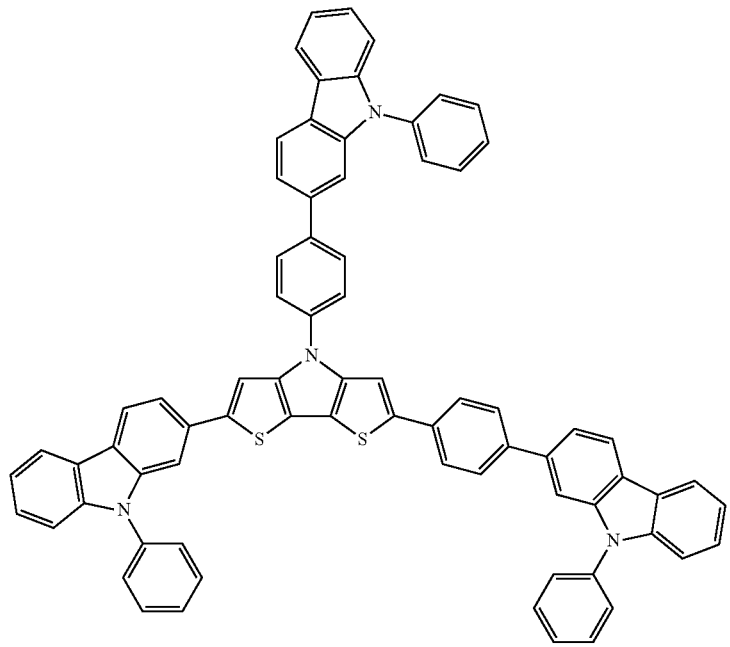
\<Structure 11\> \<Structure 12\>
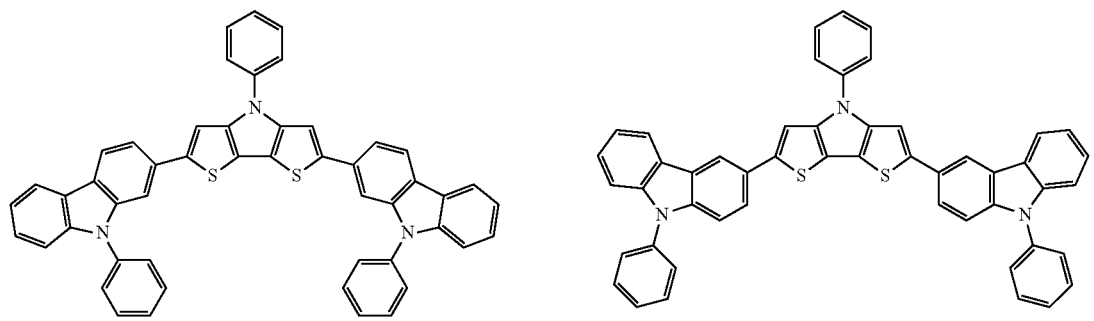
\<Structure 13\>
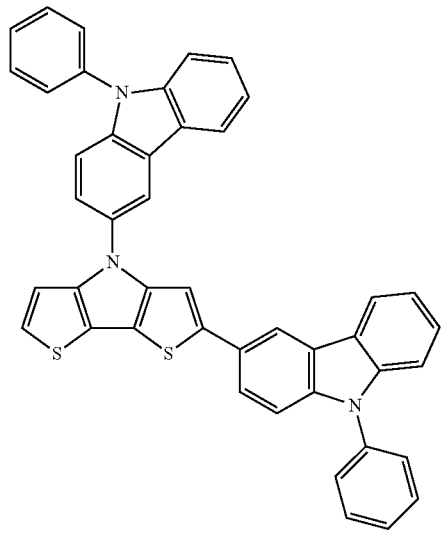

-continued
<Structure 15>
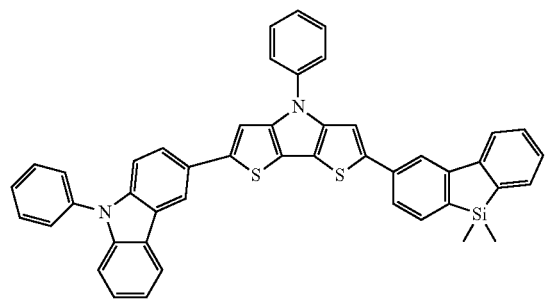
<Structure 16>
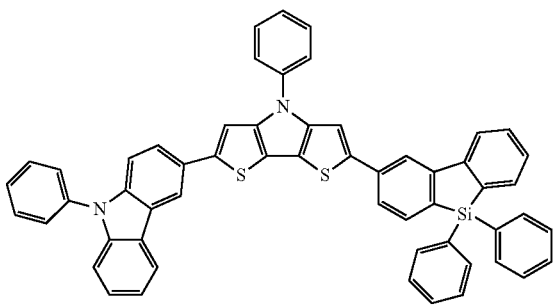
<Structure 17>
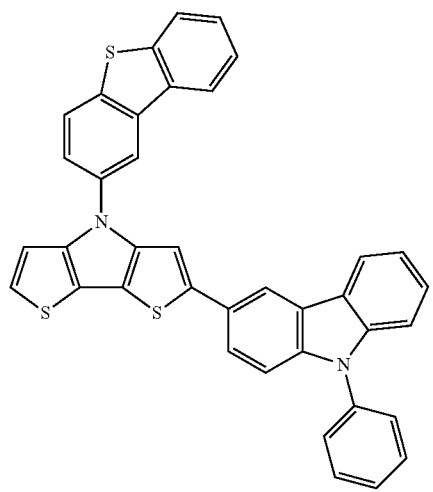
<Strucutre 18>
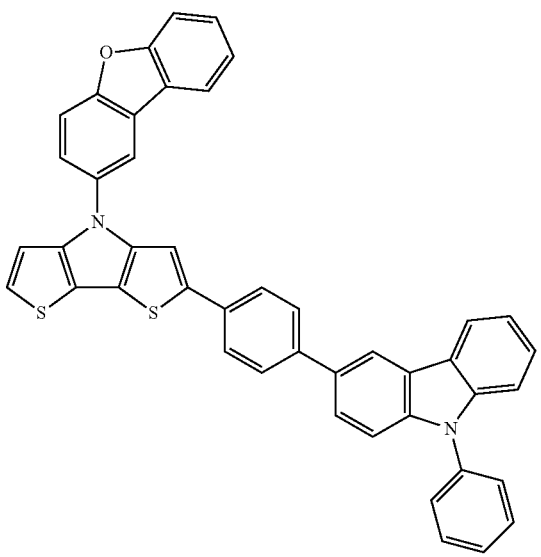
<Structure 21>
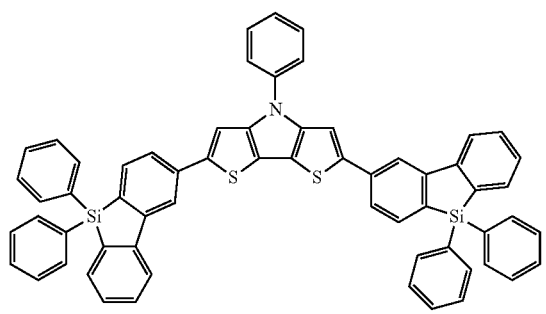
<Structure 22>
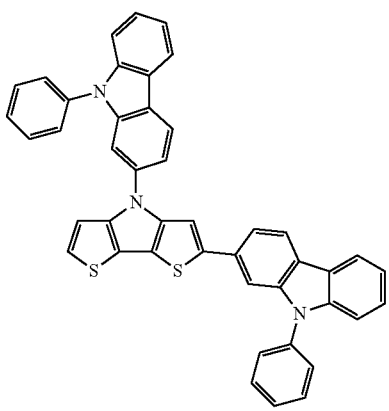

<Structure 23>
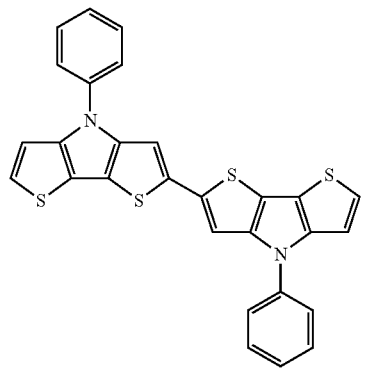
<Structure 24>
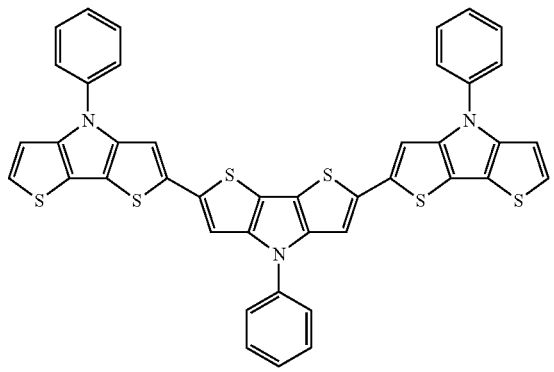
<Structure 25>
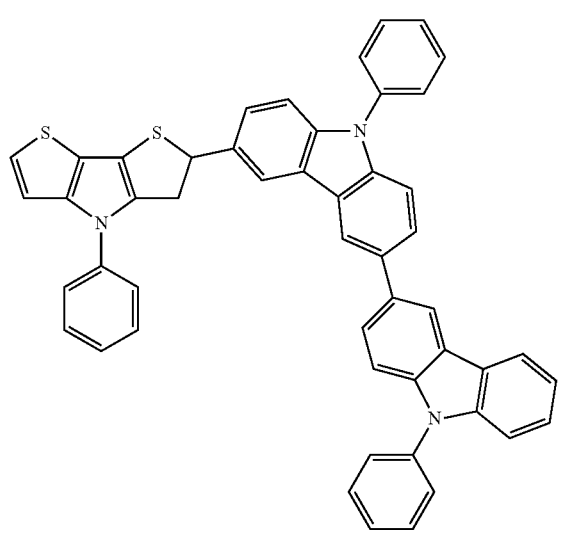
<Structure 26>
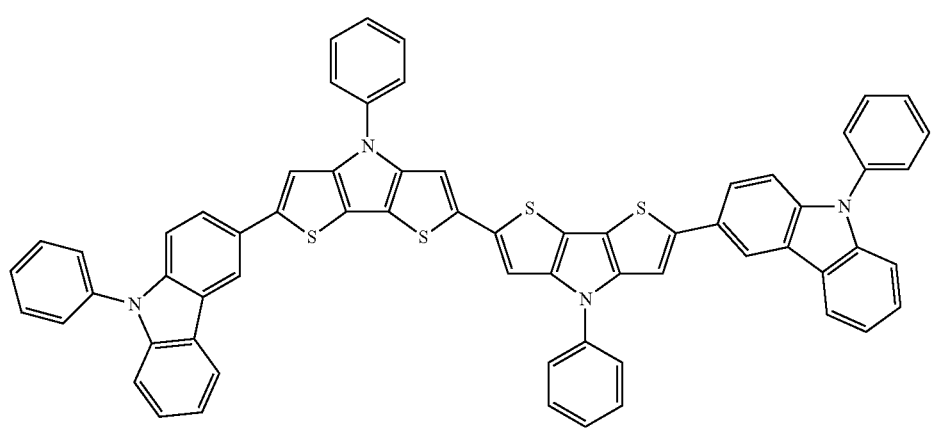

-continued
<Structure 27>
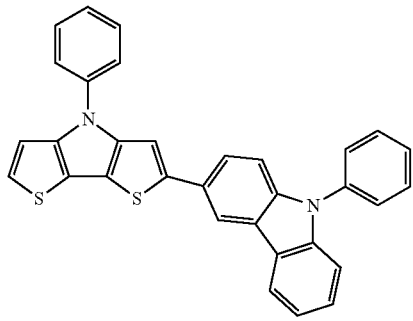
<Structure 28>
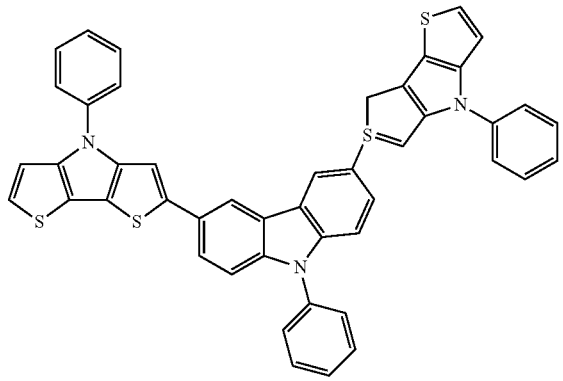
<Structure 29>
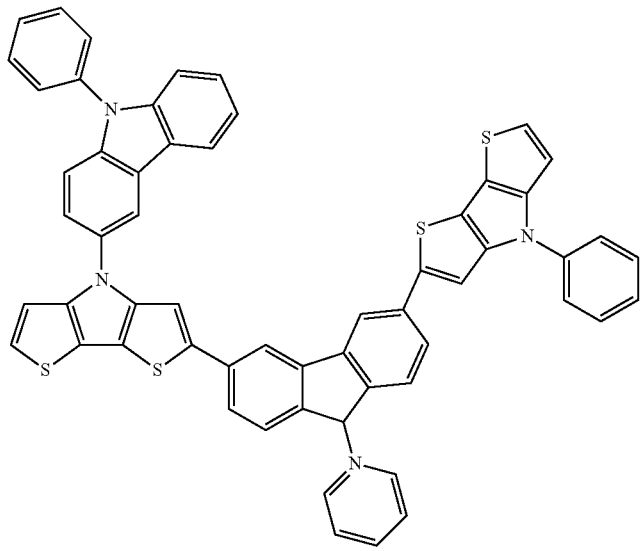
<Structure 30>
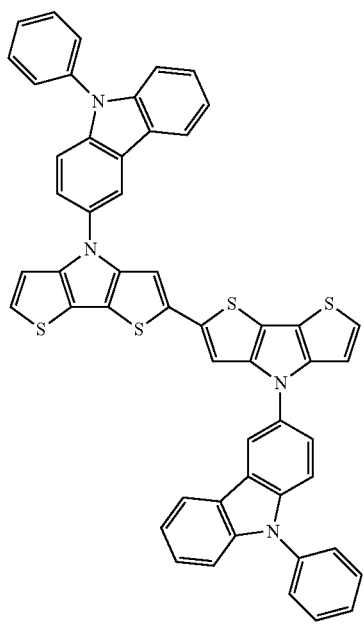
<Structure 31>
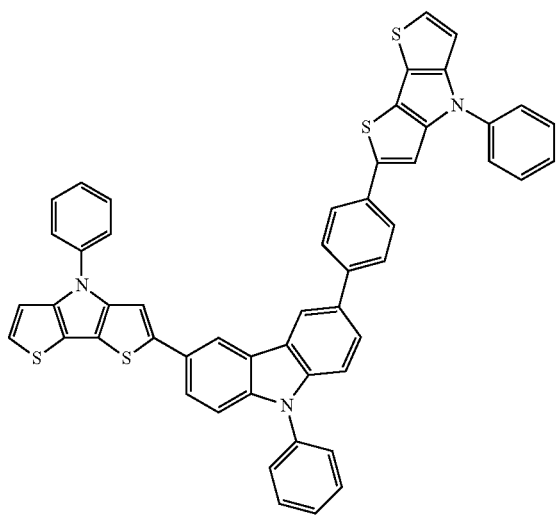

-continued
<Structure 32>
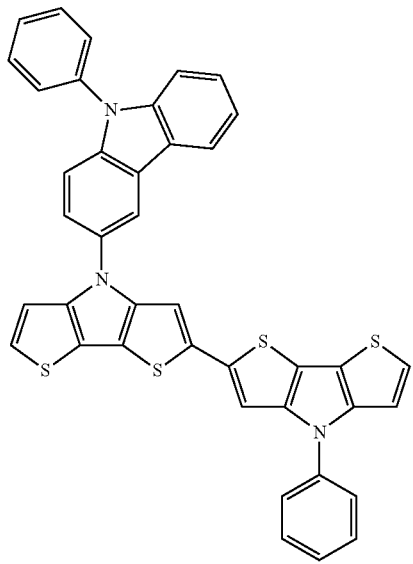
<Structure 33>
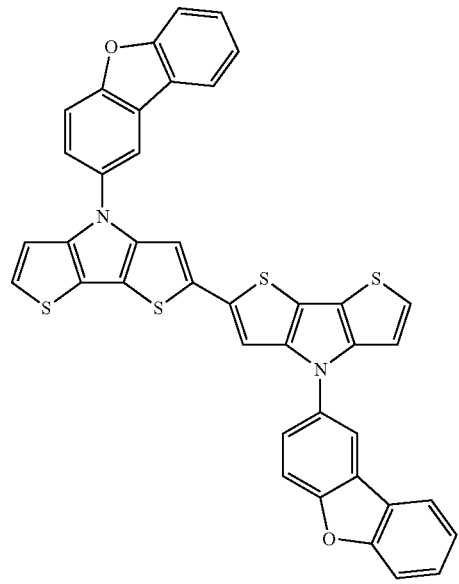
<Structure 34>
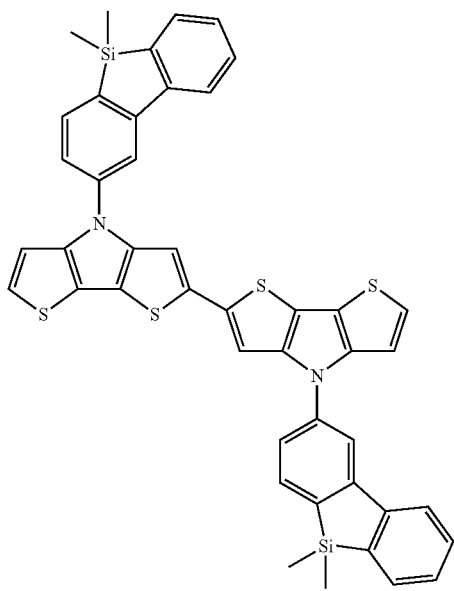
<Structure 35>
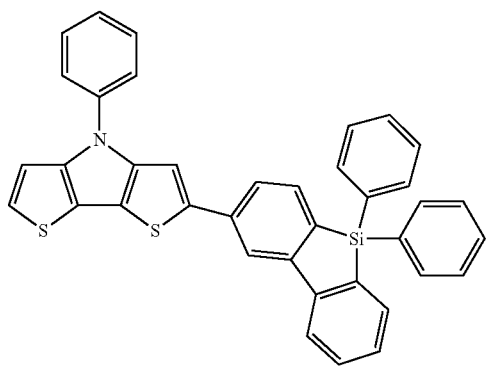

-continued
<Structure 36>
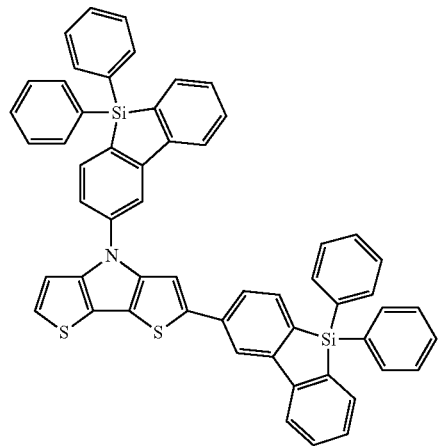
<Structure 37>
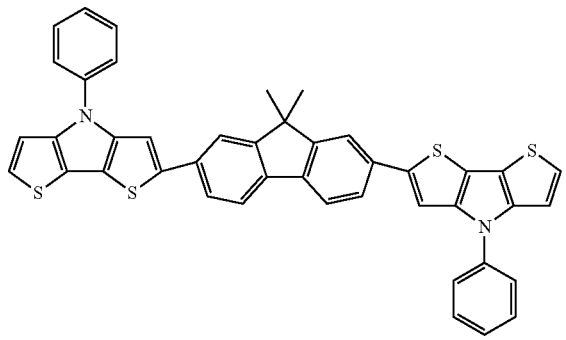
<Structure 38>
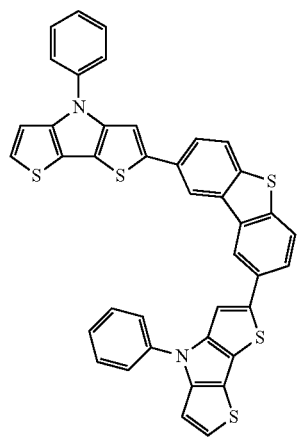
<Structure 39>
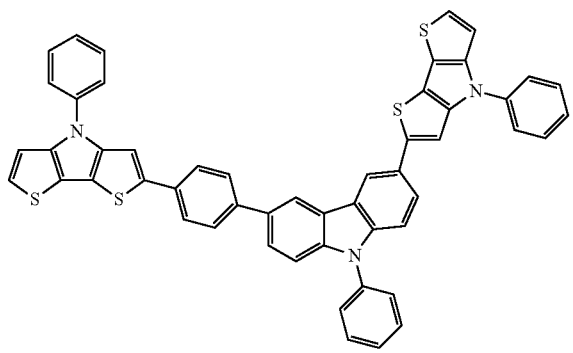
<Structure 40>
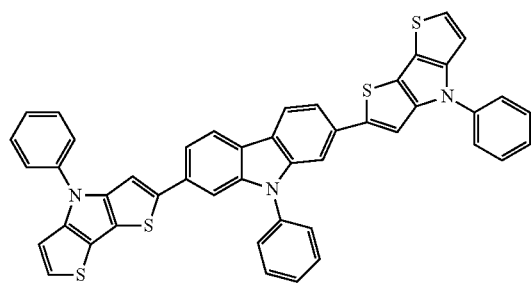
<Structure 41>
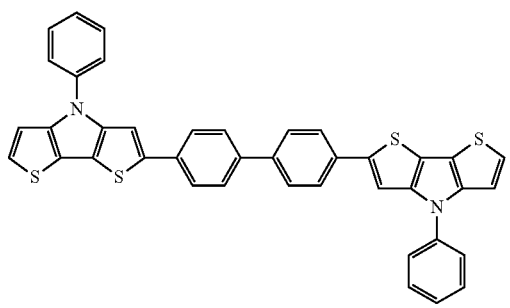

-continued
<Structure 42>
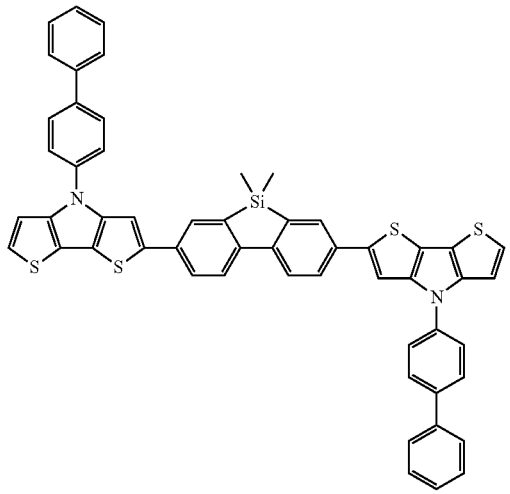
<Structure 43>
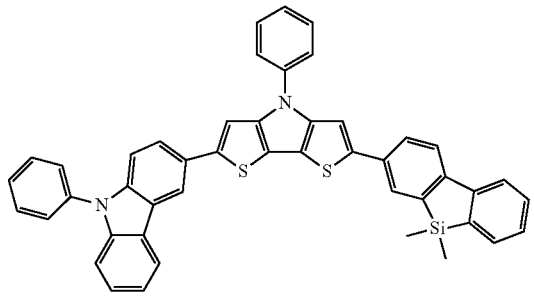
<Structure 44>
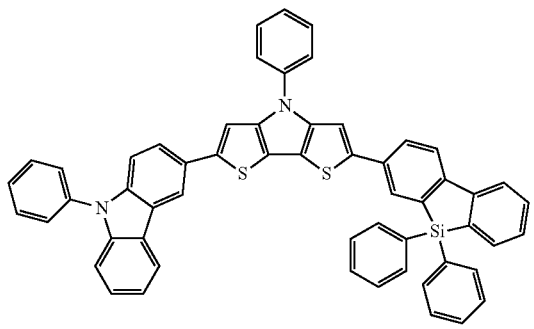
<Structure 45>
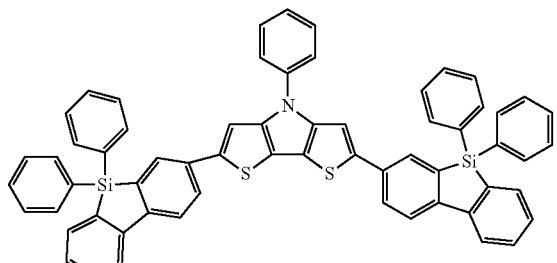
<Structure 46>
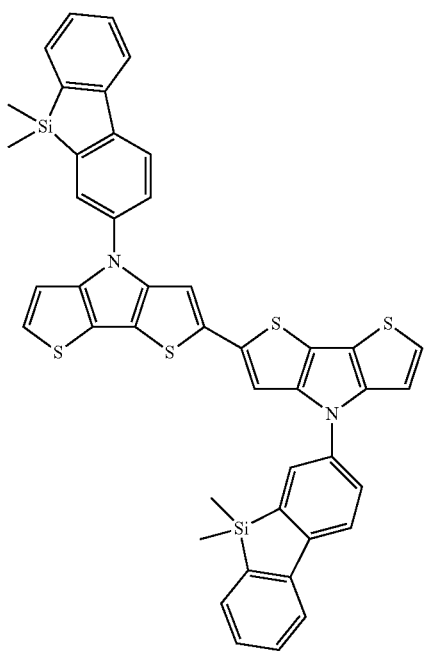
<Structure 47>
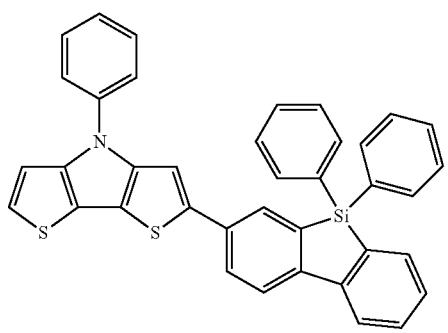

-continued
<Structure 48>
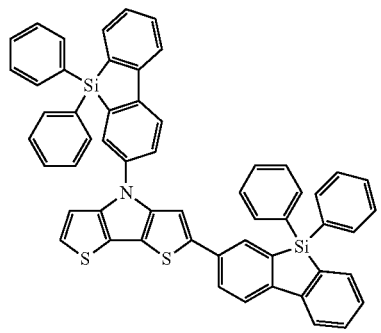
<Structure 49>
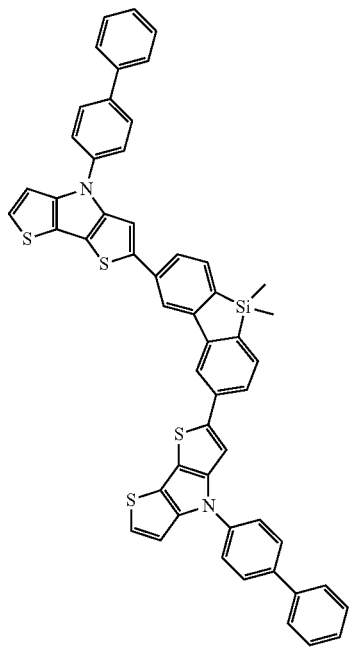
<Structure 50>
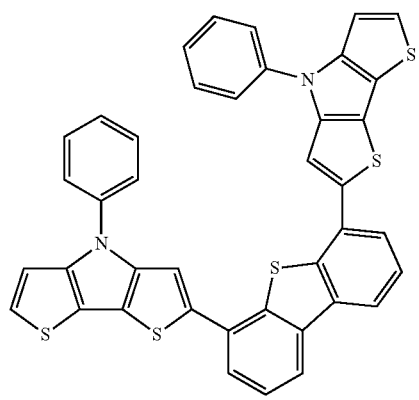
<Structure 51>
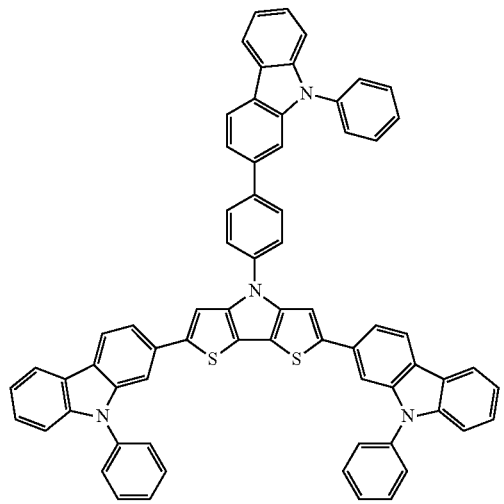
<Structure 52>
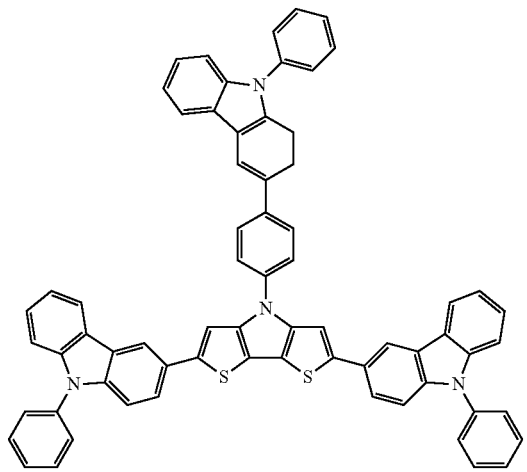

-continued
<Structure 53>
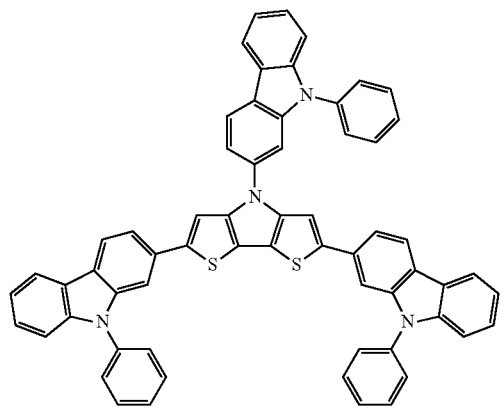
<Structure 54>
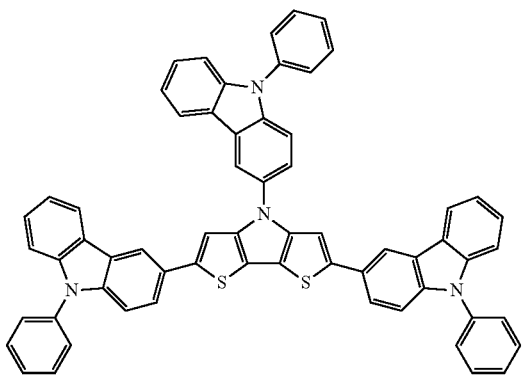
<Structure 64>
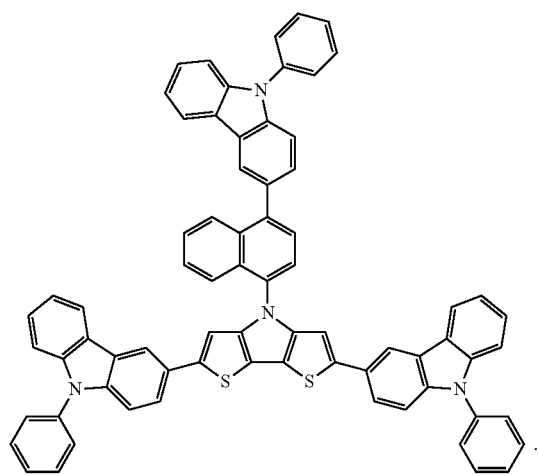
* * * * *